United States Patent
Simpson et al.

(10) Patent No.: US 12,291,734 B2
(45) Date of Patent: May 6, 2025

(54) MICROORGANISMS AND METHODS FOR THE CONTINUOUS CO-PRODUCTION OF HIGH-VALUE, SPECIALIZED PROTEINS AND CHEMICAL PRODUCTS FROM C1-substrates

(71) Applicant: LanzaTech, Inc., Skokie, IL (US)

(72) Inventors: Sean Dennis Simpson, Evanston, IL (US); Michael Koepke, Chicago, IL (US); James Macallister Clomburg, Chicago, IL (US); Juniper Dee Gramling, Skokie, IL (US); Stephanie Rhianon Jones, Evanston, IL (US); Jaeyoung Jung, San Francisco, CA (US); Timothy James Politano, Chicago, IL (US); Ryan Christopher Tappel, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 18/339,027

(22) Filed: Jun. 21, 2023

(65) Prior Publication Data
US 2024/0026413 A1 Jan. 25, 2024

Related U.S. Application Data

(60) Provisional application No. 63/366,757, filed on Jun. 21, 2022, provisional application No. 63/497,045, filed on Apr. 19, 2023.

(51) Int. Cl.
C12P 21/02 (2006.01)

(52) U.S. Cl.
CPC .................................. C12P 21/02 (2013.01)

(58) Field of Classification Search
CPC ...... C12N 9/88; C12N 9/0008; C12N 9/1022; C12N 15/52; C12N 15/74; C12P 7/18; C12P 7/06; C12Y 102/07001; C12Y 202/01006; C12Y 401/01005; Y02E 50/10
See application file for complete search history.

(56) References Cited

U.S. PATENT DOCUMENTS

| | | |
|---|---|---|
| 1,128,549 A | 2/1915 | Tait |
| 1,408,091 A | 2/1922 | Kellam |
| 2,099,090 A | 11/1937 | Webb |
| 2,218,234 A | 10/1940 | Fisher |
| 2,405,986 A | 8/1946 | Sullivan |
| 2,769,321 A | 11/1956 | Stiles |
| 3,020,708 A | 2/1962 | Mahan |
| 3,102,875 A | 9/1963 | Heiss |
| 4,692,168 A | 9/1987 | Dotson |
| 5,173,429 A | 12/1992 | Gaddy |
| 5,552,023 A | 9/1996 | Zhou |
| 5,593,886 A | 1/1997 | Gaddy |
| 6,368,819 B1 | 4/2002 | Gaddy |
| 6,451,576 B1 | 9/2002 | Bruce et al. |
| 6,811,769 B2 | 11/2004 | Watanabe |
| 7,951,980 B2 | 5/2011 | Reimann |
| 7,972,824 B2 | 7/2011 | Simpson |
| 8,158,383 B2 | 4/2012 | Keasling et al. |
| 8,293,509 B2 | 10/2012 | Simpson |
| 8,349,587 B2 | 1/2013 | Fischer |
| 8,658,845 B2 | 2/2014 | Oroskar |
| 8,900,836 B2 | 12/2014 | Simpson |
| 9,023,636 B2 | 5/2015 | Burk |
| 9,068,202 B2 | 6/2015 | Tran |
| 9,121,039 B2 | 9/2015 | Chotani |
| 9,163,264 B2 | 10/2015 | Green |
| 9,284,564 B2 | 3/2016 | Mueller |
| 9,347,076 B2 | 5/2016 | Liew |
| 9,359,611 B2 | 6/2016 | Koepke |
| 9,410,130 B2 | 8/2016 | Koepke |
| 9,464,301 B2 | 10/2016 | Beck et al. |
| 9,738,875 B2 | 8/2017 | Koepke |
| 9,890,384 B2 | 2/2018 | Mueller |
| 9,902,980 B2 | 2/2018 | Fischer |
| 9,994,878 B2 | 6/2018 | Koepke |
| 10,017,787 B2 | 7/2018 | Anissimova |
| 10,131,924 B2 | 11/2018 | Hellingwerf |
| 10,174,303 B2 | 1/2019 | Behrendorff |
| 10,174,349 B2 | 1/2019 | Reinecke |
| 10,435,516 B2 | 10/2019 | Widmaier |

(Continued)

FOREIGN PATENT DOCUMENTS

| | | |
|---|---|---|
| CN | 102015995 A | 4/2011 |
| CN | 104651388 A | 5/2015 |
| CN | 110656078 A | 1/2020 |
| CN | 114410697 B | 7/2024 |
| EP | 0230702 A1 | 8/1987 |
| EP | 0462836 A2 | 12/1991 |
| EP | 2909231 B1 | 10/2020 |
| WO | 1992008555 A1 | 5/1992 |
| WO | 1997010331 A1 | 3/1997 |
| WO | 0208438 A2 | 1/2002 |
| WO | 2006088491 A2 | 8/2006 |
| WO | 2008028055 A2 | 3/2008 |
| WO | 2009064200 A2 | 5/2009 |

(Continued)

OTHER PUBLICATIONS

Chockalingam et al., Engineering and characterization of human manganese superoxide dismutase mutants with high activity and low product inhibition. FEBS J., 2006, vol. 273: 4853-4861. (Year: 2006).*

(Continued)

Primary Examiner — Ganapathirama Raghu

(57) ABSTRACT

Microorganisms are genetically engineered to continuously co-produce amino acids, high-value, specialized proteins, microbial biomass, chemicals, or any combination thereof by microbial fermentation, particularly by microbial fermentation of a gaseous substrate. The microorganisms are C1-fixing. The production of ethylene, microbial biomass, and heterologous high-value, specialized proteins can be improved. This can be improved by varying promoters or nutrient limiting means.

7 Claims, 19 Drawing Sheets

Specification includes a Sequence Listing.

(56) References Cited

U.S. PATENT DOCUMENTS

| | | | |
|---|---|---|---|
| 10,494,600 | B2 | 12/2019 | Heijstra |
| 10,590,406 | B2 | 3/2020 | Koepke |
| 10,647,975 | B2 | 5/2020 | Gamboa |
| 10,856,560 | B2 * | 12/2020 | Simpson ............... A23K 10/12 |
| 10,913,958 | B2 | 2/2021 | Koepke |
| 10,988,515 | B2 | 4/2021 | Kittleson |
| 11,053,287 | B2 | 7/2021 | Foster |
| 11,202,989 | B2 | 12/2021 | Winter |
| 11,555,209 | B2 | 1/2023 | Koepke |
| 2011/0236941 | A1 | 9/2011 | Koepke |
| 2012/0045807 | A1 | 2/2012 | Simpson |
| 2012/0276603 | A1 | 11/2012 | Beck et al. |
| 2013/0157322 | A1 | 6/2013 | Simpson |
| 2013/0210096 | A1 | 8/2013 | Schultz |
| 2013/0230609 | A1 | 9/2013 | Modak |
| 2014/0377857 | A1 | 12/2014 | Liao |
| 2015/0010978 | A1 | 1/2015 | Heaps et al. |
| 2015/0247170 | A1 | 9/2015 | Yu |
| 2015/0329882 | A1 | 11/2015 | Lee |
| 2016/0068578 | A1 | 3/2016 | Demirel et al. |
| 2016/0177353 | A1 | 6/2016 | Yu |
| 2017/0283809 | A1 | 10/2017 | Guntner |
| 2017/0298395 | A1 | 10/2017 | Tabita |
| 2018/0216120 | A1 | 8/2018 | Shetty |
| 2018/0245108 | A1 | 8/2018 | Reed |
| 2019/0002926 | A1 | 1/2019 | Cartman et al. |
| 2019/0124947 | A1 | 5/2019 | Pearlman |
| 2019/0300838 | A1 | 10/2019 | Smith |
| 2019/0300839 | A1 | 10/2019 | Smith |
| 2019/0367950 | A1 | 12/2019 | Edgar et al. |
| 2020/0165733 | A1 | 5/2020 | Reed |
| 2021/0010037 | A1 | 1/2021 | Fischer |
| 2021/0238609 | A1 | 8/2021 | Burgard et al. |
| 2021/0292732 | A1 | 9/2021 | Liew |
| 2022/0098560 | A1 | 3/2022 | Juminaga |
| 2022/0145337 | A1 | 5/2022 | Reed |
| 2023/0092645 | A1 | 3/2023 | Holmgren |

FOREIGN PATENT DOCUMENTS

| | | | |
|---|---|---|---|
| WO | 2009111513 | A1 | 9/2009 |
| WO | 2009151342 | A1 | 12/2009 |
| WO | 2010036951 | A2 | 4/2010 |
| WO | 2011034887 | A2 | 3/2011 |
| WO | 2012015317 | A1 | 2/2012 |
| WO | 2012110256 | A1 | 8/2012 |
| WO | 2012110257 | A1 | 8/2012 |
| WO | 2012175750 | A1 | 12/2012 |
| WO | 2014089436 | A1 | 6/2014 |
| WO | 2014100851 | A1 | 7/2014 |
| WO | 2015073854 | A2 | 5/2015 |
| WO | 2016138050 | A1 | 9/2016 |
| WO | 2016172716 | A2 | 10/2016 |
| WO | 2017161387 | A1 | 9/2017 |
| WO | 2018009770 | A1 | 1/2018 |
| WO | 2018144965 | A1 | 8/2018 |
| WO | 2021016523 | A1 | 1/2021 |
| WO | 2021113396 | A1 | 6/2021 |
| WO | 2021189003 | A1 | 9/2021 |
| WO | 2022066997 | A1 | 3/2022 |
| WO | 2023028459 | A1 | 3/2023 |

OTHER PUBLICATIONS

Pena-Francesch A., Tandem Repeat Proteins Inspired By Squid Ring Teeth, Ph.D., Thesis, 2017, The Pennsylvania State Univ., pp. 1-240. (Year: 2017).*

Devos et al., Practical limits of function prediction. Proteins: Structure, Function, and Genetics. 2000, vol. 41: 98-107 (Year: 2000).*

Whisstock et al., Prediction of protein function from protein sequence. Q. Rev. Biophysics., 2003, vol. 36 (3): 307-340. (Year: 2003).*

International Search Report and Written Opinion issued in International Application No. PCT/US2020/062938, dated May 24, 2021, 6 pages.

International Search Report and Written Opinion issued in International Application No. PCT/US2023/068821, dated Oct. 12, 2023, 10 pages.

International Search Report and Written Opinion issued in International Application No. PCT/US2023/068828, dated Oct. 12, 2023, 11 pages.

International Search Report and Written Opinion issued in International Application No. PCT/US2023/068832, dated Oct. 6, 2023, 15 pages.

Abrini et al., "*Clostridium autoethanogenum*, sp. nov., an anaerobic bacterium that produces ethanol from carbon monoxide", Arch Microbiol 1994, 4: 345-351.

Adams et al, "Engineering osmolysis susceptibility in Cupriavidus necator and *Escherichia coli* for recovery of intracellular products" ResearchSquare 2022, p. 1-28.

Alhasawi et al., "Isocitrate Lyase and Succinate Semialdehyde Dehydrogenase Mediate the Synthesis of α-Ketoglutarate in Pseudomonas fluorescens", Frontiers in Microbiology, Aug. 23, 2019, vol. 10, Article 1929, p. 1-13.

Alkim, et al., Microbial Cell Factries, 14: 127, 2015.

Attanatho et al., "Jet fuel range hydrocarbon synthesis through ethylene oligomerization over platelet Ni AISBA 15 catalyst", Apr. 2020, SN Applied Sciences (2020), 2:971, p. 1-12.

Li, et al."Engineering the Calvin-Benson-Bassham cycle and hydrogen utilization pathway of Ralstonia eutropha for improved autotrophic growth and polyhydroxybutyrate production", Microbial Cell Factories, 2020, 19:228.

Berndt and Schlegel, 1975, Arch. Microbiol. 103, 21-30.

Bertram et al., ArchMicrobiol_151, 551-557, 1989.

Cabano et al., 1997, Insect Biochem. Mol. Biol. 27: 499-505.

Chakraborty, et al., "PHA Productivity and Yield of Ralstonia eutropha When Intermittently or Continuously Fed a Mixture of Short Chain Fatty Acids", Hindawi Publishing Corporation.

Cheah, et al., "Biorefineries of carbon dioxide: From carbon capture and storage (CCS) to bioenergies production", Bioresource Technology 215 (2016), p. 346-356.

Chee, et al., "The Potential Application of Cupriavidus necator as Polyhydroxyalkanoates Producer and Single Cell Protein: A Review on Scientific, Cultural and Religious Perspectives", Applied Food Biotechnology, 2019, vol. 6, No. 1, p. 19-34.

Chen, et al."Overexpression of bacterial ethylene-forming enzyme gene in Trichoderma reesei enhanced the production of ethylene", International Journal of Biological Sciences 2010; 6(1), 96-106.

Chiba, Section 18: Diet Formulation and Common Feed Ingredients, Animal Nutrition Handbook, 3rd revision, pp. 575-633, 2014.

Chinn, "Recovery of Glycols, Sugars, and Related Multiple -OH Compounds from Dilute-Aqueous Solution by Regenerable Adsorption onto Activated Carbons", University of California Berkeley, 1999.

Dhale, et al., "Propylene glycol and ethylene glycol recovery from aqueous solution via reactive distillation" Chemical Engineering Science 59 (2004), 2881-2890.

Digiacomo, et al., "Ethylene-Producing Bacteria That Ripen Fruit" 2014 American Chemical Society, ACS Synthetic Biology, 2014, 3, 935-938.

Drake, Acetogenic Prokaryotes, In: The Prokaryotes, 3rd edition, p. 354, New York, NY, 2006.

Durall, et al., "Increased ethylene production by overexpressing phosphoenolpyruvate carboxylase in the cyanobacterium Synechocystis PCC 6803", Biotechnology for Biofuels (2020) 13:16, p. 1-13.

Ebrahim, et al., "COBRApy: CONstraints-Based Reconstruction and Analysis for Python", BMC Systems Biology 2013, 7:74, p. 1-6.

Eckert, et al., "Ethylene-forming enzyme and bioethylene production", Biotechnology for Biofuels 2014, 7:33, p. 1-11.

Gerich, et al., "Ethylene Production From *Ecoli*," May 2012, p. 1-24.

Green et al. (2007, Phytochemistry; 68:176-188).

Guerrero et al., "Ethylene Synthesis and Regulated Expression of Recombinant Protein in *Synechocystis* sp. PCC 6803", PLOS-ONE, Nov. 2012, vol. 7, Issue11, e50470, p. 1-11.

(56) References Cited

OTHER PUBLICATIONS

Heap et al., "A modular system for Clostridium shuttle plasmids" Journal of Microbiological Methods 78, 2009,p. 79-85.
Herbert_FEMSMicrobiolLett_103-110_2003.
Herdendorf, et al. "Functional Evaluation of Conserved Basic Residues in Human Phosphomevalonate Kinase" Biochemistry. Oct. 23, 2007; 46(42): 11780-11788.
Herzberger et al., Chem Rev., 116(4): 2170-2243 (2016).
Hungate, Methods in Microbiology, vol. 3B. Academic Press, 1969, 117-132.
Hunter et al., 2007, J. Biol. chem. 282: 21573-77.
Jahn, et al. "Protein allocation and utilization in the versatile chemolithoautotroph Cupriavidus necator", eLife 2021;0: e69019, p. 1-26.
Jennert, et al., "Gene transfer to Clostridium cellulolyticum ATCC 35319", Microbiology (2000), 146, 3071-3080.
Jensen, et al., "Optlang: An Algebraic Modeling Language for Mathematical Optimization", Journal of Open Source Software, 2(9), 139, 2017.
Julsing et al., Appl Microbiol Biotechnol, 75, 2007, 1377-84.
Kallio, et al., "Photoautotrophic production of renewable ethylene by engineered cyanobacteria: Steering the cell metabolism towards biotechnological use" Physiologia Plantarum. 2021;173:579-590.
Karim et al. Synthetic Biology 2020; 5(1): ysaa019.
Köpke et al., 2010, Proc. Nat. Sci. U.S.A. 107: 13087-92.
Köpke, et al.,"Biochemical production of biobutanol", Woodhead Publishing Limited, 2010, p. 221-257.
Köpke et al., 2011, Appl. Environ. Microbiol. 77:5467-75.
Köpke et al., 2011, Curr. Opin. Biotechnol. 22: 320-325.
Krepkiy et al. (2004, Protein Sci. 13: 1875-1881).
Kunasundari, et al."Revisiting the Single Cell Protein Application of Cupriavidus necator H16 and Recovering Bioplastic Granules Simultaneously", PLOS ONE, Oct. 2013, vol. 8 , Issue 10, e78528, p. 1-15.
Kuzuyama et al. (2000, J. Bacteriol. 182, 891-897).
Lange et al., 2000, PNAS, 97: 13172-77.
Leang, et al.,ApplEnvironMicrobiol, Nov. 2012, _1102-1109.
Lo et al.,"Acetogenic production of 3-Hydroxybutyrate using a native 3-Hydroxybutyryl-CoA Dehydrogenase", Frontiers in Microbiology, vol. 13, 2022, p. 1-12.
Ma et al., 2011, Metab. Engin., 13:588-597.
Madison, et al.,"Metabolic Engineering of Poly(3-Hydroxyalkanoates): From DNA to Plastic", Microbiology and Molecular Biology Reviews, Mar. 1999, vol. 63, No. 1, p. 21-53.
Maia, Proceedings of the Genetic and Evolutionary Computation Conference Companion on—GECCO ?7, New York, New York, ACM Press, 1661-1668, 2017.
Mates, et al., "Antioxidant Enzymes and Human Diseases", Clinical Biochemistry, 1999, vol. 32, No. 8, 595-603.
Mermelstein, et al.,Expression of cloned homologous fermentative genes in clostridium acetobutylicum ATCC 824, Nature Publishing Group, 1992, p. 190-195.
Miziorko, 2011, Arch Biochem Biophys, 505: 131-143.
Modica, et al.,"Toxicological Evaluation of Protein Powder Derived from Cupriavidus necator ", AIBMR Life Sciences Inc., 2023.
Pearcy, et al.,"A genome scale model of Cupriavidus necator for platform chemical production" Synthetic Biology Research Center, Jan. 2018, p. 1-26.
Pena-Francesch, et al.,"Squid-inspired tandem repeat proteins: Functional fibers and films", Frontiers in chemistry, 2019, vol. 7, article No. 69, pp. 1-16.
Pereira, Metab Eng, 34: 80-87, 2016.
Perez, Biotechnol Bioeng, 110:1066-1077, 2012.
Prasanna Tamarapu Parthasarathy, "Development of a Genetic Modification System in Clostridium scatologenes ATCC 25775 for Generation of Mutants", Masters Project Western Kentucky University, 2010, 1-42.
Raberg, et al., "A Closer Look on the Polyhydroxybutyrate- (PHB-) Negative Phenotype of Ralstonia eutropha PHB 4", May 2014, vol. 9, Issue 5, PLOS ONE.
Ragsdale, Biochim Biophys Acta, 1784: 1873-1898, 2008.
Ranaivoarisoa, "Towards sustainable bioplastic production using the photoautotrophic bacterium *Rhodopseudomonas palustris* TIE-1", Journal of Industrial Microbiology Biotechnology (2019), 46, 1401-1417.
Rodrigues, et al.,"Assessment of Polyhydroxyalkanoate Synthesis in Submerged Cultivation of Cupriavidus Necator and Burkholderia Cepacia Strains Using Soybean as Substrate" Brazilian Journal of Chemical Engineering, vol. 36, No. 01, pp. 73-83, Jan.-Mar. 2019.
Sambrook et al., "Molecular Cloning: A laboratory Manual", Cold Spring Harbour Laboratory Press, Cold Spring Harbour, 1989.
Zhao et al. (2011, Appl Microbiol Biotechnol, 90:1915-1922).
Schiel-Bengelsdorf and Durre, 2012, FEBS Letters: 10.1016/j.febslet. 2012.04.043.
Schmidt, Protein Expr Purif 92: 54-61, 2013.
Silver et al. (1991, Plant Physiol. 97: 1588-1591).
Smith et al., "Succinate inhibition of a-ketoglutarate-dependent enzymes in a yeast model of paraganglioma" Human Molecular Genetics 2007, vol. 16, No. 24, p. 3136-3148.
Stim-Herndon et al. (1995, Gene 154: 81-85).
Stratz, et al.,"Plasmid Transfer into the Homoacetogen Acetobacterium woodii by Electroporation and Conjugation", Applied Environmental Microbiology, Mar. 1994, p. 1033-1037.
Strittmatter, et al.,"Medium-Chain-Length Fatty Acid Catabolismin Cupriavidusnecator H16: Transcriptome Sequencing Reveals Differences from Long-Chain-Length Fatty Acid b-Oxidation and Involvement of Several Homologous Genes", Applied Environmental Microbiology, Jan. 2023, vol. 89, Issue 1, p. 1-20.
Tanner et al., *Clostridium ljungdahlii* sp. nov., an *Acetogenic* Species in Clostridial rRNA Homology Group I. Int J Syst Bacteriol 1993, 43: 232-236.
Tirado-Acevedo, Production of bioethanol from synthesis gas using Clostridium ljungdahlii, PhD thesis, North Carolina State University, 2010.
Torella, et al., "Efficient solar-to-fuels production from a hybrid microbial-water-splitting catalyst system", PNAS, Mar. 24, 2015, vol. 112 , No. 12, 2337-2342.
Trutko et al. (2005, Microbiology 74: 153-158).
Tyurin et al., 2012, J. Biotech Res. 4: 1-12.
Tyurin, et al. "Electrotransformation of Clostridium thermocellum", vol. 70, No. 2, Applied and Environmental Microbiology, Feb. 2004, p. 883-890.
Vajravel, et al., "Towards sustainable ethylene production with cyanobacterial artificial biofilms", Green Chemistry, 2020, 22, 6404-6414.
Vaud, et al. "Engineering improved ethylene production: Leveraging systems biology and adaptive laboratory evolution", Metabolic Engineering, vol. 67, Sep. 2021, pp. 308-320.
Weingart, et al., "Comparison of Ethylene Production by Pseudomonas syringae and Ralstonia solanacearum", 1999 The American Phytopathological Society, vol. 89, No. 5, p. 360-365.
Weisberg et al., Journal of Bacteriology, Jan. 1991, p. 693-703.
Wilkinson et al., "Carbon and Energy Storage in Bacteria", J. gen. Microbiol. (1963), 32, p. 171-176.
Williams et al., Conjugative plasmid transfer from *Escherichia coli* to Clostridium acetobutylicum, Journal of General Microbiology (1990), 136, 819-826.
Wilson, et al., "Bio-production of gaseous alkenes: ethylene, isoprene, isobutene", Biotechnology for Biofuels (2018) 11:234, p. 1-11.
Wolfe, 1971, Adv. Microb. Physiol., 6: 107-146.
Xiao et al., Ind Eng Chem Res. 54(22): 5862-5869 (2015).
Zaviel et al., "A quantitative evaluation of ethylene production in the recombinant cyanobacterium *Synechocystis* sp. PCC 6803 harboring the ethylene forming enzyme by membrane inlet mass spectrometry" BioresourceTechnology 202, 2016, 142-151.
Zaviel, et al., "A quantitative evaluation of ethylene production in the recombinant cyanobacterium *Synechocystis* sp. PCC 6803 harboring the ethylene-forming enzyme by membrane inlet mass spectrometry", Elsevier 2015.
Kupas et al. "Large scale analysis of protein-binding cavities using self-organizing maps and wavelet-based surface patches to describe

(56) References Cited

OTHER PUBLICATIONS functional properties, selectivity discrimination, and putative cross-reactivity" Proteins, vol. 71, Issue3, May 15, 2008, pp. 1288-1306.

Padmapriya, et al., "Purification and Characterization of Iron-Containing Superoxide Dismutase from Anabaena Variabilis Kutz ex Born. et Flah", Biomedical Pharmacology Journal, 2015.

Pena-Francesch, et al., Research Update: Programmable tandem repeat proteins inspired by squid ring teeth, APL Materials, Jan. 2018.

Pena-Francesch, et al., "Squid-Inspired Tandem Repeat Proteins: Functional Fibers and Films" Frontiers In Chemistry, vol. 7, Article69, Feb. 2019, 16 pages.

Pullmann, et al., "A modular two yeast species secretion system for the production and preparative application of unspecific peroxygenases", Commuications Biology 2021, 20 pages.

Zhao, et al., "Production of a Novel Superoxide Dismutase by Escherichia coli and Pichia pastoris and Analysis of the Thermal Stability of the Enzyme", Frontiers In Nutrition, Mar. 2022, vol. 9, 10 pages.

Hiew et al., "Squid Sucker Ring Teeth: Multiscale Structure—Property Relationships, Sequencing, and Protein Engineering of a Thermoplastic Biopolymer", ACS Biomaterials Science And Engineering, vol. 3, Issue 5.

Zeinali, et al., "Sources of Marine Superoxide Dismutases: Characteristics and applications", International Journal of Biological Macromolecules, vol. 79, Aug. 2015, p. 627-637.

Bafana, et al., "Superoxide dismutase: an industrial perspective", Critical Reviews Biotechnology, vol. 31, Issue 1, 2011, pp. 65-76.

Peterson, et al., "Extracellular Superoxide Dismutase (EC-SOD) Binds to Type I Collagen and Protects Against Oxidative Fragmentation", The Journal of Biological Chemistry, vol. 279, No. 14, p. 13705-13710.

Drug Bank, https://go.drugbank.com/bio_entities/BE0004143, retrieved Oct. 18, 2024.) (Year: 2024).

Genbank1, (+)-alpha-pinene synthase, https://www.ncbi.nlm.nih.gov/protein/75146889?sat=51 &satkey=2226343, revision Feb. 23, 2022, retrieved Sep. 23 2024 (Year: 2023).

Genbank2, (E)-alpha-bisabolene synthase, https://www.ncbi.nlm.nih.gov/protein/62511183? sat=58&satkey=109590006, revision Feb. 22, 2023, retrieved Sep. 23 2024. (Year: 2023).

Sohn, et al., Chemoautotroph Cupriavidus necator; Bioresource Technology 340, 2021, pp. 1-14. (Year: 2021).

Sheng, et al., "Superoxide Dismutases and Superoxide Reductases", Chem. Rev. 2014, vol. 114, p. 3854-3918.

Brenda Enzyme Database, 2024, pp1.

Buck, et, al,"Anion-Mediated Effects on the Size and Mechanical Properties of Enzymatically Crosslinked Suckerin Hydrogels", Macromolecular Bioscience 2019, vol. 19.

Bellini, et al., "Poly (3-hydroxybutyrate) biosynthesis by Cupriavidus necator: a review on waste substrates utilization for a circular economy approach." Bioresource Technology Reports 17 (2022).

International Search Report and Written Opinion issued in International Application No. PCT/US2024/034921, dated Oct. 10, 2024, 13 pages.

Beck, et al., "Efficient Production of Active Human Manganese Superoxide Dismutase In Escherichia Coli", Nature Biotechnology, vol. 6, Aug. 1988, pp. 930-935.

Chen, et al., "Construction of Cupriavidus Necator displayed with a superoxide dismutase for enhanced growth in bioelectrochemical systems" Bioresources & Bioprocessing, Jun. 28, 2023.

Ding, et al., "Biomimetic Production of Silk-Like Recombinant Squid Sucker Ring Teeth Proteins", Biomacromolecules, 2014, vol. 15, pp. 3278-3289.

Dong, et al., "Construction and potential application of bacterial superoxide dismutase expressed in Bacillus subtilis against mycotoxins", PLOSONE 16(11), Nov. 16, 2021.

Gopal, et al., "Industrial Production of Superoxide Dismutase (Sod): A Mini Review", Journal of Probiotics And Health, vol. 5, Issue 3, 2017.

Guerette, et al., "Nanoconfined B -sheets Mechanically Reinforce the Supra-Biomolecular Network of Robust Squid Sucker Ring Teeth" ACS Nano, vol. 8, Issue 7.

Hakopian, et al., "The air-inactivation of formate dehydrogenase FdsDABG from Cupriavidus Necator", Journal of Inorganic Biochemistry, vol. 231, Jun. 2022.

Hershewe, et al., "Characterizing and Controlling Nanoscale Self-Assembly of Suckerin-12", ACS Synthetic Biology 2020, vol. 9, Issue 12, p. 3388-3399.

Hu, et al., "Protein-based composite materials", vol. 15, Issue 5, Materials Today, May 2012, p. 208-215.

Jung, et al., "Molecular tandem repeat strategy for elucidating mechanical properties of high-strength proteins", PNAS, vol. 113, Issue 23, Jun. 7, 2016, p. 6478-6483.

\* cited by examiner

MICROORGANISMS AND METHODS FOR THE CONTINUOUS CO-PRODUCTION OF HIGH-VALUE, SPECIALIZED PROTEINS AND CHEMICAL PRODUCTS FROM C1-substrates

CROSS REFERENCE TO RELATED APPLICATIONS

This application claims the benefit of U.S. Provisional Patent Application Nos. 63/366,757, filed Jun. 21, 2022, and 63/497,045, filed Apr. 19, 2023, the entirety of which is incorporated herein by reference.

REFERENCE TO A SEQUENCE LISTING

The application contains a Sequence Listing which has been submitted electronically in ST.26 Sequence listing XML format and is hereby incorporated by reference in its entirety. Said ST.26 Sequence listing XML, created on May 31, 2023, is named LT244US1-Sequences.xml and is 10,681 bytes in size.

FIELD

The present disclosure relates to genetically engineered microorganisms and methods for the continuous co-production of amino acids, high-value, specialized proteins, microbial biomass, chemicals, or any combination thereof by microbial fermentation, particularly by microbial fermentation of a gaseous substrate.

BACKGROUND

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and 2,3-butanediol. Efficient co-production of such chemical products and heterologous proteins may be limited, however, by slow microbial growth, limited gas uptake, sensitivity to toxins, or diversion of carbon substrates into undesired by-products. Additionally, there has been a growing interest to efficiently produce high-value, specialized proteins. With a constantly adjusting market, the value of the products produced by the gas fermentation process varies. When the value of the products produced by the gas fermentation are high in comparison with the cost of producing such products, it is advantageous to increase the production rate of the fermentation process. Further, most renewable energy sources are intermittent, not transportable, and largely dependent on the meteorological and geographical conditions. By increasing the production rate of the fermentation process at times when the market value of such specialized protein products is high relative to the cost of producing such products, the economics of the fermentation process may be optimized with co-production. There is accordingly an ongoing and unmet need to develop novel high value, specialized protein products that can be produced easily from renewable resources, and which would offer a broad array of useful applications. There also remains a need for genetically engineered microorganisms having improved characteristics for the continuous co-production of chemicals, proteins, biomass, or any combination thereof by microbial fermentation of a gaseous substrate.

SUMMARY

It is against the above background that the present disclosure provides certain advantages and advancements over the prior art.

Although this disclosure disclosed herein is not limited to specific advantages or functionalities, the disclosure provides a method and a genetically engineered microorganism capable of co-producing at least one exogenous gene product and at least one chemical product from a gaseous substrate, the microorganism comprising an exogenous nucleic acid encoding the at least one protein having tandem repeats and an exogenous nucleic acid encoding the at least one secreted chemical product.

In some aspects of the method disclosed herein, the method is directed to a process for continuous co-production of at least one chemical product and at least one exogenous gene product comprising:
a) providing a continuous bioreactor;
b) introducing to the bioreactor a recombinant C1-fixing microorganism capable of co-producing at least one chemical product and at least one exogenous gene product, a gaseous substrate comprising one or more of CO, $CO_2$, and $H_2$, and a liquid growth medium;
c) continuously culturing the recombinant C1-fixing microorganism thereby generating a gas fermentation broth comprising 1) the at least one chemical product, 2) the at least one exogenous gene product, and 3) microbial biomass;
d) continuously removing a portion of the gas fermentation broth in a first stream;
e) continuously removing the at least one chemical product in a second stream; and
f) continuously recovering the at least one exogenous gene product from the microbial biomass from the first stream.

In some aspects of the method disclosed herein, the method is directed to a method for the continuous co-production of at least one targeted chemical product and at least one exogenous gene product, the method comprising:
a) culturing a recombinant C1-fixing microorganism capable of co-production of at least one targeted chemical product and at least one exogenous gene product in the presence of a gaseous substrate comprising one or more of CO, $CO_2$, and $H_2$, wherein the culturing is a continuous fermentation process; and wherein the substrate and liquid nutrient medium of the culture are non-coalescing.

Another aspect is directed to a method for continuous co-production of at least one targeted chemical product and at least one exogenous gene product, the method comprising: a) culturing in a state of a continuous gas fermentation process, a recombinant C1-fixing microorganism capable of co-production of at least one targeted chemical product and at least one exogenous gene product in a fermentation broth comprising the microorganism, a gaseous substrate comprising one or more of CO, $CO_2$, and $H_2$, and a liquid growth medium, wherein the fermentation broth comprises an equilibrium surface tension of from about 30 to about 40 mN/m.

One aspect is directed to a method for continuous co-production of at least one targeted chemical product and at least one exogenous gene product, the method comprising: a) culturing in a bioreactor, a recombinant C1-fixing microorganism capable of co-production of at least one targeted chemical product and at least one exogenous gene product having a unit value in the presence of a gaseous substrate comprising one or more of CO, $CO_2$, and $H_2$, and a liquid growth medium; and recovering the at least one targeted chemical product and the at least one exogenous gene product wherein the at least one exogenous gene product is recovered in an amount from about 0.1% to about 1% grams/dry cell weight/day of the at least one exogenous gene product produced.

The method of an embodiment, further comprising an initial stage of gas fermentation wherein the initial surface tension of the broth is from about 60 to about 72 mN/m.

The method of an embodiment, wherein the exogenous gene product has a high market value.

The method of an embodiment, wherein the exogenous gene product is a high-value, specialized protein.

The method of an embodiment, wherein the exogenous gene product is an antioxidant or an antioxidant enzyme.

The method of an embodiment, wherein the antioxidant is selected from catalase, glutathione peroxidase, vitamin C, vitamin E, beta-carotene, carotenoids, flavonoids, superoxide dismutase, ascorbate peroxidase, or any combination thereof.

The method of an embodiment, wherein the antioxidant enzyme is superoxide dismutase.

The method of an embodiment, wherein the superoxide dismutase is selected from SOD006, SOD007, SOD009, and SOD010.

The method of an embodiment, wherein the at least one exogenous gene product is squid ring teeth (SRT) protein and the at least one chemical product is ethylene.

The method of an embodiment, wherein the at least one chemical product is ethylene.

The method of an embodiment, further comprising separating the microbial biomass from the first stream before recovering the heterologous protein.

One embodiment is directed to a method for continuous co-production of at least one targeted chemical product and at least one exogenous gene product, the method comprising: a) culturing, in a bioreactor, a recombinant C1-fixing microorganism capable of co-production of at least one targeted chemical product and at least one exogenous gene product in the presence of a gaseous substrate comprising one or more of CO, $CO_2$, and $H_2$, and a liquid growth medium; b) generating microbial biomass having a unit value, at least one targeted chemical product, and at least one exogenous gene product having a unit value, wherein the unit value of the exogenous gene product is greater than the unit value of the microbial biomass; and c) recovering the at least one exogenous gene product in an amount of at least 15% of a sum value of the unit value of the exogenous gene product and the unit value of the microbial biomass.

The method of an embodiment, wherein recovering of step c) of the at least one exogenous gene product is in an amount of at least 1% of the sum value.

The method of an embodiment, wherein the high-value, specialized protein is selected from ubiquinone, coenzyme Q10, copper/zinc and manganese-dependent superoxide dismutase, iron-dependent catalase, selenium-dependent glutathione peroxidase, albumin, ceruloplasmin, metallothionein, ferritin, myoglobin, transferrin, haptoglobins, ceruloplasmin, heat shock proteins, iron-dependent superoxide dismutase, nickel-dependent superoxide dismutase, or any combination thereof.

The method of an embodiment, wherein the catalases are selected from heme-containing catalases and non-heme manganese catalases.

The method of an embodiment, wherein the at least one chemical product is selected from 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, ketoadipic acid, 1,3-hexanediol, 3-methyl-2-butanol, 2-buten-1-ol, isovalerate, isoamyl alcohol, monoethylene glycol, or any combination thereof.

The method of an embodiment, further comprising the recombinant microorganism comprising a disruptive mutation in one or more genes.

The method of an embodiment, wherein the recombinant microorganism comprises a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides, Cupriavidus necator* and *Thermoanaerobacter kivui*.

The method of an embodiment, wherein the chemical product is one or more of ethylene, ethanol, acetone, isopropanol, or any combination thereof.

The method of an embodiment, further comprising a microbial biomass and at least one excipient.

The method of an embodiment, wherein the microbial biomass is suitable as animal feed.

The method of an embodiment, wherein the at least one exogenous gene product is superoxide dismutase and the at least one chemical product is ethylene.

In some aspects of the microorganism disclosed herein, the microorganism produces a commodity chemical product, a tandem repeat protein product, microbial biomass, single cell protein (SCP), one or more intermediates, or any combination thereof.

In some aspects of the microorganism disclosed herein, the microorganism produces a exogenous gene product. In one embodiment, the exogenous gene product comprises a exogenous nucleic acid encoding at least one protein having tandem repeats.

In some aspects of the microorganism disclosed herein, the microorganism comprises a genetically engineered microorganism capable of co-producing at least one heterologous protein and at least one secreted chemical product from a gaseous substrate, the microorganism comprising a heterologous nucleic acid encoding the at least one protein having tandem repeats and a heterologous nucleic acid encoding the at least one secreted chemical product, wherein the microorganism is a C1-fixing bacteria.

In some aspects of the microorganism disclosed herein, the microorganism comprises a genetically engineered C1-fixing microorganism capable of co-producing an heterologous protein and a chemical product from a gaseous substrate, the microorganism comprising a heterologous nucleic acid encoding the at least one heterologous protein having one or more tandem repeats and a heterologous nucleic acid encoding the at least one chemical product, wherein the microorganism is capable of accumulating the at least one heterologous protein in the cell and secreting the at least one chemical product from the cell.

In some aspects of the microorganism disclosed herein, the microorganism comprises one or more heterologous enzymes are derived from a genus selected from the group consisting of *Bacillus, Clostridium, Cupriavidus, Escherichia, Gluconobacter, Hyphomicrobium, Lysinibacillus, Paenibacillus, Pseudomonas, Sedimenticola, Sporosarcina, Streptomyces, Thermithiobacillus, Thermotoga*, and *Zea*.

In some aspects of the microorganism disclosed herein, the microorganism comprises a genetically engineered C1-fixing microorganism capable of co-producing at least one heterologous functional protein and at least one chemical product having two or more carbons from a gaseous substrate, the microorganism comprising a heterologous nucleic acid encoding at least one protein having tandem repeats and a heterologous nucleic acid encoding at least one secreted chemical product.

In some aspects of the microorganism disclosed herein, the microorganism comprises a genetically engineered C1-fixing microorganism capable of co-producing at least one heterologous functional protein and at least one chemical product having two or more carbons from a gaseous substrate, the microorganism comprising a heterologous nucleic acid encoding a group of genes comprising at least one protein having tandem repeats and at least one secreted chemical product.

In some aspects of the microorganism disclosed herein, the microorganism comprises a genetically engineered C1-fixing microorganism capable of co-producing at least one heterologous protein and at least one chemical product from a gaseous substrate, the microorganism comprising:
a) a heterologous nucleic acid encoding at least one heterologous protein having one or more tandem repeats; and
b) a heterologous nucleic acid encoding at least one chemical having two or more carbons, wherein the microorganism is capable of accumulating the at least one heterologous protein in the cell and secreting the at least one chemical product from the cell.

One aspect comprises a method of co-producing at least one heterologous protein and at least one chemical product by culturing the genetically engineered C1-fixing. microorganism in the presence of a gaseous substrate comprising one or more of CO, $CO_2$, and $H_2$, wherein the culturing is a continuous fermentation process.

One aspect comprises a method, wherein the gaseous substrate comprises a C1-carbon source comprising one or more of CO, $CO_2$, and $H_2$.

One aspect comprises a method, wherein the gaseous substrate comprises syngas or industrial waste gas.

One aspect comprises a method of co-producing at least one heterologous protein and at least one chemical product by culturing the genetically engineered C1-fixing, wherein the product is one or more of acetone and isopropanol.

In some aspects of the microorganism disclosed herein, the microorganism comprises a genetically engineered C1-fixing microorganism, wherein the at least one heterologous protein having one or more tandem repeats is selected from collagen, silk, elastin, keratin, resilin, titin, squid ring teeth (SRT) protein, or any combination thereof.

In some aspects of the microorganism disclosed herein, the microorganism is a member of a genus selected from the group consisting of *Acetobacterium, Alkalibaculum, Blautia, Butyribacterium, Clostridium, Cupriavidus, Eubacterium, Moorella, Oxobacter, Ralstonia, Sporomusa*, and *Thermoanaerobacter*.

In some aspects of the microorganism disclosed herein, the microorganism is derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Cupriavidus necator, Eubacterium limosum, Moorella thermautotrophica, Moorella thermoacetica, Oxobacter pfennigii, Ralstonia eutropha, Sporomusa ovata, Sporomusa silvacetica, Sporomusa sphaeroides*, and *Thermoanaerobacter kiuvi*.

In some aspects of the microorganism disclosed herein, the microorganism is derived from a parental bacterium selected from the group consisting of *Clostridium autoethanogenum, Clostridium ljungdahlii*, and *Clostridium ragsdalei*.

In some aspects of the microorganism disclosed herein, the microorganism is derived from a parental bacterium selected from the group consisting of *Cupriavidus necator*.

The genetically engineered C1-fixing microorganism, wherein the at least one heterologous protein having one or more tandem repeats is selected from silk or SRT protein.

In some aspects of the microorganism disclosed herein, where the gas fermentation product is selected from an alcohol, an acid, a diacid, an alkene, a terpene, an isoprene, and alkyne, or any combination thereof.

In some aspects of the microorganism disclosed herein, where the at least one secreted chemical product is selected from the group 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, keto-adipic acid, 1,3-hexanediol, 3-methyl-2-butanol, 2-buten-1-ol, isovalerate, isoamyl alcohol, or monoethylene glycol.

In some aspects of the microorganism disclosed herein, the microorganism further comprising a disruptive mutation in one or more genes.

The disclosure further provides the genetically engineered C1-fixing microorganism, further comprising a microbial biomass and at least one excipient.

The disclosure further provides the genetically engineered C1-fixing microorganism, wherein the microbial biomass is suitable as animal feed.

The disclosure further provides the genetically engineered C1-fixing microorganism, wherein the animal feed is suitable for feeding to one or more of beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents.

The disclosure further provides the genetically engineered C1-fixing microorganism, wherein the microorganism is suitable as a single cell protein (SCP).

The disclosure further provides the genetically engineered C1-fixing microorganism, wherein the microorganism is suitable as a cell-free protein synthesis (CFPS) platform.

The disclosure further provides the genetically engineered C1-fixing microorganism, wherein the at least one secreted chemical product is native to the microorganism.

In some aspects of the method disclosed herein, the substrate comprises one or more of CO, $CO_2$, and $H_2$.

In some aspects of the method disclosed herein, at least a portion of the substrate is industrial waste gas, industrial off gas, or syngas.

In some embodiments, both anaerobic and aerobic gases can be used to feed separate cultures (e.g., an anaerobic culture and an aerobic culture) in two or more different bioreactors that are both integrated into the same process stream.

In some embodiments, the disclosure provides a method for storing energy in the form of a biopolymer comprising intermittently processing at least a portion of electric energy generated from a renewable and/or non-renewable energy source in an electrolysis process to produce at least $H_2$, $O_2$ or CO; intermittently passing at least one of $H_2$, $O_2$, or CO from the electrolysis process to a bioreactor containing a culture comprising a liquid nutrient medium and a microorganism capable of producing a biopolymer; and fermenting the culture.

In an embodiment, the disclosure also provides a system for storing energy in the form of biopolymer comprising an electrolysis process in intermittent fluid communication with a renewable and/or non-renewable energy source for producing at least one of $H_2$, $O_2$, or CO; an industrial plant for producing at least C1 feedstock; a bioreactor, in intermittent fluid communication with the electrolysis process and/or in continuous fluid communication with the industrial plant, comprising a reaction vessel suitable for intermittently growing, fermenting, and/or culturing and housing a microorganism capable of producing a biopolymer.

In some embodiments, the disclosure provides a method for improving the performance and/or the economics of a fermentation process, the fermentation process defining a bioreactor containing a bacterial culture in a liquid nutrient medium, wherein the method comprises passing a C1 feedstock comprising one or both of CO and $CO_2$ from an industrial process to the bioreactor, wherein the C1 feedstock has a cost per unit, intermittently passing at least one of $H_2$, $O_2$, or CO from the electrolysis process to the bioreactor, wherein the electrolysis process has a cost per unit, and fermenting the culture to produce one or more fermentation products, wherein each of the one or more fermentation products has a value per unit. In certain instances, multiple electrolysis processes are utilized in order to provide one or all of CO, $CO_2$, and $H_2$ to the bioreactor.

In another embodiment, the local power grid provides electricity intermittently passed as electrical energy produced by power based on availability of electrical power or the availability of electricity below a threshold price, where power prices fall as demand falls, or as set by the local power grid.

In an embodiment, the disclosure can be operated intermittently by storing energy in the form of a biopolymer, where product conversion can be intermittent during periods when an electricity grid is oversupplied with electricity, or idle when electricity is scarce or power is in demand. The disclosure provides a process that is capable of being fine-tuned to assist with balancing an electrical power grid system by storing energy in the form of a biopolymer.

In one embodiment an autotrophic microorganism intermittently consumes, in part or entirely, the energy provided by the availability of power.

In one embodiment, the systems disclosed herein relate to generating fine bubbles and may include a vessel containing a liquid, a plate comprising a plurality of orifices positioned in an upper portion of the vessel and configured to accelerate at least a portion of the liquid in the vessel, and at least one sparger positioned within the vessel with a surface of the sparger positioned from about 50 mm to about 300 mm, 500 mm, or 1000 mm from a bottom of the plate. The sparger may be configured to inject bubbles into the liquid. In some examples, the sparger may be positioned within the vessel to create a first zone for the bubbles to rise within the vessel, and to create a second zone for the accelerated liquid to break the bubbles into fine bubbles and for fluid to flow through the vessel. The fluid may include the accelerated portion of the liquid and fine bubbles. In still other examples, the superficial velocity of the gas phase in the vessel may be at least 30 mm/s. The sparger may be a sintered sparger or an orifice sparger. The thickness of the plate may be about 1 mm to about 25 mm. The accelerated liquid may have a velocity of about 8000 mm/s to about 17000 mm/s. In other examples, the accelerated liquid may have a velocity of about 12000 mm/s to about 17000 mm/s. In some examples, the bubbles injected into the liquid from the sparger may have a diameter of about 2 mm to about 20 mm. In another example, the bubbles injected into the liquid from the sparger may have a diameter of about 5 mm to about 15 mm, or from about 7 mm to about 13 mm. The fine bubbles may have a diameter of about 0.1 mm to about 5 mm, or about 0.2 mm to about 1.5 mm. The plurality of orifices may also be configured to accelerate at least 90% of the liquid in the vessel.

In another embodiment, the methods disclosed herein relate to generating fine bubbles that may include sparging gas into a vessel containing a liquid via at least one sparger positioned within the vessel and configured to inject bubbles into the liquid and accelerating a portion of the liquid in the vessel via a perforated plate positioned in an upper portion of the vessel, in which the liquid may be accelerated from the plate to break the bubbles into fine bubbles. In some examples, a superficial velocity of the gas phase in the vessel may be at least 30 mm/s. In other examples, the superficial velocity of the gas phase in the vessel may be from about 30 mm/s to about 80 mm/s. The sparger may be a sintered sparger or an orifice sparger. The liquid may be accelerated from the perforated plate at a velocity of about 8000 mm/s to about 17000 mm/s. In some examples, the liquid may be accelerated from the perforated plate at a velocity of about 12000 mm/s to about 17000 mm/s. The bubbles injected into the liquid from the sparger may have a diameter of about 2 mm to about 20 mm, or from greater than 5 mm to about 15 mm, or from about 7 mm to about 13 mm. Often the bubbles injected into the liquid from the sparger are not spherical. The injected bubbles may be referred to as coarse bubbles. In contrast, the fine bubbles may have a diameter of about 0.1 mm to about 5 mm, or about 0.2 mm to about 1.5 mm. The fine bubbles are typically spherical. The liquid stream may be introduced at a location proximate to the plate. The sparger may be positioned perpendicular or parallel to the plate, and a top or side surface of the sparger may be positioned from about 50 mm to about 300 mm, 500 mm, or 1000 mm from a bottom of the plate.

In yet another embodiment, the systems disclosed herein relate to a bioreactor that may include a vessel containing a liquid growth medium, a plate that may include a plurality of orifices positioned in an upper portion of the vessel and configured to accelerate at least a portion of the liquid growth medium in the vessel, a substrate that may include at least one C1 carbon source, at least one sparger positioned within the vessel with a surface of the sparger that may be positioned from about 50 mm to about 300 mm, 500 mm, or 1000 mm from a bottom of the plate and the sparger configured to inject substrate bubbles into the liquid growth medium. The sparger positioned within the vessel may create a first zone for the substrate bubbles to rise within the vessel, and a second zone for the accelerated liquid growth medium to break the substrate bubbles into substrate fine bubbles, and for fluid to flow through the vessel. The fluid may have the accelerated portion of the liquid growth medium and may have the substrate fine bubbles, and a culture of at least one microorganism in the liquid growth medium. The culture of at least one microorganism may anaerobically ferment the substrate to produce at least one fermentation product.

In still another embodiment, the methods disclosed herein relate to generating substrate fine bubbles in a bioreactor and may include sparging substrate bubbles of at least one C1 carbon source into a vessel containing a liquid growth medium via at least one sparger positioned within the vessel and accelerating a portion of the liquid growth medium in the vessel via a perforated plate positioned in an upper portion of the vessel. The liquid growth medium accelerated from the plate may break the substrate bubbles into substrate fine bubbles. A superficial velocity of the gas phase in the vessel may be at least 30 mm/s. A culture of at least one microorganism may be included in the liquid growth medium and may anaerobically ferment the substrate to produce at least one fermentation product.

These and other features and advantages of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

These and other aspects of the present disclosure, which should be considered in all its novel aspects, will become apparent from the following description, which is given by way of example only, with reference to the accompanying figures, in which:

FIG. 2A: Ethanol production and SRT012 protein content per biomass relative to day 5 (reactor turned continuous) analyzed by HPLC and comparative Western blot, respectively;

FIG. 2B: Biomass and metabolite profile analyzed by HPLC; FIG. 2C: gas production profile analyzed by GC-TCD (negative=uptake).

FIG. 3A: Ethanol production and SRT008 protein content per biomass relative to day 0 analyzed by HPLC and comparative Western blot, respectively; FIG. 3B: Biomass and metabolite profile analyzed by HPLC; FIG. 3C: gas production profile analyzed by GC-TCD (negative=uptake).

FIG. 4A: Ethanol and SRT012 protein content per biomass relative to day 0 analyzed by HPLC and comparative Western blot, respectively. The last data point for protein content per biomass was taken after gas shutoff; FIG. 4B: Biomass and metabolite profile analyzed by HPLC; FIG. 4C: gas production profile analyzed by GC-TCD (negative=uptake).

FIG. 5A: Ethanol and SRT008 protein content per biomass relative to day 0 analyzed by HPLC and comparative Western blot, respectively; FIG. 5B: Biomass and metabolite profile analyzed by HPLC; FIG. 5C: gas production profile analyzed by GC-TCD (negative=uptake).

FIG. 6A: Ethanol and SRT012 protein content per biomass relative to day 0 analyzed by HPLC and comparative Western blot, respectively; FIG. 6B: Biomass and metabolite profile analyzed by HPLC; FIG. 6C: gas production profile analyzed by GC-TCD (negative=uptake).

DETAILED DESCRIPTION

Figure 1:
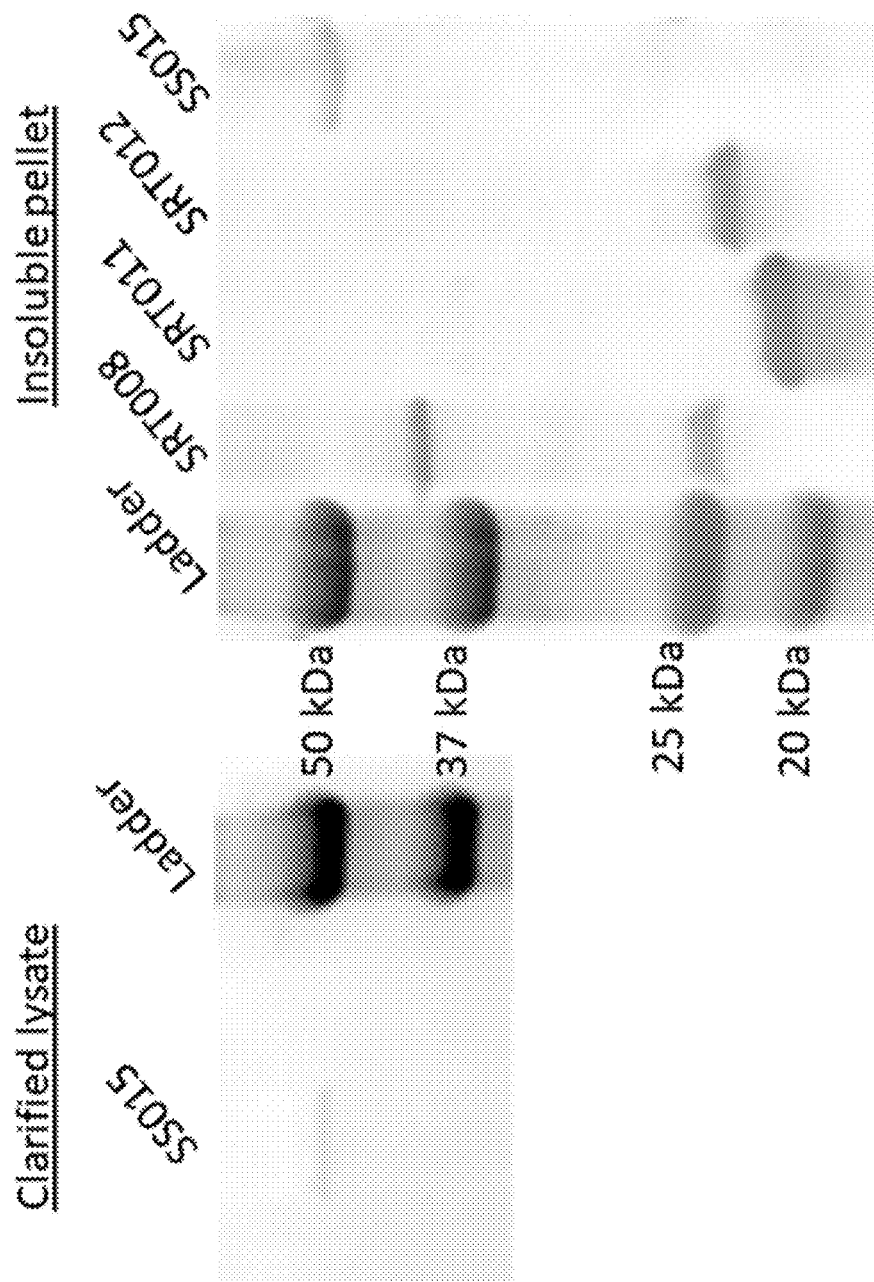
FIG. 1 shows the expression of tandem repeat proteins (Table 2) in *C. autoethanogenum* via Western blot. Production of tandem repeat proteins was evaluated by Western blot analysis using anti-Strep tag antibodies. Cultures were lysed and clarified; the clarified lysate and insoluble pellet (resuspended in 5 M urea) were analyzed separately for protein content. Samples were run on Tris-glycine SDS-PAGE, transferred to nitrocellulose membrane, and probed with anti-Strep tag antibody conjugated to alkaline phosphatase for visualization. Protein of the expected size was observed in the insoluble pellet for SRT008, SRT011, SRT012, and SS015. In addition, SS015 was observed in the clarified lysate.

The following description of embodiments is given in general terms. The disclosure is further elucidated from the disclosure given under the heading "Examples" herein below, which provides experimental data supporting the disclosure, specific examples of various aspects of the disclosure, and means of performing the disclosure.

The inventors have surprisingly been able to engineer a C1-fixing microorganism to co-produce a protein, a chemical or a precursor of the chemical, and microbial biomass by fermentation of a substrate comprising CO and/or $CO_2$.

Unless otherwise defined, the following terms as used throughout this specification are defined as follows:

The disclosure provides microorganisms for the biological co-production of proteins, chemicals, and microbial biomass. A "microorganism" is a microscopic organism, especially a bacterium, archaeon, virus, or fungus. In an embodiment, the microorganism of the disclosure is a bacterium.

The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility. The microorganisms of the disclosure are non-naturally occurring.

The terms "genetic modification," "genetic alteration," or "genetic engineering" broadly refer to manipulation of the genome or nucleic acids of a microorganism by the hand of man. Likewise, the terms "genetically modified," "genetically altered," or "genetically engineered" refers to a microorganism containing such a genetic modification, genetic alteration, or genetic engineering. These terms may be used to differentiate a lab-generated microorganism from a naturally-occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization. The microorganisms of the disclosure are genetically engineered.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. The microorganisms of the disclosure are generally recombinant.

"Wild type" refers to the typical form of an organism, strain, gene, or characteristic as it occurs in nature, as distinguished from mutant or variant forms.

"Endogenous" refers to a nucleic acid or protein that is present or expressed in the wild-type or parental microorganism from which the microorganism of the disclosure is derived. For example, an endogenous gene is a gene that is natively present in the wild-type or parental microorganism from which the microorganism of the disclosure is derived. In one embodiment, the expression of an endogenous gene may be controlled by an exogenous regulatory element, such as an exogenous promoter.

"Exogenous" refers to a nucleic acid or protein that originates outside the microorganism of the disclosure. For example, an exogenous gene or enzyme may be artificially or recombinantly created and introduced to or expressed in the microorganism of the disclosure. An exogenous gene or enzyme may also be isolated from a heterologous microorganism and introduced to or expressed in the microorganism of the disclosure. Exogenous nucleic acids may be adapted to integrate into the genome of the microorganism of the disclosure or to remain in an extra-chromosomal state in the microorganism of the disclosure, for example, in a plasmid.

"Heterologous" refers to a nucleic acid or protein that is not present in the wild-type or parental microorganism from which the microorganism of the disclosure is derived. For example, a heterologous gene or enzyme may be derived from a different strain or species and introduced to or expressed in the microorganism of the disclosure. The heterologous gene or enzyme may be introduced to or expressed in the microorganism of the disclosure in the form in which it occurs in the different strain or species. Alternatively, the heterologous gene or enzyme may be modified in some way, e.g., by codon-optimizing it for expression in the microorganism of the disclosure or by engineering it to alter function, such as to reverse the direction of enzyme activity or to alter substrate specificity.

In particular, a heterologous nucleic acid or protein expressed in the microorganism described herein may be derived from *Bacillus, Clostridium, Cupriavidus, Escherichia, Gluconobacter, Hyphomicrobium, Lysinibacillus, Paenibacillus, Pseudomonas, Sedimenticola, Sporosarcina, Streptomyces, Thermithiobacillus, Thermotoga, Zea, Klebsiella, Mycobacterium, Salmonella, Mycobacteroides, Staphylococcus, Burkholderia, Listeria, Acinetobacter, Shigella, Neisseria, Bordetella, Streptococcus, Enterobacter, Vibrio, Legionella, Xanthomonas, Serratia, Cronobacter, Cupriavidus, Helicobacter, Yersinia, Cutibacterium, Francisella, Pectobacterium, Arcobacter, Lactobacillus, Shewanella, Erwinia, Sulfurospirillum, Peptococcaceae, Thermococcus, Saccharomyces, Pyrococcus, Glycine, Homo, Ralstonia, Brevibacterium, Methylobacterium, Geobacillus, bos, gallus, Anaerococcus, Xenopus, Amblyrhynchus, rattus, mus, sus, Rhodococcus, Rhizobium, Megasphaera, Mesorhizobium, Peptococcus, Agrobacterium, Campylobacter, Acetobacterium, Alkalibaculum, Blautia, Butyribacterium, Eubacterium, Moorella, Oxobacter, Sporomusa, Thermoanaerobacter, Schizosaccharomyces, Paenibacillus, Fictibacillus, Lysinibacillus, Ornithinibacillus, Halobacillus, Kurthia, Lentibacillus, Anoxybacillus, Solibacillus, Virgibacillus, Alicyclobacillus, Sporosarcina, Salimicrobium, Sporosarcina, Planococcus, Corynebacterium, Thermaerobacter, Sulfobacillus,* or *Symbiobacterium.*

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products."

The terms "exogenous gene product" are used herein to refer to a protein molecule that is the product of the expression of an exogenous gene.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, by disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

The term "copolymer" is a composition comprising two or more species of monomers are linked in the same polymer chain of the disclosure.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the disclosure compared to the wild-type or parental microorganism from which the microorganism of the disclosure is derived. In one embodiment, the mutation may be a deletion, insertion, or substitution in a gene encoding an enzyme. In another embodiment, the mutation may be a deletion, insertion, or substitution of one or more amino acids in an enzyme.

"Disrupted gene" refers to a gene that has been modified in some way to reduce or eliminate expression of the gene, regulatory activity of the gene, or activity of an encoded protein or enzyme. The disruption may partially inactivate, fully inactivate, or delete the gene or enzyme. The disruption may be a knockout (KO) mutation that fully eliminates the expression or activity of a gene, protein, or enzyme. The disruption may also be a knock-down that reduces, but does not entirely eliminate, the expression or activity of a gene, protein, or enzyme. The disruption may be anything that reduces, prevents, or blocks the biosynthesis of a product produced by an enzyme. The disruption may include, for example, a mutation in a gene encoding a protein or enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, RNAi, TALEN, siRNA, CRISPR, or CRISPRi) or protein which inhibits the expression of a protein or enzyme. The disruption may be introduced using any method known in the art. For the purposes of the present disclosure, disruptions are laboratory-generated, not naturally occurring.

A "parental microorganism" is a microorganism used to generate a microorganism of the disclosure. The parental microorganism may be a naturally-occurring microorganism (i.e., a wild-type microorganism) or a microorganism that has been previously modified (i.e., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism.

The microorganism of the disclosure may be derived from essentially any parental microorganism. In one embodiment, the microorganism of the disclosure may be derived from a parental microorganism selected from the group consisting of *Clostridium acetobutylicum, Clostridium beijerinckii, Escherichia coli,* and *Saccharomyces cerevisiae.* In other embodiments, the microorganism is derived from a parental microorganism selected from the group consisting of *Acetobacterium woodii, Alkalibaculum bacchii, Blautia product, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kivui.* In an embodiment, the parental microorganism is *Clostridium autoethanogenum, Clostridium ljungdahlii,* or *Clostridium* ragsdalei. In another embodiment, the parental microorganism is *Clostridium autoethanogenum* LZ1561, which was deposited on Jun. 7, 2010 with Deutsche Sammlung von Mikroorganismen und Zellkulturen GmbH (DSMZ) located at Inhoffenstraße 7B, D-38124 Braunschweig, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the disclosure is derived from a parental microorganism. In one embodiment, the microorganism of the disclosure is derived from *Clostridium autoethanogenum, Clostridium ljungdahlii,* or *Clostridium* ragsdalei. In a preferred embodiment, the microorganism of the disclosure is derived from *Clostridium autoethanogenum* LZ1561, which is deposited under DSMZ accession number DSM23693.

The microorganism of the disclosure may be further classified based on functional characteristics. For example, the microorganism of the disclosure may be or may be derived from a C1-fixing microorganism, an anaerobe, an acetogen, an ethanologen, a carboxydotroph, an autotroph, and/or a methanotroph. The microorganism of the disclosure may be selected from chemoautotroph, hydrogenotroph, knallgas, methanotroph, or any combination thereof. In some embodiments, the microorganism may be hydrogen-oxidizing, carbon monoxide-oxidizing, knallgas, or any combination thereof, with the capability to grow and synthesize biomass on gaseous carbon sources such as syngas and/or $CO_2$, such that the production microorganisms synthesize targeted chemical products under gas cultivation. The microorganisms and methods of the present disclosure can enable low cost synthesis of biochemicals, which can compete on price with petrochemicals and higher-plant derived amino acids, proteins, and other biological nutrients. In certain embodiments, these amino acids, proteins, and other biological nutrients are predicted to have a substantially lower price than amino acids, proteins, and other biological nutrients produced through heterotrophic or microbial phototrophic synthesis. Knallgas microbes, hydrogenotrophs, carboxydotrophs, and chemoautotrophs more broadly, are able to capture $CO_2$ or CO as their sole carbon source to support biological growth. In some embodiments, this growth includes the biosynthesis of amino acids and proteins. Knallgas microbes and other hydrogenotrophs can use $H_2$ as a source of reducing electrons for respiration and biochemical synthesis. In some embodiments of the present invention knallgas organisms and/or hydrogenotrophs and/or carboxydotrophs and/or other chemoautotrophic microorganisms are grown on a stream of gasses including but not limited to one or more of the following: $CO_2$; CO; $H_2$; along with inorganic minerals dissolved in aqueous solution. In some embodiments knallgas microbes and/or hydrogenotrophs and/or carboxydotrophs and/or other chemoautotrophic and/or methanotrophic microorganisms convert greenhouse gases into biomolecules including amino acids and proteins.

Table 1 provides a representative list of microorganisms and identifies their functional characteristics.

more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Often, the microorganism of the disclosure is a C1-fixing bacterium. In a preferred embodiment, the microorganism of the disclosure is derived from a C1-fixing microorganism identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen), sometimes referred to as "microoxic conditions." Often, the microorganism of the disclosure is an anaerobe. In a preferred

TABLE 1

| | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/− [1] | + | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | − | + | + |
| *Clostridium formicoaceticum* | + | + | + | + | − | + | + |
| *Clostridium ljungdahlii* | + | + | + | + | + | + | + |
| *Clostridium magnum* | + | + | + | + | − | + | +/− [2] |
| *Clostridium ragsdalei* | + | + | + | + | + | + | + |
| *Clostridium scatologenes* | + | + | + | + | − | + | + |
| *Eubacterium limosum* | + | + | + | + | − | + | + |
| *Moorella thermautotrophica* | + | + | + | + | + | + | + |
| *Moorella thermoacetica* (formerly *Clostridium thermoaceticum*) | + | + | + | + | − [3] | + | + |
| *Oxobacter pfennigii* | + | + | + | + | − | + | + |
| *Sporomusa ovata* | + | + | + | + | − | + | +/− [4] |
| *Sporomusa silvacetica* | + | + | + | + | − | + | +/− [5] |
| *Sporomusa sphaeroides* | + | + | + | + | − | + | +/− [6] |
| *Thermoanaerobacter kivui* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Often, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or embodiment, the microorganism of the disclosure is derived from an anaerobe identified in Table 1.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, NY, 2006). All naturally occurring acetogens are C1-fixing, anaerobic, autotrophic, and non-methanotrophic. Often, the microorganism of the disclosure is an acetogen. In a preferred embodiment, the microorganism of the disclosure is derived from an acetogen identified in Table 1.

An "ethanologen" is a microorganism that produces or is capable of producing ethanol. Often, the microorganism of the disclosure is an ethanologen. In a preferred embodiment, the microorganism of the disclosure is derived from an ethanologen identified in Table 1.

An "autotroph" is a microorganism capable of growing in the absence of organic carbon. Instead, autotrophs use inorganic carbon sources, such as CO and/or $CO_2$. Often, the microorganism of the disclosure is an autotroph. In a preferred embodiment, the microorganism of the disclosure is derived from an autotroph identified in Table 1.

A "carboxydotroph" is a microorganism capable of utilizing CO as a sole source of carbon and energy. Often, the microorganism of the disclosure is a carboxydotroph. In a preferred embodiment, the microorganism of the disclosure is derived from a carboxydotroph identified in Table 1.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

The term "knallgas" refers to the mixture of molecular hydrogen and oxygen gas. A "knallgas microorganism" is a microbe that can use hydrogen as an electron donor and oxygen as an electron acceptor in respiration for the generation of intracellular energy carriers such as Adenosine-5'-triphosphate (ATP).

The terms "oxyhydrogen" and "oxyhydrogen microorganism" can be used synonymously with "knallgas" and "knallgas microorganism" respectively. Knallgas microorganisms generally use molecular hydrogen by means of hydrogenases, with some of the electrons donated from $H_2$ being utilized for the reduction of $NAD^+$ (and/or other intracellular reducing equivalents) and some of the electrons from $H_2$ being used for aerobic respiration. Knallgas microorganisms generally fix $CO_2$ autotrophically, through pathways including but not limited to the Calvin Cycle or the reverse citric acid cycle.

In one embodiment, the microorganism of the disclosure is derived from the cluster of Clostridia comprising the species *Clostridium autoethanogenum*, *Clostridium ljungdahlii*, and *Clostridium* ragsdalei. These species were first reported and characterized by Abrini, Arch Microbiol, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 m), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, Biotechnol Bioeng, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium* ragsdalei from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum*, *Clostridium ljungdahlii*, or *Clostridium* ragsdalei are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the disclosure may also be derived from an isolate or mutant of *Clostridium autoethanogenum*, *Clostridium ljungdahlii*, or *Clostridium* ragsdalei. Isolates and mutants of *Clostridium autoethanogenum* include JA1-1 (DSM10061) (Abrini, Arch Microbiol, 161: 345-351, 1994), LBS1560 (DSM19630) (WO 2009/064200), and LZ1561 (DSM23693) (WO 2012/015317). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593, 886), C-01 (ATCC 55988) (U.S. Pat. No. 6,368,819), 0-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium* ragsdalei include PI 1 (ATCC BAA-622, ATCC PTA-7826) (WO 2008/028055).

As described above, however, the microorganism of the disclosure may also be derived from essentially any parental microorganism, such as a parental microorganism selected from the group consisting of *Clostridium acetobutylicum*, *Clostridium beijerinckii*, *Escherichia coli*, and *Saccharomyces cerevisiae*.

In another embodiment, the microorganism of the disclosure is an aerobic bacterium. In one embodiment, the microorganism of the disclosure comprises aerobic hydrogen bacteria. In an embodiment, the aerobic bacteria comprising at least one disrupted gene.

A number of aerobic bacteria are known to be capable of carrying out fermentation for the disclosed methods and system. Examples of such bacteria that are suitable for use in the invention include bacteria of the genus *Cupriavidus* and *Ralstonia*. In some embodiments, the aerobic bacteria is *Cupriavidus necator* or *Ralstonia eutropha*. In some embodiments, the aerobic bacteria is *Cupriavidus alkaliphilus*. In some embodiments, the aerobic bacteria is *Cupriavidus basilensis*. In some embodiments, the aerobic bacteria is *Cupriavidus campinensis*. In some embodiments, the aerobic bacteria is *Cupriavidus gilardii*. In some embodiments, the aerobic bacteria is *Cupriavidus laharis*. In some embodiments, the aerobic bacteria is *Cupriavidus metalli-*

*durans.* In some embodiments, the aerobic bacteria is *Cupriavidus nantongensis.* In some embodiments, the aerobic bacteria is *Cupriavidus numazuensis.* In some embodiments, the aerobic bacteria is *Cupriavidus oxalaticus.* In some embodiments, the aerobic bacteria is *Cupriavidus pampae.* In some embodiments, the aerobic bacteria is *Cupriavidus pauculus.* In some embodiments, the aerobic bacteria is *Cupriavidus pinatubonensis.* In some embodiments, the aerobic bacteria is *Cupriavidus plantarum.* In some embodiments, the aerobic bacteria is *Cupriavidus respiraculi.* In some embodiments, the aerobic bacteria is *Cupriavidus taiwanensis.* In some embodiments, the aerobic bacteria is *Cupriavidus yeoncheonensis.*

In some embodiments, the microorganism is *Cupriavidus necator* DSM248 or DSM541.

In some embodiments, the aerobic bacteria comprises one or more exogenous nucleic acid molecules encoding a naturally occurring polypeptide, wherein the polypeptide is ribulose bisphosphate carboxylase, acetyl-CoA acetyltransferase, 3-hydroxybutyryl-CoA dehydratase, butyryl-CoA dehydrogenase, butanol dehydrogenase, electron-transferring flavoprotein large subunit, 3-hydroxybutyryl-CoA dehydrogenase, bifunctional acetaldehyde-CoA/alcohol dehydrogenase, acetaldehyde dehydrogenase, aldehyde decarbonylase, acyl-ACP reductase, L-1,2-propanediol oxidoreductase, acyltransferase, 3-oxoacyl-ACP synthase, 3-hydroxybutyryl-CoA epimerase/delta(3)-cis-delta(2)-trans-enoyl-CoA isomerase/enoyl-CoA hydratase/3-hydroxyacyl-CoA dehydrogenase, short chain dehydrogenase, trans-2-enoyl-CoA reductase, or any combination thereof.

In the microorganisms of the disclosure, carbon flux is strategically diverted away from nonessential or undesirable products and towards products of interest. In certain embodiments, these disrupted genes divert carbon flux away from nonessential or undesirable metabolic nodes and through target metabolic nodes to improve production of products downstream of those target metabolic nodes. In an embodiment, limitation selected from nutrients, dissolved oxygen, or any combination thereof diverts carbon flux to desired products.

In one embodiment, the microorganism of the disclosure is capable of producing ethylene. One embodiment is directed to a recombinant C1-fixing microorganism capable of producing ethylene from a carbon source comprising a nucleic acid encoding a group of exogenous enzymes comprising at least one ethylene forming enzyme (EFE). In some embodiments the EFE is derived from *Pseudomonas syringae.* The microorganism of an embodiment, further comprising a nucleic acid encoding a group of exogenous enzymes comprising at least one alpha-ketoglutarate permease (AKGP).

The microorganism of an embodiment, wherein a nucleic acid encoding a group of exogenous enzymes comprises at least one EFE, at least one AKGP, or any combination thereof. The microorganism of an embodiment, wherein a nucleic acid encoding a group of exogenous enzymes comprises at least one EFE and at least one AKGP. The microorganism of an embodiment, wherein the nucleotide encoding a group of exogenous enzymes is inserted into a bacterial vector plasmid, a high copy number bacterial vector plasmid, a bacterial vector plasmid having an inducible promoter, a nucleotide guide of a homologous recombination system, a CRISPR Cas system, or any combination thereof. In an embodiment, the promoter is a phosphate limited inducible promoter. In some embodiments, the promoter is an NtrC-P activated promoter. In some embodiments, the promoter is a $H_2$ inducible promoter. In one embodiment, the microorganism comprises an intracellular oxygen concentration limit. In another embodiment, the method limits intracellular oxygen concentration. In one embodiment, the method comprises a step of controlling dissolved oxygen. In an embodiment, the method comprises decreased ethylene production with decreased dissolved oxygen concentration. In some embodiments, the microorganism comprises a molecular switch. In some embodiments, the microorganism comprises an ability to switch the cellular burden under variable conditions.

In one embodiment, the aerobic bacteria may produce a product such as acetone, isopropanol, 3-hydroxyisovaleryl-CoA, 3-hydroxyisovalerate, isobutylene, isopentenyl pyrophosphate, dimethylallyl pyrophosphate, isoprene, farnesene, 3-hydroxybutyryl-CoA, crotonyl-CoA, 3-hydroxybutyrate, 3-hydroxybutyrylaldehyde, 1,3-butanediol, 2-hydroxyisobutyryl-CoA, 2-hydroxyisobutyrate, butyryl-CoA, butyrate, butanol, caproate, hexanol, octanoate, octanol, 1,3-hexanediol, 2-buten-1-ol, isovaleryl-CoA, isovalerate, isoamyl alcohol, methacrolein, methyl-methacrylate, or any combination thereof.

In another embodiment, the bacteria of the disclosure may produce ethylene, ethanol, propane, acetate, 1-butanol, butyrate, 2,3-butanediol, lactate, butene, butadiene, methyl ethyl ketone (2-butanone), acetone, isopropanol, a lipid, 3-hydroxypropionate (3-HP), a terpene, isoprene, a fatty acid, 2-butanol, 1,2-propanediol, 1propanol, 1hexanol, 1octanol, chorismate-derived products, 3hydroxybutyrate, 1,3butanediol, 2-hydroxyisobutyrate or 2-hydroxyisobutyric acid, isobutylene, adipic acid, keto-adipic acid, 1,3hexanediol, 3-methyl-2-butanol, 2-buten-1-ol, isovalerate, isoamyl alcohol, and monoethylene glycol, or any combination thereof.

The disclosure provides microorganisms capable of producing ethylene comprising culturing the microorganism of the disclosure in the presence of a substrate, whereby the microorganism produces ethylene.

The enzymes of the disclosure may be codon optimized for expression in the microorganism of the disclosure. "Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the disclosure are codon optimized for expression in the microorganism of the disclosure. Although codon optimization refers to the underlying genetic sequence, codon optimization often results in improved translation and, thus, improved enzyme expression. Accordingly, the enzymes of the disclosure may also be described as being codon optimized.

One or more of the enzymes of the disclosure may be overexpressed. "Overexpressed" refers to an increase in expression of a nucleic acid or protein in the microorganism of the disclosure compared to the wild-type or parental microorganism from which the microorganism of the disclosure is derived. Overexpression may be achieved by any means known in the art, including modifying gene copy number, gene transcription rate, gene translation rate, or enzyme degradation rate. As described above, one or more of the enzymes catalyzing reactions 2, 5, 6, 8, 9, 10, 19, 20, 24, or 25 of FIG. 1 may be overexpressed.

The enzymes of the disclosure may comprise a disruptive mutation. A "disruptive mutation" refers to a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

Introduction of a disruptive mutation results in a microorganism of the disclosure that produces no target product or substantially no target product or a reduced amount of target product compared to the parental microorganism from which the microorganism of the disclosure is derived. For example, the microorganism of the disclosure may produce no target product or at least about 1%, 3%, 5%, 10%, 20%, 30%, 40%, 50%, 60%, 70%, 80%, 90%, or 95% less target product than the parental microorganism. For example, the microorganism of the disclosure may produce less than about 0.001, 0.01, 0.10, 0.30, 0.50, or 1.0 g/L target product.

Although exemplary sequences and sources for enzymes are provided herein, the disclosure is by no means limited to these sequences and sources—it also encompasses variants. The term "variants" includes nucleic acids and proteins whose sequence varies from the sequence of a reference nucleic acid and protein, such as a sequence of a reference nucleic acid and protein disclosed in the prior art or exemplified herein. The disclosure may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like.

Homologous genes from other microorganisms are also examples of functionally equivalent variants. These include homologous genes in species such as *Clostridium acetobutylicum*, *Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Nucleic acids may be delivered to a microorganism of the disclosure using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the disclosure using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate ferredoxin oxidoreductase promoter, an Rnf complex operon promoter, an ATP synthase operon promoter, or a phosphotransacetylase/acetate kinase operon promoter.

It should be appreciated that the disclosure may be practiced using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants." By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein.

These include homologous genes in species such as *Clostridium ljungdahlii, Chloroflexus aurantiacus*, Metallosphaera or *Sulfolobus* spp, details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the disclosure may be practiced using polypeptides whose sequence varies from the amino acid sequences specifically exemplified herein. These variants may be referred to herein as "functionally equivalent variants." A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

The microorganisms of the disclosure may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the disclosure is produced by a method comprises the following steps: introduction into a shuttle microorganism of (i) of an expression construct/vector as described herein and (ii) a methylation construct/vector comprising a methyltransferase gene; expression of the methyltransferase gene; isolation of one or more constructs/vectors from the shuttle microorganism; and, introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism that facilitates the methylation of the nucleic acid sequences that make up the expression construct/vector. In a particular embodiment, the shuttle microorganism is a restriction negative *E. coli, Bacillus subtilis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the disclosure, the methylation construct/vector comprises an inducible lac promoter and is induced by addition of lactose or an analogue thereof, more preferably isopropyl-β-D-thiogalactoside (IPTG). Other suitable promoters include the ara, tet, or T7 system. In a further embodiment of the disclosure, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the disclosure.

In one particular embodiment, the expression construct/vector and/or the methylation construct/vector are plasmids.

Persons of ordinary skill in the art will appreciate a number of suitable methyltransferases of use in producing the microorganisms of the disclosure. However, by way of example the *Bacillus subtilis* phage (DT1 methyltransferase and the methyltransferase described in the Examples herein after may be used. Nucleic acids encoding suitable methyltransferases will be readily appreciated having regard to the sequence of the desired methyltransferase and the genetic code.

Any number of constructs/vectors adapted to allow expression of a methyltransferase gene may be used to generate the methylation construct/vector.

In one embodiment, the substrate comprises CO. In one embodiment, the substrate comprises CO2 and CO. In another embodiment, the substrate comprises CO2 and H2. In another embodiment, the substrate comprises CO2 and CO and H2.

"Substrate" refers to a carbon and/or energy source for the microorganism of the disclosure. Often, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons. In other embodiments, however, the substrate may be a carbohydrate, such as sugar, starch, fiber, lignin, cellulose, or hemicellulose or a combination thereof. For example, the carbohydrate may be fructose, galactose, glucose, lactose, maltose, sucrose, xylose, or some combination thereof. In some embodiments, the substrate does not comprise (D)-xylose (Alkim, *Microb Cell Fact,* 14: 127, 2015). In some embodiments, the substrate does not comprise a pentose such as xylose (Pereira, *Metab Eng,* 34: 80-87, 2016). In some embodiments, the substrate may comprise both gaseous and carbohydrate substrates (mixotrophic fermentation). The substrate may further comprise other non-carbon components, such as $H_2$, $N_2$, or electrons.

The gaseous substrate generally comprises at least some amount of CO, such as about 1, 2, 5, 10, 20, 30, 40, 50, 60, 70, 80, 90, or 100 mol % CO. The gaseous substrate may comprise a range of CO, such as about 20-80, 30-70, or 40-60 mol % CO. Preferably, the gaseous substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the gaseous substrate may comprise a relatively low amount of CO, such as about 1-10 or 1-20 mol % CO. The microorganism of the disclosure typically converts at least a portion of the CO in the gaseous substrate to a product. In some embodiments, the gaseous substrate comprises no or substantially no (<1 mol %) CO.

The gaseous substrate may comprise some amount of $H_2$. For example, the gaseous substrate may comprise about 1, 2, 5, 10, 15, 20, or 30 mol % $H_2$. In some embodiments, the gaseous substrate may comprise a relatively high amount of $H_2$, such as about 60, 70, 80, or 90 mol % $H_2$. In further embodiments, the gaseous substrate comprises no or substantially no (<1 mol %) $H_2$.

The gaseous substrate may comprise some amount of $CO_2$. For example, the gaseous substrate may comprise about 1-80 or 1-30 mol % $CO_2$. In some embodiments, the gaseous substrate may comprise less than about 20, 15, 10, or 5 mol % $CO_2$. In another embodiment, the gaseous substrate comprises no or substantially no (<1 mol %) $CO_2$.

The gaseous substrate may also be provided in alternative forms. For example, the gaseous substrate may be dissolved in a liquid or adsorbed onto a solid support.

The gaseous substrate and/or C1-carbon source may be a waste gas or an off gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the gaseous substrate and/or C1-carbon source may be captured from the industrial process before it is emitted into the atmosphere, using any convenient method.

The gaseous substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The terms "feedstock" when used in the context of the stream flowing into a gas fermentation bioreactor (i.e., gas fermenter) or "gas fermentation feedstock" should be understood to encompass any material (solid, liquid, or gas) or stream that can provide a substrate and/or C1-carbon source to a gas fermenter or bioreactor either directly or after processing of the feedstock.

The term "waste gas" or "waste gas stream" may be used to refer to any gas stream that is either emitted directly, flared with no additional value capture, or combusted for energy recovery purposes.

The terms "synthesis gas" or "syngas" refers to a gaseous mixture that contains at least one carbon source, such as carbon monoxide (CO), carbon dioxide ($CO_2$), or any combination thereof, and, optionally, hydrogen ($H_2$) that can used as a feedstock for the disclosed gas fermentation processes and can be produced from a wide range of carbonaceous material, both solid and liquid.

The substrate and/or C1-carbon source may be a waste gas obtained as a byproduct of an industrial process or from another source, such as automobile exhaust fumes, biogas, landfill gas, direct air capture, or from electrolysis. The substrate and/or C1-carbon source may be syngas generated by pyrolysis, torrefaction, or gasification. In other words, carbon in waste material may be recycled by pyrolysis, torrefaction, or gasification to generate syngas which is used as the substrate and/or C1-carbon source. The substrate and/or C1-carbon source may be a gas comprising methane.

In certain embodiments, the industrial process is selected from ferrous metal products manufacturing, such as a steel manufacturing, non-ferrous products manufacturing, petroleum refining, electric power production, carbon black production, paper and pulp manufacturing, ammonia production, methanol production, coke manufacturing, petrochemical production, carbohydrate fermentation, cement making, aerobic digestion, anaerobic digestion, catalytic processes, natural gas extraction, cellulosic fermentation, oil extraction, geological reservoirs, gas from fossil resources such as natural gas coal and oil, or any combination thereof.

Examples of specific processing steps within an industrial process include catalyst regeneration, fluid catalyst cracking, and catalyst regeneration. Air separation and direct air capture are other suitable industrial processes. Specific examples in steel and ferroalloy manufacturing include blast furnace gas, basic oxygen furnace gas, coke oven gas, direct reduction of iron furnace top-gas, and residual gas from smelting iron. In these embodiments, the substrate and/or C1-carbon source may be captured from the industrial process before it is emitted into the atmosphere, using any known method.

The substrate and/or C1-carbon source may be synthesis gas known as syngas, which may be obtained from reforming, partial oxidation, or gasification processes. Examples of gasification processes include gasification of coal, gasification of refinery residues, gasification of petroleum coke, gasification of biomass, gasification of lignocellulosic material, gasification of waste wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of biogas. Examples of reforming processes include, steam methane reforming, steam naphtha reforming, reforming of natural gas, reforming of biogas, reforming of landfill gas, naphtha reforming, and dry methane reforming. Examples of partial oxidation processes include thermal and catalytic partial oxidation processes, catalytic partial oxidation of natural gas, partial oxidation of hydrocarbons. Examples of municipal solid waste include tires, plastics, fibers, such as in shoes, apparel, and textiles. Municipal solid waste may be simply landfill-type waste. The municipal solid waste may be sorted or unsorted. Examples of biomass may include lignocellulosic material and may also include microbial biomass.

Lignocellulosic material may include agriculture waste and forest waste.

The substrate and/or C1-carbon source may be a gas stream comprising methane. Such a methane containing gas may be obtained from fossil methane emission such as during fracking, wastewater treatment, livestock, agriculture, and municipal solid waste landfills. It is also envisioned that the methane may be burned to produce electricity or heat, and the C1 byproducts may be used as the substrate or carbon source.

The composition of the gaseous substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

Regardless of the source or precise content of the gas used as a feedstock, the feedstock may be metered (e.g., for carbon credit calculations or mass balancing of sustainable carbon with overall products) into a bioreactor in order to maintain control of the follow rate and amount of carbon provided to the culture. Similarly, the output of the bioreactor may be metered (e.g., for carbon credit calculations or mass balancing of sustainable carbon with overall products) or comprise a valved connection that can control the flow of the output and products (e.g., ethylene, ethanol, acetate, 1-butanol, etc.) produced via fermentation. Such a valve or metering mechanism can be useful for a variety of purposes including, but not limited to, slugging of product through a connected pipeline and measuring the amount of output from a given bioreactor such that if the product is mixed with other gases or liquids the resulting mixture can later be mass balanced to determine the percentage of the product that was produced from the bioreactor.

In certain embodiments, the fermentation is performed in the absence of carbohydrate substrates, such as sugar, starch, fiber, lignin, cellulose, or hemicellulose.

In addition to tandem repeat proteins and chemical products, the microorganism of the disclosure may be cultured to produce one or more co-products. For instance, the microorganism of the disclosure may produce or may be engineered to produce ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and/or monoethylene glycol (WO 2019/126400) in addition to ethylene. In certain embodiments, microbial biomass itself may be considered a product. These products may be further converted to produce at least one component of diesel, jet fuel, sustainable aviation fuel (SAF), and/or gasoline. In certain embodiments, ethylene may be catalytically converted into another product, article, or any combination thereof. Additionally, the microbial biomass may be further processed to produce a single cell protein (SCP) by any method or combination of methods known in the art. In addition to one or more target chemical products, the microorganism of the disclosure may also produce ethanol, acetate, and/or 2,3-butanediol. In another embodiment, the microorganism and methods of the disclosure improve the production of products, proteins, microbial biomass, or any combination thereof.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism but is not produced by a genetically unmodified microorganism from which the genetically modified microorganism is derived. Ethylene is not known to be produced by any naturally-occurring microorganism, such that it is a non-native product of all microorganisms.

"Selectivity" refers to the ratio of the production of a target product to the production of all fermentation products produced by a microorganism. The microorganism of the disclosure may be engineered to produce products at a certain selectivity or at a minimum selectivity. In one embodiment, a target product, such as ethylene glycol, accounts for at least about 5%, 10%, 15%, 20%, 30%, 50%, or 75% of all fermentation products produced by the microorganism of the disclosure. In one embodiment, ethylene accounts for at least 10% of all fermentation products produced by the microorganism of the disclosure, such that the microorganism of the disclosure has a selectivity for ethylene glycol of at least 10%. In another embodiment, ethylene accounts for at least 30% of all fermentation products produced by the microorganism of the disclosure, such that the microorganism of the disclosure has a selectivity for ethylene of at least 30%.

At least one of the one or more fermentation products may be biomass produced by the culture. At least a portion of the microbial biomass may be converted to a single cell protein (SCP). At least a portion of the single cell protein may be utilized as a component of animal feed.

In one embodiment, the disclosure provides an animal feed comprising microbial biomass and at least one excipient, wherein the microbial biomass comprises a microorganism grown on a gaseous substrate comprising one or more of CO, CO2, and H2.

A "single cell protein" (SCP) refers to a microbial biomass that may be used in protein-rich human and/or animal feeds, often replacing conventional sources of protein supplementation such as soymeal or fishmeal. To produce a single cell protein, or other product, the process may comprise additional separation, processing, or treatments steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

"Microbial biomass" refers biological material comprising microorganism cells. For example, microbial biomass may comprise or consist of a pure or substantially pure culture of a bacterium, archaea, virus, or fungus. When initially separated from a fermentation broth, microbial biomass generally contains a large amount of water. This water may be removed or reduced by drying or processing the microbial biomass.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavour, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, 3rd revision, pages 575-633, 2014.

A "biopolymer" refers to natural polymers produced by the cells of living organisms. In certain embodiments, the biopolymer is PHA. In certain embodiments, the biopolymer is PHB.

A "bioplastic" refers to plastic materials produced from renewable biomass sources. A bioplastic may be produced from renewable sources, such as vegetable fats and oils, corn starch, straw, woodchips, sawdust, or recycled food waste.

Herein, reference to an acid (e.g., acetic acid or 2-hydroxyisobutyric acid) should be taken to also include the corresponding salt (e.g., acetate or 2-hydroxyisobutyrate).

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of ethylene glycol. If necessary, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

A "sparger" may comprise a device to introduce gas into a liquid, injected as bubbles, to agitate it or to dissolve the gas in the liquid. Example spargers may include orifice spargers, sintered spargers, and drilled pipe spargers. In certain configurations drilled pipe spargers may be mounted horizontally. In other examples, spargers may be mounted vertically or horizontally. In some examples, the sparger may be a perforated plate or ring, sintered glass, sintered steel, porous rubber pipe, porous metal pipe, porous ceramic or stainless steel, drilled pipe, stainless steel drilled pipe, polymeric drilled pipe, etc. The sparger may be of various grades (porosities) or may include certain sized orifices to produce a specific sized bubble or range of bubble sizes.

A "vessel", "reaction vessel", or "column" may be a vessel or container in which one or more gas and liquid streams, or flows may be introduced for bubble generation and/or fine bubble generation, and for subsequent gas-liquid contacting, gas-absorption, biological or chemical reaction, or surface-active material adsorption. In a reaction vessel, the gas and liquid phases may flow in the vertical directions. In a reaction vessel, larger bubbles from a sparger, having a buoyancy force larger than the drag force imparted by the liquid, may rise upwards. Smaller fine bubbles, having a buoyancy force less than or equal to the drag force imparted by the liquid, may flow downward with the liquid, as described by the systems and methods disclosed herein. A column or reaction vessel may not be restricted to any specific aspect (height to diameter) ratio. A column or reaction vessel may also not be restricted to any specific material and can be constructed from any material suitable to the process such as stainless steel, PVC, carbon steel, or polymeric material. A column or reaction vessel may contain internal components such as one or more static mixers that are common in biological and chemical engineering processing. A reaction vessel may also consist of external or internal heating or cooling elements such as water jackets, heat exchangers, or cooling coils. The reaction vessel may also be in fluid contact with one or more pumps to circulate liquid, bubbles, fine bubbles, and or one or more fluids of the system.

A "perforated plate" or "plate" may comprise a plate or similar arrangement designed to facilitate the introduction of liquid or additional liquid into the vessel that may be in the form of multiple liquid jets (i.e., accelerated liquid flow). The perforated plate may have a plurality of pores or orifices evenly or unevenly distributed across the plate that allow the flow of liquid from a top of the plate to the bottom of the plate. In some examples, the orifices may be spherical-shaped, rectangular-shaped, hexagonal prism-shaped, conical-shaped, pentagonal prism-shaped, cylindrical-shaped, frustoconical-shaped, or round-shaped. In other examples, the plate may comprise one or more nozzles adapted to generate liquid jets which flow into the column. The plate may also contain channels in any distribution or alignment where such channels are adapted to receive liquid and facilitate flow through into the reaction vessel. The plate may be made of stainless steel with a predefined number of laser-burnt, machined, or drilled pores or orifices. The specific orifice size may depend upon the required fine bubble size and required liquid, fine bubble, and/or fluid velocities. A specific orifice shape may be required to achieve the proper liquid acceleration and velocity from the plate to break or shear the sparger bubbles into the desired fine bubble size, and to create enough overall fluid downflow to carry the fine bubbles and liquid downward in the reaction vessel. The shape of the orifice may also impact ease of manufacturing and related costs. According to one embodiment, a straight orifice may be optimal due to ease of manufacture.

The systems and methods as disclosed herein, employ, within a vessel, multiple liquid jets or portions of accelerated liquid flow generated using the perforated plate to accelerate liquid and break bubbles into smaller fine bubbles having a greater superficial surface area than the original bubbles. The original bubbles are initially generated by injecting gas with a sparger positioned entirely within the reaction vessel. In one example, original bubbles injected into liquid from a sparger may have a diameter of about 2 mm to about 20 mm. In another example, original bubbles injected into liquid from a sparger may have a diameter of about 5 mm to about 15 mm. In other examples, original bubbles injected into liquid from a sparger may have a diameter of about 7 mm to about 13 mm. Upon injection, the original bubbles subsequently migrate upwards through the liquid and encounter the multiple liquid jets or portions of accelerated liquid flow which breaks the original bubbles into fine bubbles. The resulting fine bubbles and liquid flow down the reactor vessel in the downward fluid flow. The fine bubbles of substrate provide a carbon source and optionally an energy source to the microbes which then produce one or more desired products. The spargers are positioned within the vessel to create a first zone for the original bubbles to rise within the vessel, and to create a second zone for the accelerated liquid to break the original bubbles into fine bubbles and for fluid to flow through the vessel, where the fluid comprises the accelerated portion of the liquid and fine bubbles.

Due to the nature of the multi-phase system, one approach to maximizing product generation is to increase gas to liquid mass transfer. The more gas substrate transferred to a reaction liquid, the greater the desired product generated. The smaller fine bubbles of the present disclosure provide an increased superficial surface area resulting in an increased gas to liquid mass transfer rates overcoming known solubility issues. Additionally, the downflow reactor systems disclosed herein are effective to increase the residence time of the fine bubbles. The increased time that the fine bubbles remain in the reaction liquid generally provides increased amounts of reaction product generated, as well as greater surface areas in contact with the microbes. As such, the systems and methods disclosed herein improve over previous systems by generating fine bubbles that maximize gas to liquid superficial surface areas leading to high gas to liquid mass transfer rates. Further, the systems and methods disclosed herein provide superficial gas and liquid velocities not achieved by the previous systems and methods resulting in the generation of fine bubbles with high gas phase residence time resulting in the efficient creation of chemical and biological reaction products.

In certain embodiments, the fermentation is performed in the absence of light or in the presence of an amount of light insufficient to meet the energetic requirements of photosynthetic microorganisms. In certain embodiments, the microorganism of the disclosure is a non-photosynthetic microorganism.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor. Purification techniques may include affinity tag purification (e.g. His, Twin-Strep, and FLAG), bead-based systems, a tip-based approach, and FPLC system for larger scale, automated purifications. Purification methods that do not rely on affinity tags (e.g. salting out, ion exchange, and size exclusion) are also disclosed.

In some embodiments, the produced chemical product may be isolated and enriched, including purified, using any suitable separation and/or purification technique known in the art. In an embodiment, the produced chemical product is gaseous. In one embodiment, the chemical product is a liquid. In an embodiment, a gaseous chemical product may pass a filter, a gas separation membrane, a gas purifier, or any combination thereof. In one embodiment, the chemical product is separated by an absorbent column. In another embodiment, the chemical product is stored in one or more cylinders after separation. In one embodiment, the chemical product is integrated into an infrastructure or process of an oil, gas, refinery, petrochemical operation, or any combination thereof. The infrastructure or process may be existing or new. In an embodiment, the gas fermentation product is integrated into oil and gas production, transportation and refining, and/or chemical complexes. In another embodiment, the source of the feedstock is from an oil, gas, refinery, petrochemical operation, or any combination thereof. In an embodiment, the gas fermentation product is integrated into an infrastructure or process of an oil, gas, refinery, petrochemical operation, or any combination thereof, and the source of the feedstock is from an oil, gas, refinery, petrochemical operation, or any combination thereof.

In some embodiments, distillation may be employed to purify a product gas. In an embodiment, gas-liquid extraction may be employed. In an embodiment, a liquid product isolation may also be enriched via extraction using an organic phase. In another embodiment, purification may involve other standard techniques selected from ultrafiltration, one or more chromatographic techniques, or any combination thereof.

The method of the disclosure may further comprise separating a gas fermentation product from the fermentation broth. The gas fermentation product may be separated or purified from a fermentation broth using any method or combination of methods known in the art, including, for example, distillation, simulated moving bed processes, membrane treatment, evaporation, pervaporation, gas stripping, phase separation, ion exchange, or extractive fermentation, including for example, liquid-liquid extraction. As described in U.S. Pat. No. 2,769,321, the disclosure of which is incorporated by reference in its entirety herein, ethylene may be separated according to the method or combination of methods known in the art. In one embodiment, the ethylene produced is harvested from the bioreactor culture vessel.

In one embodiment, the gas fermentation product may be concentrated from the fermentation broth using reverse osmosis and/or pervaporation (U.S. Pat. No. 5,552,023). Water may be removed by distillation and the bottoms (containing a high proportion of gas fermentation product) may then be recovered using distillation or vacuum distillation to produce a high purity stream. Alternatively, with or without concentration by reverse osmosis and/or pervaporation, the gas fermentation product may be further purified by reactive distillation with an aldehyde (Atul, *Chem Eng Sci*, 59: 2881-2890, 2004) or azeotropic distillation using a hydrocarbon (U.S. Pat. No. 2,218,234). In another approach, the gas fermentation product may be trapped on an activated carbon or polymer absorbent from aqueous solution (with or without reverse osmosis and/or pervaporation) and recovered using a low boiling organic solvent (Chinn, Recovery of Glycols, Sugars, and Related Multiple —OH Compounds from Dilute-Aqueous Solution by Regenerable Adsorption onto Activated Carbons, University of California Berkeley, 1999). The gas fermentation product can then be recovered from the organic solvent by distillation. In certain embodiments, the gas fermentation product is recovered from the fermentation broth by continuously removing a portion of the broth from the bioreactor, separating microbial cells from the broth (conveniently by filtration), and recovering the gas fermentation product from the broth. Co-products, such as alcohols or acids may also be separated or purified from the broth. Alcohols may be recovered, for example, by distillation. Acids may be recovered, for example, by adsorption on activated charcoal. Separated microbial cells may be returned to the bioreactor in certain embodiments. Further, separated microbial cells may be recycled to the bioreactor in some embodiments. The cell-free permeate remaining after target products have been removed is also preferably returned to the bioreactor, in whole or in part. Additional nutrients (such as B vitamins) may be added to the cell-free permeate to replenish the medium before it is returned to the bioreactor.

Recovery of diols from aqueous media has been demonstrated a number of ways. Simulated moving bed (SMB) technology has been used to recover 2,3-butanediol from an aqueous mixture of ethanol and associated oxygenates (U.S. Pat. No. 8,658,845). Reactive separation has also been demonstrated for effective diol recovery. In some embodiments, recovery of ethylene glycol is conducted by reaction of the diol-containing stream with aldehydes, fractionation and regeneration of the diol, final fractionation to recover a concentrated diol stream. See, e.g., U.S. Pat. No. 7,951,980.

In one embodiment, the method comprises recovering ethylene produced as disclosed above. In one embodiment, the method further comprises converting or using ethylene in the production of one or more chemical products following recovery of ethylene.

Ethylene is a high value gaseous compound which is widely used in industry. In an embodiment, ethylene may be used as an anaesthetic or as a fruit ripening agent, as well as in the production of a number of other chemical products. In some embodiments, ethylene may be used to produce polyethylene and other polymers, such as styrene, polystyrene, ethylene oxide, ethylene dichloride, ethylene dibromide, ethyl chloride and ethylbenzene. Ethylene oxide is, for example, a key raw material in the production of surfactants and detergents and in the production of ethylene glycol, which is used in the automotive industry as an antifreeze product. In one embodiment directed to ethylene dichloride, ethylene dibromide, and ethyl chloride may be used to produce products such as polyvinyl chloride, trichloroethylene, perchloroethylene, methyl chloroform, polyvinylidene chloride and copolymers, and ethyl bromide. In an embodiment, ethylbenzene is a precursor to styrene, which is used in the production of polystyrene (used as an insulation product) and styrene-butadiene (which is rubber suitable for use in tires and footwear). In another embodiment, a product is an ethylene propylene diene monomer (EPDM) rubber, an ethylene propylene (EPR/EPM) rubber, or any combination thereof.

It should be appreciated that the methods of the invention may be integrated or linked with one or more methods for the production of downstream chemical products from ethylene. In some embodiments, the methods of the invention may feed ethylene directly or indirectly to chemical processes or reactions sufficient for the conversion or production of other useful chemical products.

In some embodiments, ethylene is converted into hydrocarbon liquid fuels. In an embodiment, ethylene is oligomerized over a catalyst to selectively produce target products selected from gasoline, condensate, aromatics, heavy oil diluents, distillates, or any combination thereof. In other embodiments, the distillates are selected from diesel, jet fuel, sustainable aviation fuel (SAF), or any combination thereof.

In one embodiment, ethylene oligomerization is utilized towards desirable products. In an embodiment, oligomerization of ethylene may be catalyzed by a homogeneous catalyst, heterogeneous catalyst, or any combination thereof and having transition metals as active sites. In some embodiments, ethylene is further converted into long chain hydrocarbons by oligomerization. In other embodiments, straight chain olefins are the main product from ethylene oligomerization. In some embodiments, alpha olefins are the main product from ethylene oligomerization. In an embodiment, olefins are subjected to upgrading processes. In some embodiments, the upgrading process of olefins is hydrogenation. In an embodiment, olefins are subjected to olefin conversion technology. In one embodiment, ethylene is interconverted to propylene, 2-butenes, or any combination thereof. In an embodiment, propylene is converted to polypropylene.

As a raw material, ethylene can used in the manufacture of polymers such as polyethylene (PE), polyethylene terephthalate (PET) and polyvinyl chloride (PVC), ethylene vinyl acetate (EVA), as well as fibres and other organic chemicals. These products are used in a wide variety of industrial and consumer markets such as the packaging, transportation, electrical/electronic, textile and construction industries as well as consumer chemicals, coatings and adhesives.

Ethylene can be chlorinated to ethylene dichloride (EDC) and can then be cracked to make vinyl chloride monomer (VCM). Nearly all VCM is used to make polyvinyl chloride which has its main applications in the construction industry.

Other ethylene derivatives include alpha olefins which are used in Linear low-density polyethylene (LLDPE) production, detergent alcohols and plasticizer alcohols; vinyl acetate monomer (VAM) which is used in adhesives, paints, paper coatings and barrier resins; and industrial ethanol which is used as a solvent or in the manufacture of chemical intermediates such as ethyl acetate and ethyl acrylate.

Ethylene may further be used as a monomer base for the production of various polyethylene oligomers by way of coordination polymerization using metal chloride or metal oxide catalysts. The most common catalysts consist of titanium (III) chloride, the so-called Ziegler-Natta catalysts. Another common catalyst is the Phillips catalyst, prepared by depositing chromium (VI) oxide on silica.

Polyethylene oligomers so produced may be classified according to its density and branching. Further, mechanical properties depend significantly on variables such as the extent and type of branching, the crystal structure, and the molecular weight. There are several types of polyethylene which may be generated from ethylene, including, but not limited to:

Ultra-high-molecular-weight polyethylene (UHMWPE);
Ultra-low-molecular-weight polyethylene (ULMWPE or PE-WAX);
High-molecular-weight polyethylene (HMWPE);
High-density polyethylene (HDPE);
High-density cross-linked polyethylene (HDXLPE);
Cross-linked polyethylene (PEX or XLPE);
Medium-density polyethylene (MDPE);
Linear low-density polyethylene (LLDPE);
Low-density polyethylene (LDPE);
Very-low-density polyethylene (VLDPE); and
Chlorinated polyethylene (CPE).

Low density polyethylene (LDPE) and linear low-density polyethylene (LLDPE) mainly go into film applications such as food and non-food packaging, shrink and stretch film, and non-packaging uses. High density polyethylene (HDPE) is used primarily in blow molding and injection molding applications such as containers, drums, household goods, caps and pallets. HDPE can also be extruded into pipes for water, gas and irrigation, and film for refuse sacks, carrier bags and industrial lining.

According to one embodiment, the ethylene formed from the disclosure described above may be converted to ethylene oxide via direct oxidation according to the following formula:

$$C_2H_4 + O_2 \rightarrow C_2H_4O$$

The ethylene oxide produced thereby is a key chemical intermediate in a number of commercially important processes including the manufacture of monoethylene glycol. Other EO derivatives include ethoxylates (for use in shampoo, kitchen cleaners, etc.), glycol ethers (solvents, fuels, etc.) and ethanolamines (surfactants, personal care products, etc.).

According to one embodiment of the disclosure, the ethylene oxide produced as described above may be used to produce commercial quantities of monoethylene glycol by way of the formula:

$$(CH_2CH_2)O + H_2O \rightarrow HOCH_2CH_2OH$$

According to another embodiment, the claimed microorganism can be modified in order to directly produce monoethylene glycol. As described in WO 2019/126400, the disclosure of which is incorporated by reference in its entirety herein, the microorganism further comprises one or more of an enzymes capable of converting acetyl-CoA to pyruvate; an enzyme capable of converting pyruvate to oxaloacetate; an enzyme capable of converting pyruvate to malate; an enzyme capable of converting pyruvate to phosphoenolpyruvate; an enzyme capable of converting oxaloacetate to citryl-CoA; an enzyme capable of converting citryl-CoA to citrate; an enzyme capable of converting citrate to aconitate and aconitate to iso-citrate; an enzyme capable of converting phosphoenolpyruvate to oxaloacetate; an enzyme capable of converting phosphoenolpyruvate to 2-phospho-D-glycerate; an enzyme capable of converting 2-phospho-D-glycerate to 3-phospho-D-glycerate; an enzyme capable of converting 3-phospho-D-glycerate to 3-phosphonooxypyruvate; an enzyme capable of converting 3-phospho-nooxypyruvate to 3-phospho-L-serine; an enzyme capable of converting 3-phospho-L-serine to serine; an enzyme capable of converting serine to glycine; an enzyme capable of converting 5,10-methylenetetrahydrofolate to glycine; an enzyme capable of converting serine to hydroxypyruvate; an enzyme capable of converting D-glycerate to hydroxypyruvate; an enzyme capable of converting malate to glyoxylate; an enzyme capable of converting glyoxylate to glycolate; an enzyme capable of converting hydroxypyruvate to glycolaldehyde; and/or an enzyme capable of converting glycolaldehyde to ethylene glycol.

In one embodiment, the microorganism comprises one or more of a heterologous enzyme capable of converting oxaloacetate to citrate; a heterologous enzyme capable of converting glycine to glyoxylate; a heterologous enzyme capable of converting iso-citrate to glyoxylate; a heterologous enzyme capable of converting glycolate to glycolaldehyde; or any combination thereof. In some embodiments, wherein the heterologous enzyme capable of converting oxaloacetate to citrate is a citrate [Si]-synthase [2.3.3.1], an ATP citrate synthase [2.3.3.8]; or a citrate (Re)-synthase [2.3.3.3]; the heterologous enzyme capable of converting glycine to glyoxylate is an alanine-glyoxylate transaminase [2.6.1.44], a serine-glyoxylate transaminase [2.6.1.45], a serine-pyruvate transaminase [2.6.1.51], a glycine-oxaloacetate transaminase [2.6.1.35], a glycine transaminase [2.6.1.4], a glycine dehydrogenase [1.4.1.10], an alanine dehydrogenase [1.4.1.1], or a glycine dehydrogenase [1.4.2.1]; the heterologous enzyme capable of converting iso-citrate to glyoxylate is an isocitrate lyase [4.1.3.1]; the heterologous enzyme capable of converting glycolate to glycolaldehyde is a glycolaldehyde dehydrogenase [1.2.1.21], a lactaldehyde dehydrogenase [1.2.1.22], a succinate-semialdehyde dehydrogenase [1.2.1.24], a 2,5-dioxovalerate dehydrogenase [1.2.1.26], an aldehyde dehydrogenase [1.2.1.3/4/5], a betaine-aldehyde dehydrogenase [1.2.1.8], or an aldehyde ferredoxin oxidoreductase [1.2.7.5]; or any combination thereof.

Monoethylene glycol produced according to either of the described methods may be used as a component of a variety of products including as a raw material to make polyester fibers for textile applications, including nonwovens, cover stock for diapers, building materials, construction materials, road-building fabrics, filters, fiberfill, felts, transportation upholstery, paper and tape reinforcement, tents, rope and cordage, sails, fish netting, seatbelts, laundry bags, synthetic artery replacements, carpets, rugs, apparel, sheets and pillowcases, towels, curtains, draperies, bed ticking, and blankets.

MEG may be used on its own as a liquid coolant, antifreeze, preservative, dehydrating agent, drilling fluid or any combination thereof. The MEG produced may also be used to produce secondary products such as polyester resins for use in insulation materials, polyester film, de-icing fluids, heat transfer fluids, automotive antifreeze and other liquid coolants, preservatives, dehydrating agents, drilling fluids, water-based adhesives, latex paints and asphalt emulsions, electrolytic capacitors, paper, and synthetic leather.

Importantly, the monoethylene glycol produced may be converted to the polyester resin polyethylene terephthalate ("PET") according to one of two major processes. The first process comprises transesterification of the monoethylene glycol utilizing dimethyl terephthalate, according to the following two-step process:

First Step

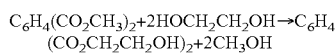

Second Step

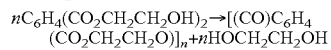

Alternatively, the monoethylene glycol can be the subject of an esterification reaction utilizing terephthalic acid according to the following reaction:

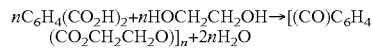

The polyethylene terephthalate produced according to either the transesterification or esterification of monoethylene glycol has significant applicability to numerous packaging applications such as jars and, in particular, in the production of bottles, including plastic bottles. It can also be used in the production of high-strength textile fibers such as Dacron, as part of durable-press blends with other fibers such as rayon, wool, and cotton, for fiber fillings used in insulated clothing, furniture, and pillows, in artificial silk, as carpet fiber, automobile tire yarns, conveyor belts and drive belts, reinforcement for fire and garden hoses, seat belts, nonwoven fabrics for stabilizing drainage ditches, culverts, and railroad beds, and nonwovens for use as diaper topsheets, and disposable medical garments.

At a higher molecular weight, PET can be made into a high-strength plastic that can be shaped by all the common methods employed with other thermoplastics. Magnetic recording tape and photographic film are produced by extrusion of PET film. Molten PET can be blow-molded into transparent containers of high strength and rigidity that are also virtually impermeable to gas and liquid. In this form, PET has become widely used in bottles, especially plastic bottles, and in jars.

The disclosure provides compositions comprising ethylene glycol produced by the microorganisms and according to the methods described herein. For example, the composition comprising ethylene glycol may be an antifreeze, preservative, dehydrating agent, or drilling fluid.

The disclosure also provides polymers comprising ethylene glycol produced by the microorganisms and according to the methods described herein. Such polymers may be, for example, homopolymers such as polyethylene glycol or copolymers such as polyethylene terephthalate. Methods for the synthesis of these polymers are well-known in the art. See, e.g., Herzberger et al., *Chem Rev.*, 116(4): 2170-2243 (2016) and Xiao et al., *Ind Eng Chem Res.* 54(22): 5862-5869 (2015).

The disclosure further provides polyethylene glycol conjugates. In some embodiments, polyethylene glycol (PEG) conjugates include PEG conjugated to a biopharmaceutical, proteins, antibodies, anticancer drugs, or any combination thereof. In other embodiments, the PEG conjugate is diethyl terephthalate (DET). In some embodiments, the PEG conjugate is dimethoxyethane.

The disclosure further provides compositions comprising polymers comprising ethylene glycol produced by the microorganisms and according to the methods described herein. For example, the composition may be a fiber, resin, film, or plastic.

In one embodiment, ethanol or ethyl alcohol produced according to the method of the disclosure may be used in numerous product applications, including antiseptic hand rubs (WO 2014/100851), therapeutic treatments for methylene glycol and methanol poisoning (WO 2006/088491), as a pharmaceutical solvent for applications such as pain medication (WO 2011/034887) and oral hygiene products (U.S. Pat. No. 6,811,769), as well as an antimicrobial preservative (U.S. Patent Application No. 2013/0230609), engine fuel (U.S. Pat. No. 1,128,549), rocket fuel (U.S. Pat.

No. 3,020,708), plastics, fuel cells (U.S. Pat. No. 2,405,986), home fireplace fuels (U.S. Pat. No. 4,692,168), as an industrial chemical precursor (U.S. Pat. No. 3,102,875), cannabis solvent (WO 2015/073854), as a winterization extraction solvent (WO 2017/161387), as a paint masking product (WO 1992/008555), as a paint or tincture (U.S. Pat. No. 1,408,091), purification and extraction of DNA and RNA (WO 1997/010331), and as a cooling bath for various chemical reactions (U.S. Pat. No. 2,099,090). In addition to the foregoing, the ethanol generated by the disclosed method may be used in any other application for which ethanol might otherwise be applicable.

In an additional embodiment, isopropanol or isopropyl alcohol (IPA) produced according to the method may be used in numerous product applications, including either in isolation or as a feedstock for the production for more complex products. Isopropanol may also be used in solvents for cosmetics and personal care products, de-icers, paints and resins, food, inks, adhesives, and pharmaceuticals, including products such as medicinal tablets as well as disinfectants, sterilisers and skin creams.

The IPA produced may be used in the extraction and purification of natural products such as vegetable and animal oil and fats. Other applications include its use as a cleaning and drying agent in the manufacture of electronic parts and metals, and as an aerosol solvent in medical and veterinary products. It can also be used as a coolant in beer manufacture, a coupling agent, a polymerisation modifier, a de-icing agent and a preservative.

Alternatively, the IPA produced according to the method of the disclosure may be used to manufacture additional useful compounds, including plastics, derivative ketones such as methyl isobutyl ketone (MIBK), isopropylamines and isopropyl esters. Still further, the IPA may be converted to propylene according to the following formula:

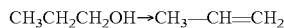

$$CH_3CH_2CH_2OH \rightarrow CH_3-CH=CH_2$$

The propylene produced may be used as a monomer base for the production of various polypropylene oligomers by way of chain-growth polymerization via either gas-phase or bulk reactor systems. The most common catalysts consist of titanium (III) chloride, the so-called Ziegler-Natta catalysts and metallocene catalysts.

Polypropylene oligomers so produced may be classified according to tacticity and can be formed into numerous products by either extrusion or molding of polypropylene pellets, including piping products, heat-resistant articles such as kettles and food containers, disposable bottles (including plastic bottles), clear bags, flooring such as rugs and mats, ropes, adhesive stickers, as well as foam polypropylene which can be used in building materials. Polypropylene may also be used for hydrophilic clothing and medical dressings.

In an embodiment, the tandem repeat protein is squid ring teeth (SRT) protein. In an embodiment, the tandem repeat protein is an insect silk protein. In some embodiments, the tandem repeat protein is used in the manufacture of personal care products, textiles, plastics, biomedical products, or any combination thereof. In another embodiment, the tandem repeat protein comprises at least one polypeptide of the disclosure, a silk fiber and/or a copolymer of the disclosure, one or more acceptable carriers, or any combination thereof. In one embodiment, a product further comprises a drug. In another embodiment, a product is used as a medicine, in a medical device, a cosmetic, or any combination thereof. In an embodiment, the tandem repeat protein comprises a silk fiber, a copolymer, a drug, used for the manufacture of a medicament for treating or preventing a disease. In some embodiments, the tandem repeat proteins, fibers, copolymers, or any combination thereof can be used for a broad and diverse array of medical, military, industrial and commercial applications. In an embodiment, tandem repeat proteins can be used in the manufacture of medical devices comprising sutures, skin grafts, cellular growth matrices, replacement ligaments, surgical mesh, or any combination thereof. In other embodiments, the tandem repeat proteins can be used in industrial and commercial products comprising cable, rope, netting, fishing line, clothing fabric, bullet-proof vest lining, container fabric, backpacks, knapsacks, bag or purse straps, adhesive binding material, non-adhesive binding material, strapping material, tent fabric, tarpaulins, pool covers, vehicle covers, fencing material, sealant, construction material, weatherproofing material, flexible partition material, sports equipment, or any combination thereof. In an embodiment, the tandem repeat proteins can be used in any fiber or fabric for which high tensile strength and elasticity are desired. In an embodiment, the tandem repeat proteins may be used in a native form, a modified form, a derivative form, or any combination thereof. In some embodiments, the tandem repeat proteins can be spun together and/or bundled or braided with other fiber types. The present disclosure contemplates that the production of such combinations of the disclosure can be readily practiced to enhance any desired characteristics, including but not limited to appearance, softness, weight, durability, water-repellent properties, improved cost-of-manufacture, that may be generally sought in the manufacture and production of fibers for medical, industrial, or commercial applications. In some embodiments, the tandem repeat proteins are cosmetic and skin care compositions comprising anhydrous compositions having an effective amount of tandem repeat protein in a cosmetically acceptable medium. In an embodiment, the compositions include, but are not limited to, skin care, skin cleansing, make-up, anti-wrinkle products, or any combination thereof. In another embodiment, the composition comprises beauty soap, facial wash, shampoo, rinse, hair dye, hair cosmetics, general cream, emulsion, shaving cream, conditioner, cologne, shaving lotion, cosmetic oil, facial mask, foundation, eyebrow pencil, eye cream, eye shadow, mascara, perfume, tanning and sunscreen cosmetics, sunscreen lotion, nail cosmetics, eyeliner cosmetics, lip cosmetics, oral care products, toothpaste, or any combination thereof. In another embodiment, the tandem repeat protein is used in a coating on a bandage to promote wound healing, bandage material, a porous cloth, or any combination thereof. In an embodiment, the tandem repeat protein may be used in a film comprising a wound dressing material, an amorphous film, or any combination thereof.

In one embodiment the tandem repeat protein is used in a stent, a stent graft, or any combination thereof. In an embodiment, the tandem repeat protein may be used in a thread, a braid, a sheet, a powder, or any combination thereof. In an embodiment, the stent graft may contain a coating on some or all of the tandem repeat protein, where the coating degrades upon insertion of the stent graft into a host, the coating thereby delaying contact between the tandem repeat protein and a host. Suitable coatings include, without limitation, gelatin, degradable polyesters (e.g., PLGA, PLA, MePEG-PLGA, PLGA-PEG-PLGA, and copolymers and blends thereof), cellulose and cellulose derivatives (e.g., hydroxypropyl cellulose), polysaccharides (e.g., hyaluronic acid, dextran, dextran sulfate, chitosan), lipids, fatty acids, sugar esters, nucleic acid esters, polyanhydrides, polyorthoesters and polyvinyl alcohol (PVA). In one embodiment, the tandem repeat protein containing stent grafts may contain a biologically active agent (drug), where the agent is released from the stent graft and then induces an enhanced cellular response (e.g., cellular or extracellular matrix deposition) and/or fibrotic response in a host into which the stent graft has been inserted. In some embodiments, the tandem repeat protein may also be used in a matrix for producing ligaments and tendons ex vivo. In an embodiment the tandem repeat protein is used in a hydrogel. In an embodiment, the tandem repeat proteins of the disclosure may be applied to the surface of fibers for use in textiles. In an embodiment, the fiber materials include, but are not limited to textile fibers of cotton, polyesters such as rayon and Lycra™, nylon, wool, and other natural fibers including native silk. In some embodiments, compositions suitable for applying the silk protein onto the fiber may include co-solvents such as ethanol, isopropanol, hexafluoranols, isothiocyanouranates, and other polar solvents that can be mixed with water to form solutions or microemulsions. The tandem repeat protein-containing solution may be sprayed onto the fiber or the fiber may be dipped into the solution. In some embodiments, flash drying of the coated material is utilized. In another embodiment, the tandem repeat protein composition is applied onto woven fibers. In one embodiment, the tandem repeat protein is used to coat stretchable weaves comprising stretchable clothing, stockings, or any combination thereof. In an embodiment, the tandem repeat protein can be added to polyurethane, other resins or thermoplastic fillers to prepare panel boards and other construction material or as moulded furniture and benchtops that replace wood and particle board. In an embodiment, the composites can also be used in building and automotive construction especially rooftops and door panels. In other embodiments, the tandem repeat proteins fibers re-enforce the resin making the material much stronger, including light weight construction which is of equal or superior strength to other particle boards and composite materials. In some embodiments, tandem repeat protein fibers are isolated and added to a synthetic composite-forming resin to be used in combination with plant-derived proteins, starch and oils to produce a biologically-based composite materials. In an embodiment, the tandem repeat protein is a paper additive. In another embodiment, the tandem repeat protein is used in technical and intelligent textiles. In some embodiments, the technical and intelligent textiles do not change properties when wet and maintain their strength and extensibility. In one embodiment, the tandem repeat proteins are used for functional clothing for sports and leisure wear, work wear, protective clothing, or any combination thereof. In some embodiments, the tandem repeat protein is used in clothing, equipment, materials for durability to prolonged exposure, heavy wear, personal protection from external environment, resistance to ballistic projectiles, resistant to fire and chemicals, or any combination thereof.

In one embodiment, ethylene is used to produce butadiene. In some embodiments the butadiene is used in rubber tires.

In an embodiment, a method for the continuous production of ethylene, the process comprising: passing a gaseous substrate to a bioreactor containing a culture of a recombinant C1-fixing microorganism capable of producing ethylene in a culture medium such that the microorganism converts the gaseous substrate to ethylene; and recovering the ethylene from the bioreactor.

In other embodiments, converting the ethylene into a component used to manufacture tires. In an embodiment, the ethylene is converted into a component used in tire threads.

The method according to an embodiment, wherein the tires are end-of-life tires.

The method according to an embodiment, wherein the gaseous substrate is derived from a process comprising tires.

The method according to an embodiment, wherein the gaseous substrate is derived from a product circularity process or a sustainable chemical process.

The method according to an embodiment, further comprising converting the ethylene to a component used to manufacture new tires.

The method according to an embodiment, comprising resin components selected from ethylene and other olefins bonded to synthetic components selected from butadiene and isoprene to form hybrid polymers used to manufacture tires.

One embodiment is directed to a method for producing a polymer from a gaseous substrate comprising a first gas fermentation process produces at least one first product selected from butadiene, isoprene, conjugated dienes, or any combination thereof and a second gas fermentation process produces at least one second product selected from ethylene and olefins, or any combination thereof, and wherein the at least one first product and at least one second product are copolymerized to form a polymer.

The method according to an embodiment, wherein the first gas fermentation process and the second gas fermentation process are run in parallel.

The method according to an embodiment, wherein the first gas fermentation process and the second gas fermentation process are both run continuously.

The method according to an embodiment, comprising a first gas fermentation process produces rubber component and a second gas fermentation process produces a resin component, and wherein the rubber component and resin component are copolymerized to form a polymer.

The method according to an embodiment, wherein the rubber component and resin component are copolymerized by a suitable polymerization catalyst.

The method according to an embodiment, wherein the rubber component is selected from butadiene, isoprene, conjugated dienes, or any combination thereof.

The method according to an embodiment, wherein the resin component is selected from ethylene, olefins, or any combination thereof.

The method according to an embodiment, wherein the suitable polymerization catalyst further comprises another component contained in a general polymerization catalyst composition containing a metallocene complex.

The method according to an embodiment, wherein the metallocene complex is a complex compound having one or more cyclopentadienyl groups or derivative cyclopentadienyl groups bonded to a central metal.

The method according to an embodiment, wherein the central metal is selected from a lanthanoid element, scandium, yttrium, or any combination thereof.

The method according to an embodiment, wherein the central metal is selected from samarium (Sm), neodymium (Nd), praseodymium (Pr), gadolinium (Gd), cerium (Ce), holmium (Ho), scandium (Sc), and yttrium (Y).

The method according to an embodiment, further comprising converting the polymer into a tire.

One embodiment for the circular production of tires from a gaseous substrate is directed to a first gas fermentation process to produce at least one first product selected from butadiene, isoprene, conjugated dienes, or any combination thereof; and a second gas fermentation process to produce at least one second product selected from ethylene and olefins, or any combination thereof, wherein the at least one first product and at least one second product are copolymerized to form a polymer, and wherein the substrate is derived from a process comprising tires.

The method according to an embodiment, wherein the substrate is derived from a process comprising end-of-life tires.

One embodiment is directed to a method for the circular production of tires, the method comprising: 1) passing a gaseous substrate to a first bioreactor containing a culture of a recombinant C1-fixing microorganism capable of producing at least one first product selected from butadiene, isoprene, conjugated dienes, or any combination thereof in a culture medium such that the microorganism converts the gaseous substrate to the at least one first product; and recovering the at least one first product from the bioreactor; 2) passing a gaseous substrate to a second bioreactor containing a culture of a recombinant C1-fixing microorganism capable of producing at least one second product selected from ethylene and olefins, or any combination thereof in a culture medium such that the microorganism converts the gaseous substrate to the at least one second product; and recovering the at least one second product from the bioreactor; 3) polymerizing the at least one first product with the at least one second product in the presence of a suitable polymerization catalyst to form a hybrid polymer; and 4) converting the hybrid polymer into a tire.

The method according to an embodiment, wherein the suitable polymerization catalyst further comprises another component contained in a general polymerization catalyst composition containing a metallocene complex.

The method according to an embodiment, wherein the metallocene complex is a complex compound having one or more cyclopentadienyl groups or derivative cyclopentadienyl groups bonded to a central metal.

The method according to an embodiment, wherein the central metal is selected from a lanthanoid element, scandium, yttrium, or any combination thereof.

The method according to an embodiment, wherein the central metal is selected from samarium (Sm), neodymium (Nd), praseodymium (Pr), gadolinium (Gd), cerium (Ce), holmium (Ho), scandium (Sc), and yttrium (Y).

The method according to an embodiment, wherein the first bioreactor and the second bioreactor are run in parallel.

The method according to an embodiment, wherein both the first bioreactor and the second bioreactor are continuously operated.

The method according to an embodiment, wherein the substrates are derived from a process comprising end-of-life tires.

The method according to an embodiment further comprising converting the isoprenoid into a product selected from synthetic rubber, block polymers containing styrene, thermoplastic rubbers, pressure-sensitive or thermosetting adhesives, butyl rubber, terpenes selected from citral, linalool, ionones, myrcene, L-menthol, N,N-diethylnerylamine, geraniol, nerolidols, flavours, fragrances, fuel additive, plastics, polyisoprene, The method according to an embodiment further comprising converting the butadiene into a product selected from styrene-butadiene rubber, synthetic rubber, tires, component of tires, thermoplastic rubber, shoes, shoe soles, adhesives, sealants, asphalt, polymer modification components, nylon, ABS resins, chloroprene/neoprene rubber, nitrile rubber, plastics, acrylics, acrylonitrile-butadiene-styrene resins, and synthetic elastomers.

One embodiment is directed to a method for chemical recycling, the method comprising: a pyrolysis, gasification, and/or partial oxidation process; provided to a gas fermentation process; provided to a chemical product manufacturing process to produce a product comprising butadiene, isoprenoid, ethylene, polyethylene terephthalate (PET), or any combination thereof; provided to a synthetic rubber production process; provided to a tire manufacturing process; provided to a process of using tires; provided a process for the collecting and shredding of used tires; and provided back to the pyrolysis, gasification, and/or partial oxidation process.

One embodiment is directed to a method for chemical recycling, the method comprising: 1) a pyrolysis, gasification, and/or partial oxidation process; 2) provided to a gas fermentation process; 3) provided to a chemical product manufacturing process to produce a product comprising butadiene, isoprenoid, ethylene, polyethylene terephthalate (PET), or any combination thereof; 4) provided to a synthetic rubber production process; 5) provided to a tire manufacturing process; 6) provided to a process of using tires; 7) provided a process for the collecting and shredding of used tires; and 8) provided back to the pyrolysis, gasification, and/or partial oxidation process.

One embodiment is directed to a method for chemical recycling, the method comprising: 1) a pyrolysis, gasification, and/or partial oxidation process; 2) provided to a gas fermentation process; 3) provided to a chemical product manufacturing process to produce a commodity product; 4) provided to a synthetic rubber production process; 5) provided to a tire manufacturing process; 6) provided to a process of using tires; 7) provided a process for the collecting and shredding of used tires; and 8) provided back to the pyrolysis, gasification, and/or partial oxidation process.

Another embodiment is directed to a method for chemical recycling, the method comprising: 1) a pyrolysis, gasification, and/or partial oxidation process producing an effluent stream; 2) passing the effluent stream to a gas fermentation process to produce a product; 3) passing the gas fermentation product to a chemical product manufacturing process to produce a commodity product; 4) passing the commodity product to a synthetic rubber production process to produce synthetic rubber; 5) passing the synthetic rubber product to a tire manufacturing process to produce a tire; 6) providing the tire to a process of using tires; 7) passing the used tires to a process for the collecting and shredding of used tires; and 8) recycling used tires back to the pyrolysis, gasification, and/or partial oxidation process.

One embodiment is directed to a process for continuous co-production of at least one chemical product and at least one heterologous protein product comprising:
g) providing a continuous bioreactor;
h) introducing to the bioreactor a recombinant C1-fixing microorganism capable of co-producing at least one chemical product and at least one heterologous protein, a gaseous substrate comprising one or more of CO, $CO_2$, and $H_2$, and a liquid growth medium;
i) continuously culturing the recombinant C1-fixing microorganism thereby generating a gas fermentation broth comprising 1) the at least one chemical product, 2) the at least one heterologous protein product, and 3) microbial biomass;
j) continuously removing a portion of the gas fermentation broth in a first stream;

k) continuously removing the at least one chemical product in a second stream; and l) continuously recovering the at least one heterologous protein from the microbial biomass from the first stream.

Another embodiment is directed to a method for the continuous co-production of at least one targeted chemical product and at least one heterologous protein product, the method comprising: a) culturing a recombinant C1-fixing microorganism capable of co-production of at least one targeted chemical product and at least one heterologous protein in the presence of a gaseous substrate comprising one or more of CO, $CO_2$, and $H_2$, wherein the culturing is a continuous fermentation process; and wherein the substrate and liquid nutrient medium of the culture are non-coalescing.

One embodiment is directed to a method for continuous co-production of at least one targeted chemical product and at least one heterologous protein product, the method comprising: a) culturing in a state of a continuous gas fermentation process, a recombinant C1-fixing microorganism capable of co-production of at least one targeted chemical product and at least one heterologous protein in a fermentation broth comprising the microorganism, a gaseous substrate comprising one or more of CO, $CO_2$, and $H_2$, and a liquid growth medium, wherein the fermentation broth comprises an equilibrium surface tension of from about 30 to about 40 mN/m.

Another embodiment is directed to a method for continuous co-production of at least one targeted chemical product and at least one heterologous protein product, the method comprising: a) culturing in a bioreactor, a recombinant C1-fixing microorganism capable of co-production of at least one targeted chemical product and at least one heterologous protein having a unit value in the presence of a gaseous substrate comprising one or more of CO, $CO_2$, and $H_2$, and a liquid growth medium; and recovering the at least one targeted chemical product and the at least one heterologous protein wherein the at least one heterologous protein is recovered in an amount from about 0.1% to about 1% grams/dry cell weight/day of the at least one heterologous protein produced.

The method of an embodiment, further comprising an initial stage of gas fermentation wherein the initial surface tension of the broth is from about 60 to about 72 mN/m.

The method of an embodiment, wherein the heterologous protein has a high market value.

The method of an embodiment, wherein the heterologous protein is a high-value, specialized protein.

The method of an embodiment, wherein the heterologous protein is an antioxidant enzyme.

The method of an embodiment, wherein the antioxidant enzyme is selected from catalase, glutathione peroxidase, vitamin C, vitamin E, beta-carotene, carotenoids, flavonoids, superoxide dismutase, or any combination thereof.

The method of an embodiment, wherein the antioxidant enzyme is superoxide dismutase.

The method of an embodiment, wherein the antioxidant enzyme is a superoxide dismutase selected from SOD006, SOD007, SOD009, and SOD010.

The method of an embodiment, wherein the at least one heterologous protein is squid ring teeth (SRT) protein and the at least one chemical product is ethylene.

The method of an embodiment, wherein the at least one chemical product is ethylene.

The method of an embodiment, further comprising separating the microbial biomass from the first stream before recovering the heterologous protein.

One embodiment is directed to a method for continuous co-production of at least one targeted chemical product and at least one exogenous protein product, the method comprising: a) culturing, in a bioreactor, a recombinant C1-fixing microorganism capable of co-production of at least one targeted chemical product and at least one heterologous protein in the presence of a gaseous substrate comprising one or more of CO, $CO_2$, and $H_2$, and a liquid growth medium; b) generating microbial biomass having a unit value, at least one targeted chemical product, and at least one heterologous protein having a unit value, wherein the unit value of the heterologous protein is greater than the unit value of the microbial biomass; and c) recovering the at least one heterologous protein in an amount of at least 15% of a sum value of the unit value of the heterologous protein and the unit value of the microbial biomass.

The method of an embodiment, wherein recovering of step c) of the at least one heterologous protein is in an amount of at least 1% of the sum value.

The method of an embodiment, wherein a protein or chemical is selected from bilirubin, glutathione, lipoic acid, N-acetyl cysteine, NADPH, NADH, ubiquinone, coenzyme Q10, uric acid, copper/zinc and manganese-dependent superoxide dismutase, iron-dependent catalase, selenium-dependent glutathione peroxidase, vitamin C, vitamin E, beta carotene, lycopene, lutein, flavonoids, flavones, flavonols, proanthocyanidins, albumin, ceruloplasmin, metallothionein, ferritin, myoglobin, transferrin, haptoglobins, ceruloplasmin, heat shock proteins, or any combination thereof.

The method of an embodiment, wherein the high-value, specialized protein is selected from ubiquinone, coenzyme Q10, copper/zinc and manganese-dependent superoxide dismutase, iron-dependent catalase, selenium-dependent glutathione peroxidase, albumin, ceruloplasmin, metallothionein, ferritin, myoglobin, transferrin, haptoglobins, ceruloplasmin, heat shock proteins, or any combination thereof.

The method of an embodiment, wherein the at least one chemical product is selected from 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, ketoadipic acid, 1,3-hexanediol, 3-methyl-2-butanol, 2-buten-1-ol, isovalerate, isoamyl alcohol, monoethylene glycol, or any combination thereof.

The method of an embodiment, further comprising the recombinant microorganism comprising a disruptive mutation in one or more genes.

The method of an embodiment, wherein the recombinant microorganism comprises a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides, Cupriavidus necator* and *Thermoanaerobacter kivui*.

The method of an embodiment, wherein the chemical product is one or more of ethylene, ethanol, acetone, isopropanol, or any combination thereof.

The method of an embodiment, further comprising a microbial biomass and at least one excipient.

The method of an embodiment, wherein the microbial biomass is suitable as animal feed.

The method of an embodiment, wherein the at least one heterologous protein is superoxide dismutase and the at least one chemical product is ethylene.

One embodiment is directed to a genetically engineered microorganism capable of producing a commodity chemical product, a tandem repeat protein product, microbial biomass, single cell protein (SCP), one or more intermediates, or any combination thereof.

In some aspects, the microbial biomass has a unit value. In one embodiment, the microbial biomass has a market value.

The microorganism according to an embodiment, wherein the microorganism produces a heterologous protein product, wherein the microorganism comprises a heterologous nucleic acid encoding at least one protein having tandem repeats.

The microorganism according to an embodiment, wherein the microorganism comprises a genetically engineered microorganism capable of co-producing at least one heterologous protein and at least one secreted chemical product from a gaseous substrate, the microorganism comprising a heterologous nucleic acid encoding the at least one protein having tandem repeats and a heterologous nucleic acid encoding the at least one secreted chemical product, wherein the microorganism is a C1-fixing bacteria.

The microorganism according to an embodiment, wherein the microorganism comprises a genetically engineered microorganism capable of co-producing at least one heterologous protein and at least one secreted chemical product from a gaseous substrate, the microorganism comprising a heterologous nucleic acid encoding the at least one protein having one or more tandem repeats and a heterologous nucleic acid encoding the at least one secreted chemical product, wherein the microorganism is a C1-fixing bacteria.

The microorganism according to an embodiment, wherein the microorganism comprises a genetically engineered C1-fixing microorganism capable of co-producing an heterologous protein and a chemical product from a gaseous substrate, the microorganism comprising a heterologous nucleic acid encoding the at least one heterologous protein having one or more tandem repeats and a heterologous nucleic acid encoding the at least one chemical product.

The microorganism according to an embodiment, wherein the microorganism comprises a genetically engineered C1-fixing microorganism capable of co-producing an heterologous protein and a chemical product from a gaseous substrate, the microorganism comprising a heterologous nucleic acid encoding the at least one heterologous protein having one or more tandem repeats and a heterologous nucleic acid encoding the at least one chemical product, wherein the microorganism is capable of accumulating the at least one heterologous protein in the cell and secreting the at least one chemical product from the cell.

The microorganism according to an embodiment, wherein the microorganism comprises one or more heterologous enzymes are derived from a genus selected from the group consisting of *Bacillus, Clostridium, Cupriavidus, Escherichia, Gluconobacter, Hyphomicrobium, Lysinibacillus, Paenibacillus, Pseudomonas, Sedimenticola, Sporosarcina, Streptomyces, Thermithiobacillus, Thermotoga,* and *Zea.*

The microorganism according to an embodiment, wherein the microorganism comprises a genetically engineered C1-fixing microorganism capable of co-producing at least one heterologous functional protein and at least one chemical product having two or more carbons from a gaseous substrate, the microorganism comprising a heterologous nucleic acid encoding at least one protein having tandem repeats and a heterologous nucleic acid encoding at least one secreted chemical product.

The microorganism according to an embodiment, wherein the microorganism comprises a genetically engineered C1-fixing microorganism capable of co-producing at least one heterologous functional protein and at least one chemical product having two or more carbons from a gaseous substrate, the microorganism comprising a heterologous nucleic acid encoding a group of genes comprising at least one protein having tandem repeats and at least one secreted chemical product.

The microorganism according to an embodiment, a genetically engineered microorganism capable of co-producing at least one heterologous protein and at least one chemical product from a gaseous substrate, the microorganism comprising a heterologous nucleic acid encoding the at least one protein having one or more tandem repeats and a heterologous nucleic acid encoding the at least one chemical product, wherein the microorganism is a C1-fixing bacteria.

The microorganism according to an embodiment, wherein the microorganism comprises a genetically engineered C1-fixing microorganism capable of co-producing at least one heterologous protein and at least one chemical product from a gaseous substrate, the microorganism comprising:
  a) a heterologous nucleic acid encoding at least one heterologous protein having one or more tandem repeats; and
  b) a heterologous nucleic acid encoding at least one chemical having two or more carbons, wherein the microorganism is capable of accumulating the at least one heterologous protein in the cell and secreting the at least one chemical product from the cell.

A method according to an embodiment, wherein the method of co-producing at least one heterologous protein and at least one chemical product by culturing the genetically engineered C1-fixing. microorganism in the presence of a gaseous substrate comprising one or more of CO, $CO_2$, and $H_2$, wherein the culturing is a continuous fermentation process.

A method according to an embodiment, the method of co-producing at least one heterologous protein having one or more tandem repeats and at least one chemical product by culturing the genetically engineered microorganism of claim 1 in the presence of a gaseous substrate comprising one or more of CO, $CO_2$, and $H_2$, wherein the culturing is a continuous fermentation process.

The method according to an embodiment, wherein the gaseous substrate comprises a C1-carbon source comprising one or more of CO, $CO_2$, and $H_2$.

The method according to an embodiment, wherein the gaseous substrate comprises syngas or industrial waste gas.

The method according to an embodiment, wherein the method of co-producing at least one heterologous protein having one or more tandem repeats and at least one chemical product by culturing the genetically engineered C1-fixing, wherein the chemical product is one or more of ethylene, ethanol, acetone, isopropanol, or any combination thereof.

The microorganism according to an embodiment, wherein the microorganism comprises a genetically engineered C1-fixing microorganism, wherein the at least one heterologous protein having one or more tandem repeats is selected from collagen, silk, elastin, keratin, resilin, titin, squid ring teeth (SRT) protein, suckerin, or any combination thereof.

The microorganism according to an embodiment, wherein the microorganism is a member of a genus selected from the group consisting of *Acetobacterium, Alkalibaculum, Blautia, Butyribacterium, Clostridium, Cupriavidus, Eubacterium, Moorella, Oxobacter, Ralstonia, Sporomusa,* and *Thermoanaerobacter.*

The microorganism according to an embodiment, wherein the microorganism is derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Cupriavidus necator, Eubacterium limosum, Moorella thermautotrophica, Moorella thermoacetica, Oxobacter pfennigii, Ralstonia eutropha, Sporomusa ovata, Sporomusa silvacetica, Sporomusa sphaeroides,* and *Thermoanaerobacter kiuvi.*

The microorganism according to an embodiment, wherein the microorganism is derived from a parental bacterium selected from the group consisting of *Clostridium autoethanogenum, Clostridium ljungdahlii,* and *Clostridium* ragsdalei.

The microorganism according to an embodiment, wherein the microorganism is derived from a parental bacterium selected from the group consisting of *Cupriavidus necator.*

The microorganism according to an embodiment, wherein the at least one heterologous protein having one or more tandem repeats is selected from silk or SRT protein.

The microorganism according to an embodiment, wherein the gas fermentation product is selected from an alcohol, an acid, a diacid, an alkene, a terpene, an isoprene, and alkyne, or any combination thereof.

The microorganism according to an embodiment, wherein the at least one secreted chemical product is selected from the group 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, keto-adipic acid, 1,3-hexanediol, 3-methyl-2-butanol, 2-buten-1-ol, isovalerate, isoamyl alcohol, or monoethylene glycol.

The microorganism according to an embodiment, wherein the at least one secreted chemical product is selected from 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, keto-adipic acid, 1,3-hexanediol, 3-methyl-2-butanol, 2-buten-1-ol, isovalerate, isoamyl alcohol, monoethylene glycol, or any combination thereof.

The microorganism according to an embodiment, wherein the microorganism further comprising a disruptive mutation in one or more genes.

The microorganism according to an embodiment, wherein the genetically engineered C1-fixing microorganism, further comprising a microbial biomass and at least one excipient.

The microorganism according to an embodiment, wherein the genetically engineered C1-fixing microorganism, wherein the microbial biomass is suitable as animal feed.

The microorganism according to an embodiment, wherein the genetically engineered C1-fixing microorganism, wherein the animal feed is suitable for feeding to one or more of beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents.

The microorganism according to an embodiment, wherein the genetically engineered C1-fixing microorganism, wherein the microorganism is suitable as a single cell protein (SCP).

The microorganism according to an embodiment, wherein the genetically engineered C1-fixing microorganism, wherein the microorganism is suitable as a cell-free protein synthesis (CFPS) platform.

The microorganism according to an embodiment, wherein the genetically engineered C1-fixing microorganism, wherein the at least one secreted chemical product is native to the microorganism.

The microorganism according to an embodiment, wherein the genetically engineered microorganism of claim 1, wherein the at least one heterologous protein is squid ring teeth protein and the at least one chemical product is ethylene.

The microorganism according to an embodiment, wherein the at least one heterologous protein is silk protein and the at least one chemical product is ethylene.

The microorganism according to an embodiment, wherein the at least one chemical product is ethylene.

The method according to an embodiment, wherein the substrate comprises one or more of CO, $CO_2$, and $H_2$.

The method according to an embodiment, wherein at least a portion of the substrate is industrial waste gas, industrial off gas, or syngas.

The method according to an embodiment, wherein both anaerobic and aerobic gases can be used to feed separate cultures (e.g., an anaerobic culture and an aerobic culture) in two or more different bioreactors that are both integrated into the same process stream.

EXAMPLES

The following examples further illustrate the disclosure but, of course, should not be construed to limit its scope in any way.

Example 1: Production of Tandem Repeat Proteins in Autotroph *Clostridium autoethanogenum*

Genes encoding tandem repeat proteins (Table 2) were synthesized and assembled into *Clostridium-E. coli* shuttle vector pMTL8225 (Heap, J Microbiol Methods 78: 79-85, 2009). The gene contains DNA encoding an N-terminal twin-strep tag as a handle for protein detection via Western Blot and/or affinity purification (Schmidt, Protein Expr Purif 92: 54-61, 2013. These vectors have a pre-cloned clostridial promoter and terminator. The promoter sequences are described in Karim et al. Synthetic Biology 2020; 5(1): ysaa019. The resulting plasmids with ermB antibiotic selectable marker. After transformation into *Clostridium*, the sequence-verified strains were subjected to autotrophic growth in 6-well plates.

Protein expression experiments were started in 6-well plates with 3 mL minimal media with yeast extract? and 200 kPa of synthetic gas mix (55% CO, 5% $H_2$, 30% $CO_2$, and 10% $N_2$) and grown at 37° C. until strains reached biomass concentration of 0.20-0.43 gDCW/L. The strains were then subcultured to 0.006-0.03 gDCW/L in 1 L Schott bottles with 200 mL minimal media in the presence of 150 kPa synthetic gas mix (55% CO, 5% $H_2$, 30% $CO_2$, and 10% $N_2$) at 37° C. Biomass concentration was monitored until it reached 0.13-0.32 gDCW/L and then the biomass was harvested for protein detection.

Production of tandem repeat proteins was evaluated by Western blot analysis using anti-Strep tag antibodies. Cultures were lysed and clarified; the clarified lysate and insoluble pellet (resuspended in 5 M urea) were analyzed separately for protein content. Samples were run on Tris-glycine SDS-PAGE, transferred to nitrocellulose membrane, and probed with anti-Strep tag antibody conjugated to alkaline phosphatase for visualization. Protein of the expected size was observed in the insoluble pellet for SRT008, SRT011, SRT012, and SS015. In addition, SS015 was observed in the clarified lysate.

TABLE 2

Tandem repeat proteins expressed in *C. autoethanogenum*.

| SEQ ID NO: | Protein name | Protein description | UniProt ID | Protein reference | Amino acid sequence (size) | Promoter | Codon usage |
|---|---|---|---|---|---|---|---|
| SEQ ID No: 1 | SRT008 | Full length Suckerin-8 from *Dosidicus gigas*, N terminal twin-strep tag | A0A081 DU77 | Guerette ACS Nano 8,7: 7170-7179, 2014 | MWSHPQF EKGGGSGG GSGGSSAW SHPQFEKG GSGGGSGT ATLLFLMS MIAALGCQ SEAAISHGS HVKTVVHH GNGVRTVT HTIHHPVVH HGLHRTSIV PGTTTITHT THDNRHPY GGVTTVTH SNQGAHHP YSFGYGFGG PYGGGGGL YGAPYHMG TTVVNHPG HGMPYPY MYGSQGFG LGGLSGLDY PVGSTVTHS NYGFHHPL GFGEPFNG PYGFQ (22.6 kDa) | Pwl | *C. auto-ethanogenum* |
| SEQ ID No: 2 | SRT012 | Suckerin-8 without signal sequence from *Dosidicus gigas*, N-terminal twin-strep tag | A0A081 DU77 | Guerette ACS Nano 8,7: 7170-7179, 2014 | MWSHPQF EKGGGSGG GSGGSSAW SHPQFEKG GSGGGSGA AISHGSHVK TVVHHGNG VRTVTHTIH HPVVHHGL HRTSIVPGT TTITHTTHD NRHPYGGV TTVTHSNQ GAHHPYSF GYGFGGPY GGGGGLYG APYHMGTT VVNHPGHG MPYPYMYG SQGFGLGG LSGLDYPVG STVTHSNYG FHHPLGFGE PFNGPYGF Q (20.6 kDa) | Pfer | native |

TABLE 2-continued

Tandem repeat proteins expressed in *C. autoethanogenum*.

| SEQ ID NO: | Protein name | Protein description | UniProt ID | Protein reference | Amino acid sequence (size) | Promoter | Codon usage |
|---|---|---|---|---|---|---|---|
| SEQ ID No: 3 | SRT011 | Suckerin-6 without signal sequence from *Dosidicus gigas*, N-terminal twin-strep tag | A0A081 DU74 | Guerette ACS Nano 8,7: 7170-7179, 2014 | MWSHPQF EKGGGSGG GSGGSSAW SHPQFEKG GSGGGSGA FPGFMGGY GGAYPIGSS YSQVTHHG PYGMSGIG GFGGLGYG ASLPVSSVS HVSHGAHY GWGGMYG GGVQVSQS PVMYQGYS VGAPHVQS MGVHYPTT TSVSHSHG GYLGGLGGI GAVGGYGG YGGYGLAG GLGHSVSTV SHGIGHVG MGMGYGY GGFGHY (19.4 kDa) | Pfer | native |
| SEQ ID No: 4 | SS015 | Hornet silk protein Vssilk 2 without signal sequence from *Vespa simillima xanthoptera*, N-terminal twin-strep tag | A9CMG7 | Kambe Acta Biomater 10(8):3590-3598 2014 | MWSHPQF EKGGGSGG GSGGSSAW SHPQFEKG GSGGGSGA SSSSSAESSA SATASSDAS WSASSRSS ATGRAPNVI LNRAPQLG ASAAAIASA RASTSANA ASDEKSARE TRATALARS RAAVTAAA RAAARTQE AVAAAKAA SRAQALAA AKSSAAISAL AAGEAAAQ KADAAALA ALAANQRS VKAAENGL AVQNRANG EAEQASRA AAANLAAAI RTRDNALET RREAARLKA LATAAANA NNKATSLAE ASANQAAE ASSAAEDTS SAQSAAVA QAEAAETL | Pfer | native |

TABLE 2-continued

Tandem repeat proteins expressed in *C. autoethanogenum*.

| SEQ ID NO: | Protein name | Protein description | UniProt ID | Protein reference | Amino acid sequence (size) | Promoter | Codon usage |
|---|---|---|---|---|---|---|---|
| | | | | | NVNLAILES TQSSRQDS NVAKAEAS AAAKASPG TATRDGVN LGLASDAG AAAQLKAQ AAALARASS RISSGPALS AWKWRNE DSSESSTSAI ASSSASSSSS SRSASGN (38.1 kDa) | | |

Example 2: SRT008 and SRT012 Production from Syngas Fermentation in Batch CSTR Tandem repeat protein-containing strains SRT008 and SRT012 (Table 2) were characterized in CSTR under batch mode to characterize protein production and chemical production. Actively growing (early exponential) culture from Schott bottles was used as inoculum for 2 L CSTRs with a synthetic gas blend (55% CO, 5% $H_2$, 30% $CO_2$, and 10% $N_2$) at atmospheric pressure. There was a gas outage during the runs that caused upsets in the culture, ending SRT008 earlier than anticipated.

Figure 3A:
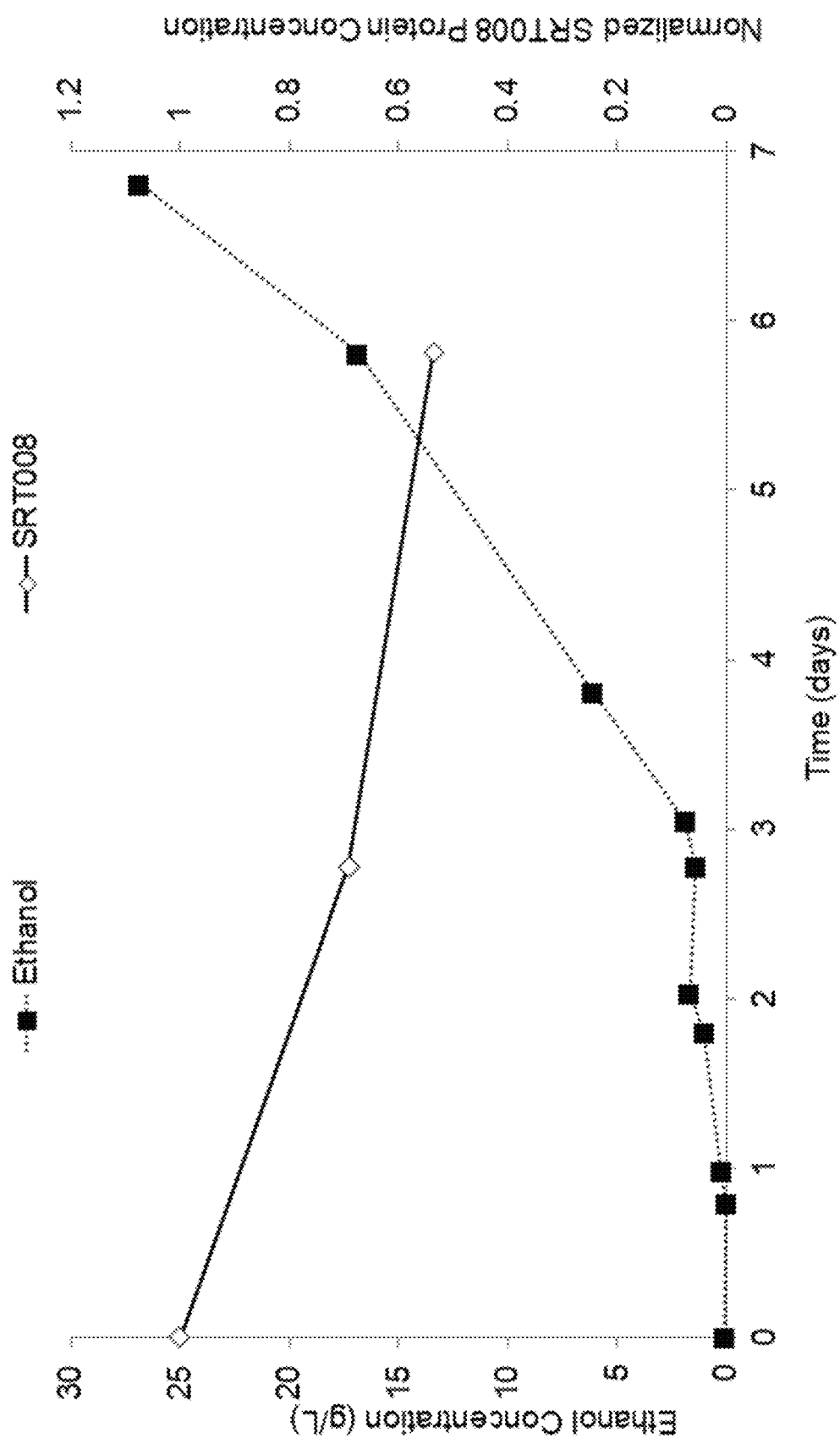
FIGS. 3A-3C show the performance of SRT008 in batch CSTR fermentation using a synthetic gas blend (55% CO, 5% $H_2$, 30% $CO_2$ and 10% $N_2$).
Figure 3B:
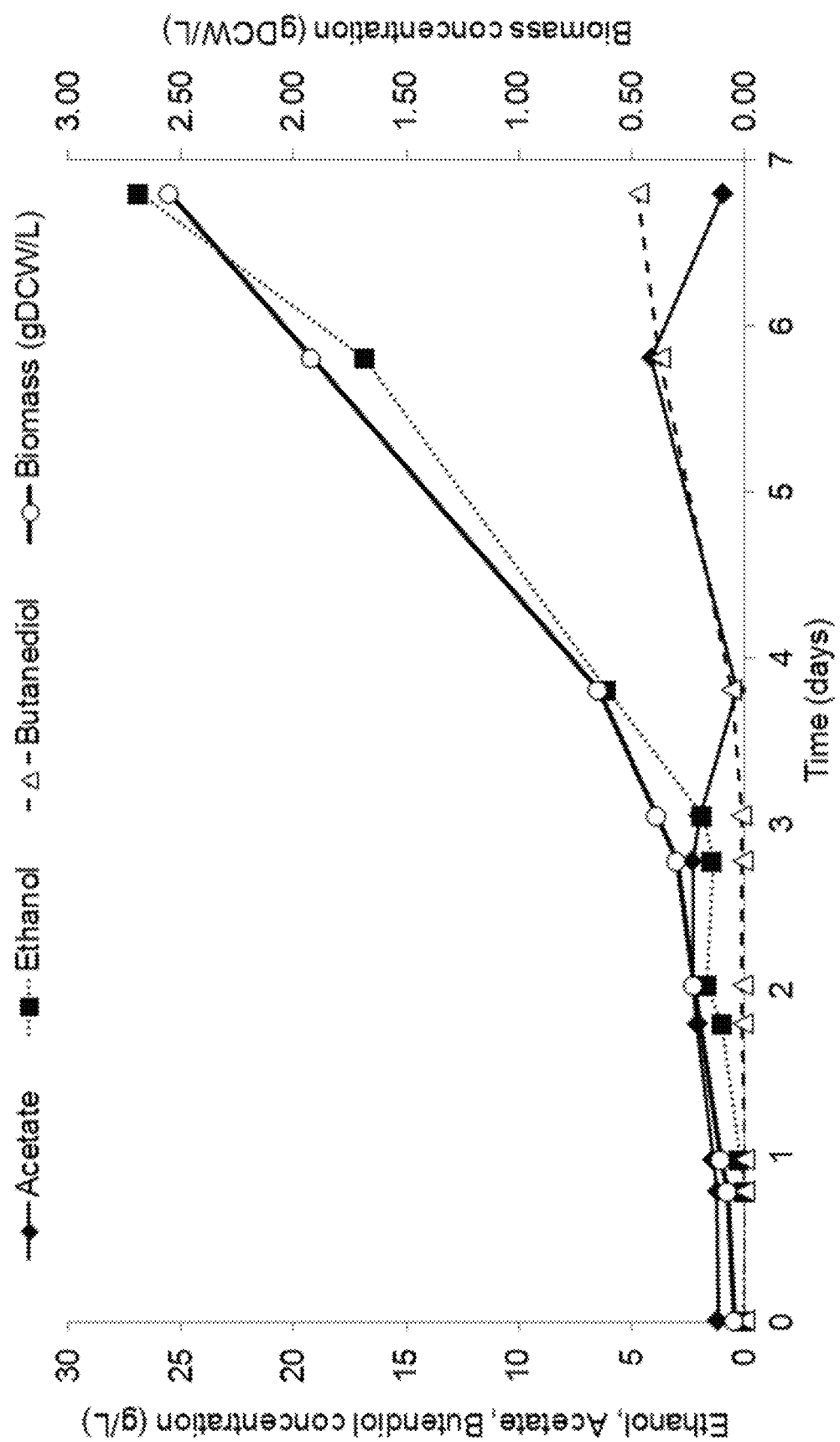
Figure 3C:
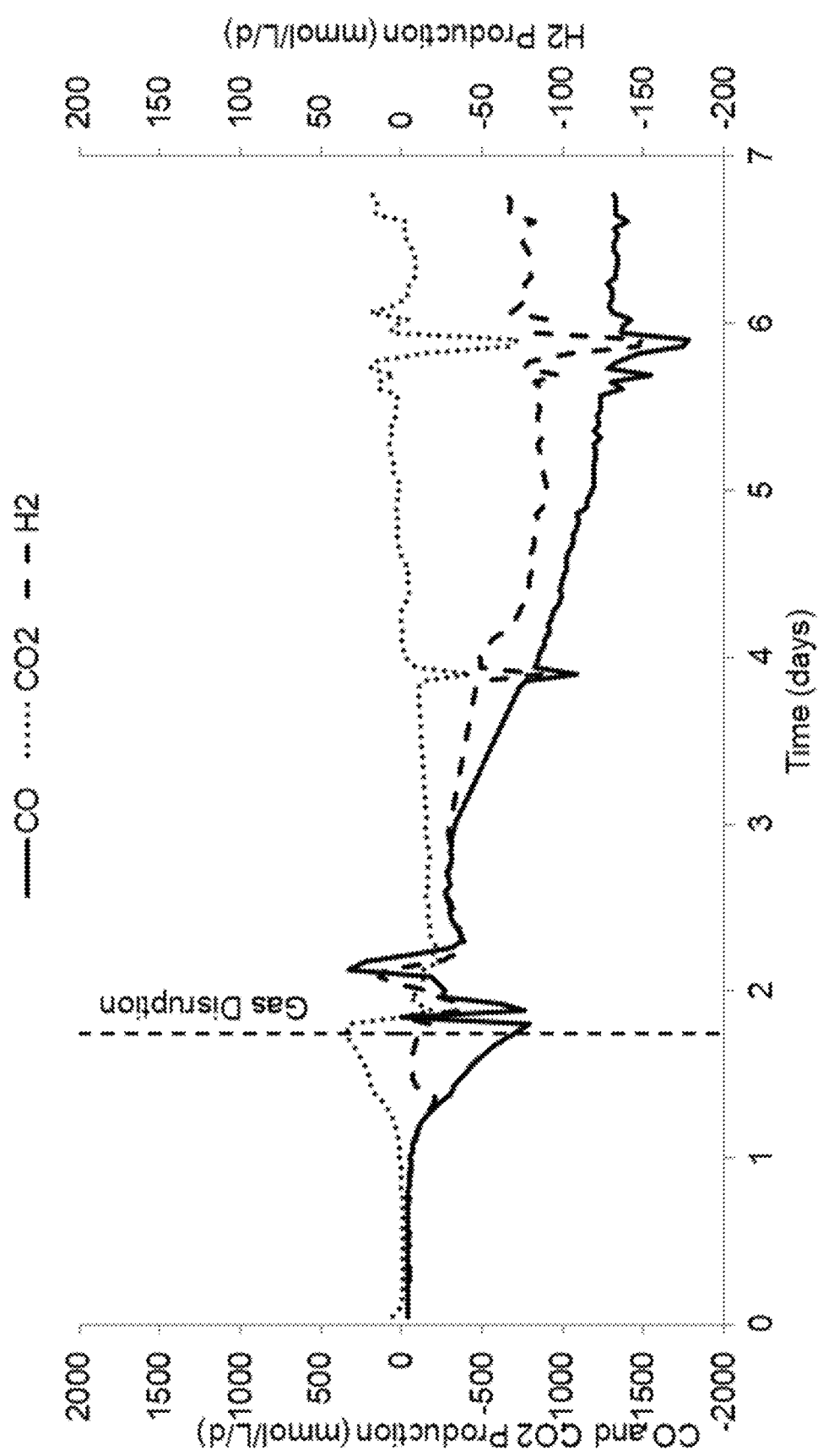

SRT008 achieved a peak biomass concentration of 2.5 gDCW/L (FIG. 3B) and reached a peak CO uptake of 1331 mmol/L/d (FIG. 3C). In addition to a peak ethanol concentration of 26.88 g/L (FIGS. 3A, 3B), this strain reached a peak acetate titer of 4.14 mg/L and peak butanediol titer of 4.73 mg/L (FIG. 3B). SRT008 production was observed via Western blot on days 0, 2.78 and 5.81 with highest relative protein content at day 0.

Figure 4A:
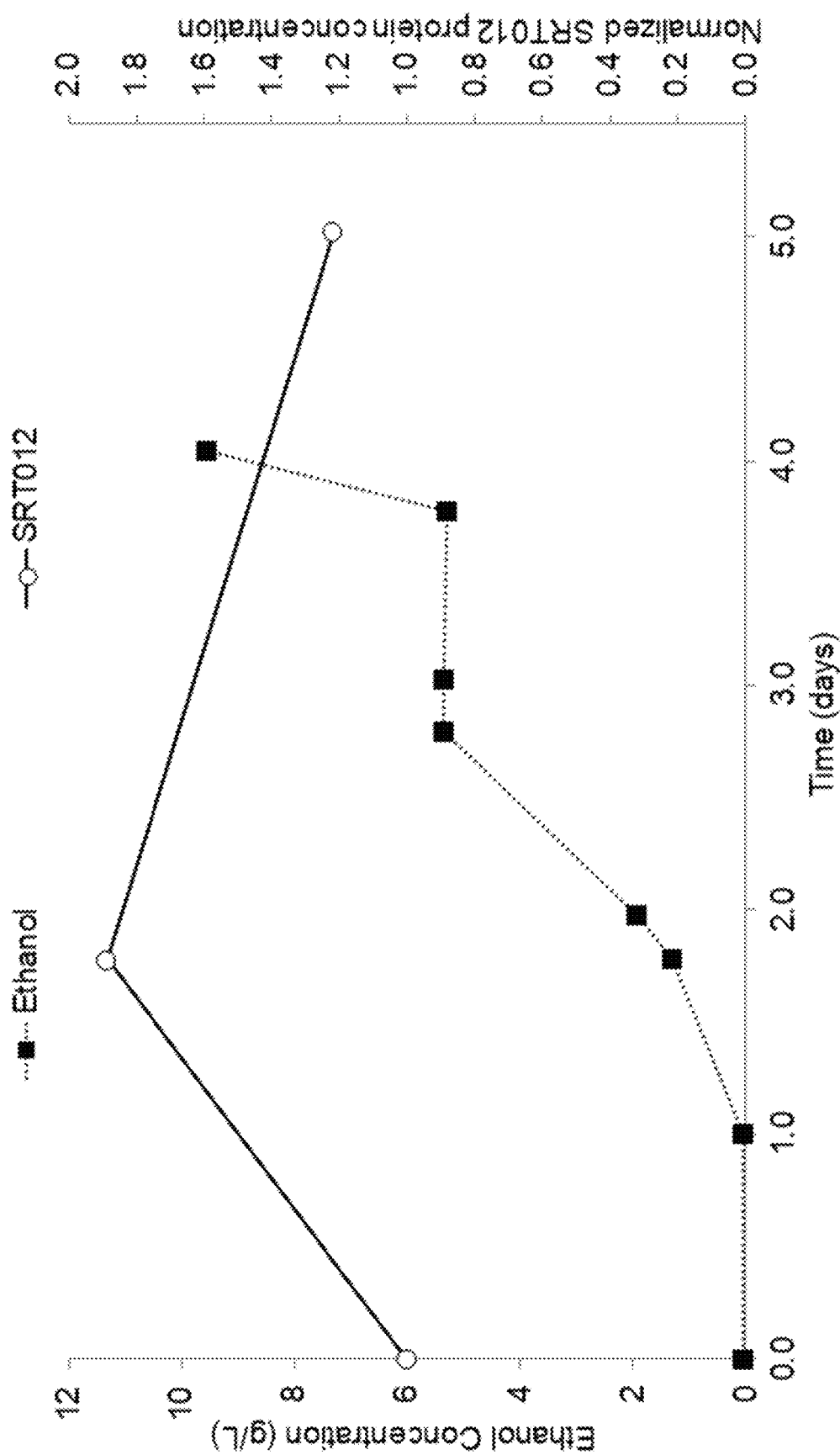
FIGS. 4A-4C show the performance of SRT012 in batch CSTR fermentation using a synthetic gas blend (55% CO, 5% $H_2$, 30% $CO_2$ and 10% $N_2$).
Figure 4B:
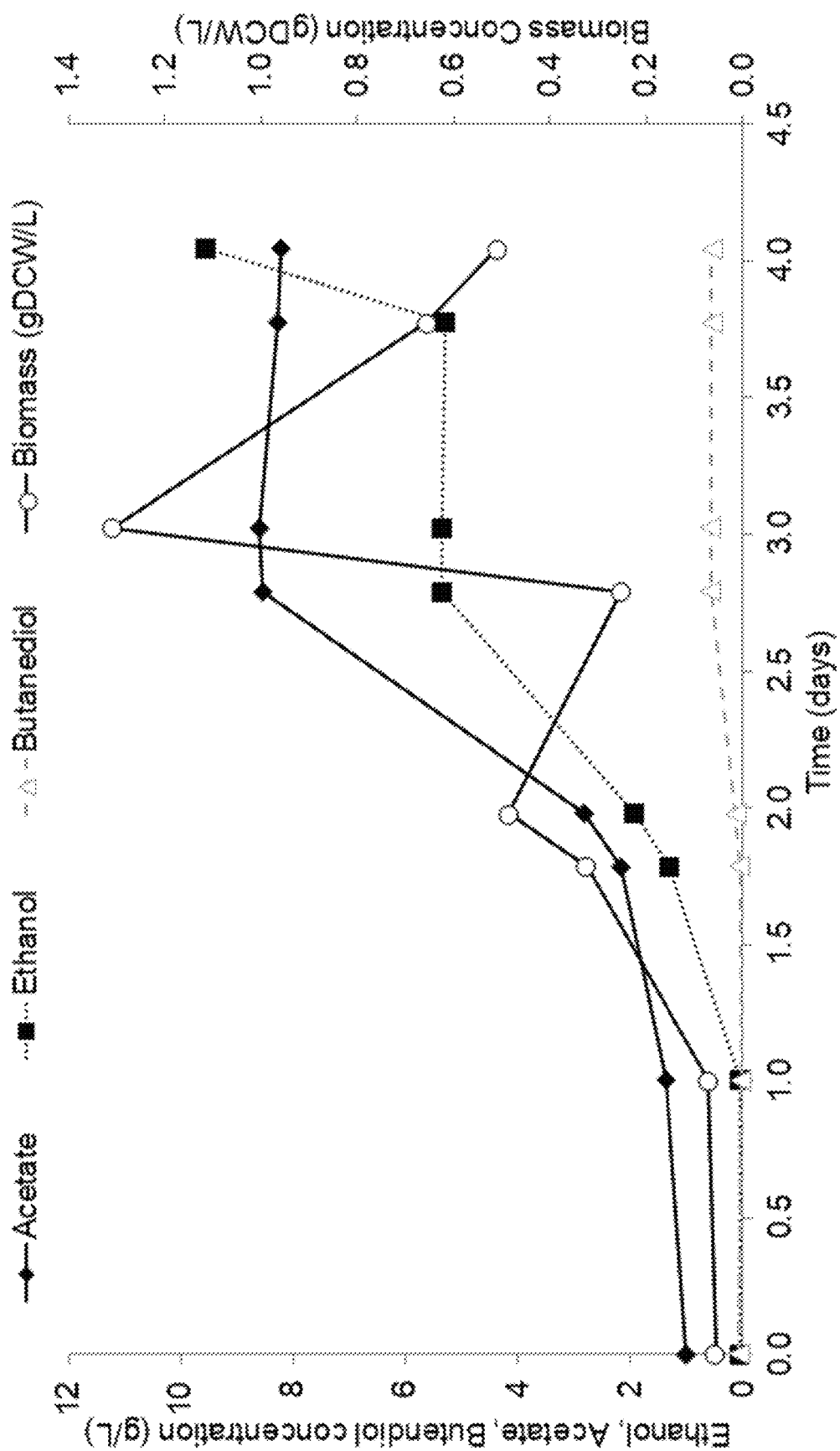
Figure 4C:
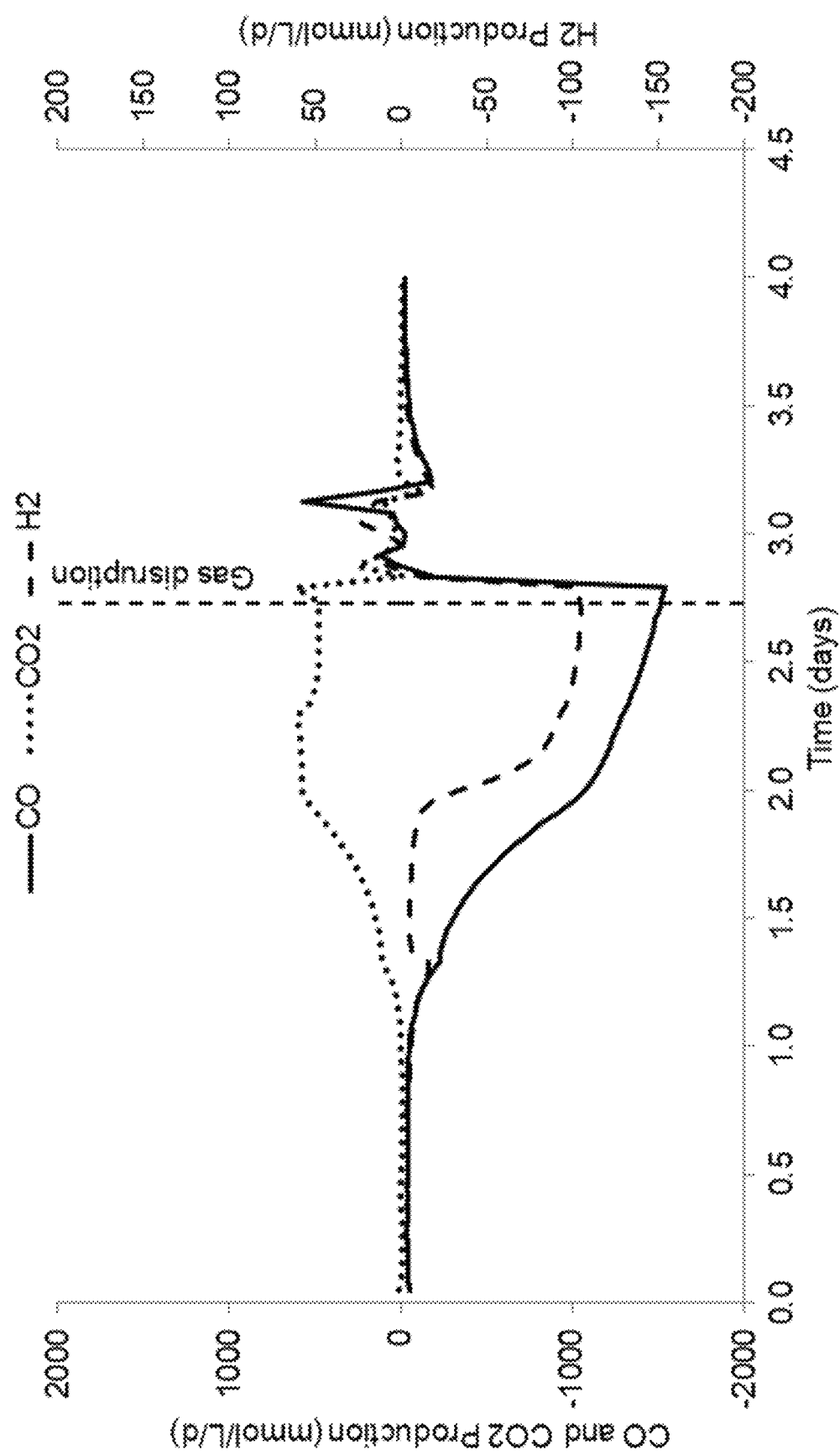

SRT012 achieved a peak biomass concentration of 1.31 gDCW/L (FIG. 4B) and reached a peak CO uptake of 1537 mmol/L/d before having a mechanical issue at day 2.73. In addition to a peak ethanol concentration of 9.57 g/L (FIGS. 4A, 4B), this strain reached a peak acetate titer of 8.27 mg/L and peak butanediol titer of 0.57 mg/L (FIG. 4B). SRT012 production was observed via Western blot on days 0, 1.78, and 5.02 with highest relative protein content at day 1.78 (FIG. 4C). The last data point for protein content per biomass was taken after gas shutoff.

Example 3: SRT012 Production from Syngas Fermentation in Continuous CSTR

Under continuous CSTR conditions using strain SRT012, with using the syn gas mix (55% CO, 5% H2, 30% CO2, and 10% N2), 3 L reactor, and cell recycling membrane (CRM), a dilution (D) rate of 1.2 vessels/day (v/d) was initiated on day 5, before increasing to D of 1.5 v/d on day 12.9, eventually reaching D of 2.5 v/d between day 12.9 and day 60. Biomass concentration accumulated to a peak concentration of 20.85 gDCW/L (FIG. 2B) and CO gas uptake reached a peak of 9300 mmol/L/d (FIG. 2C). This strain had a max concentration of ethanol at 34.82 g/L and max acetate concentration of 11.79 g/L (FIG. 2B).

Figure 2A:
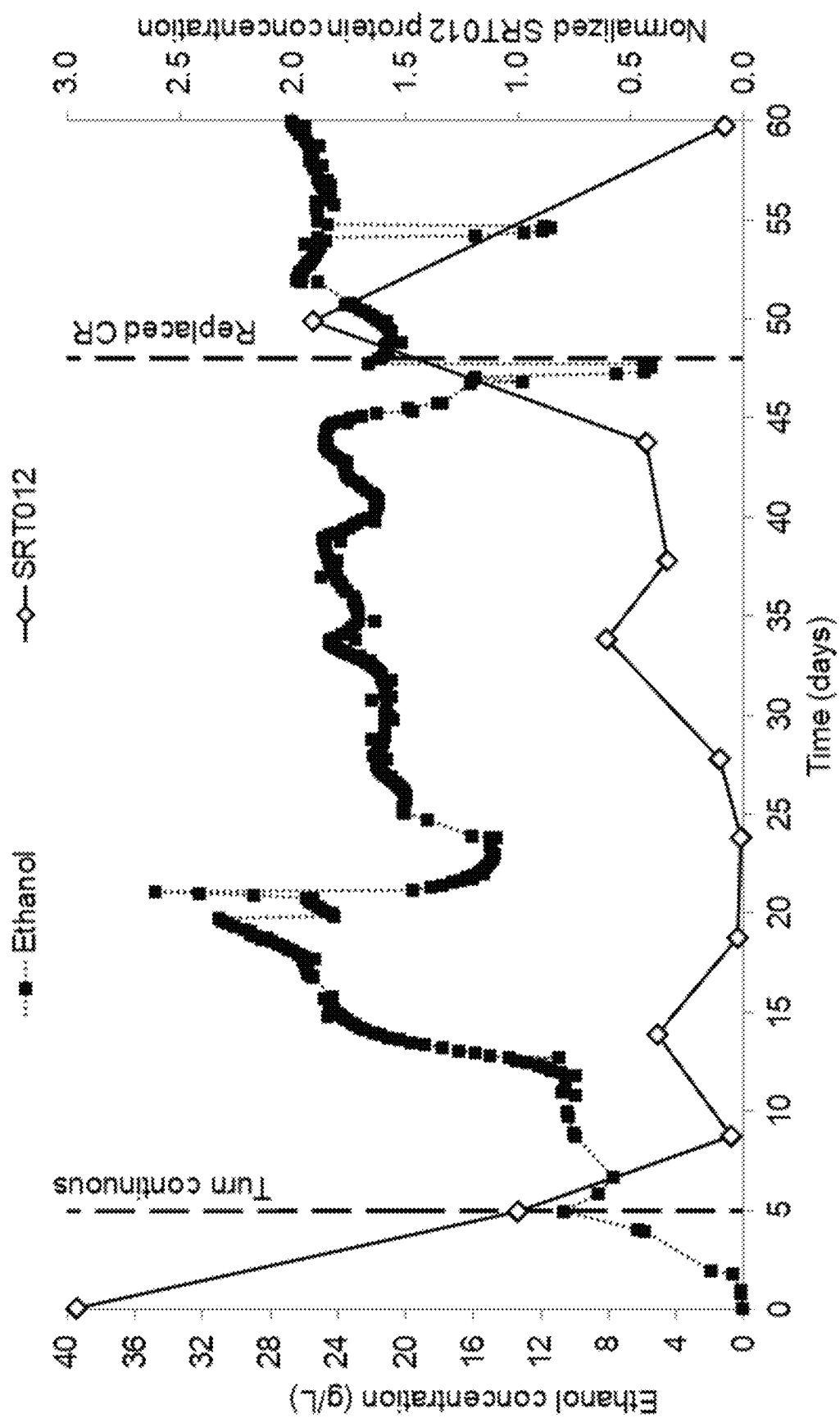
FIGS. 2A-2C show the performance of strSRT012 in continuous CSTR fermentation with cell recycling (CR) using a synthetic gas blend (55% CO, 5% $H_2$, 30% $CO_2$ and 10% $N_2$).
Figure 2B:
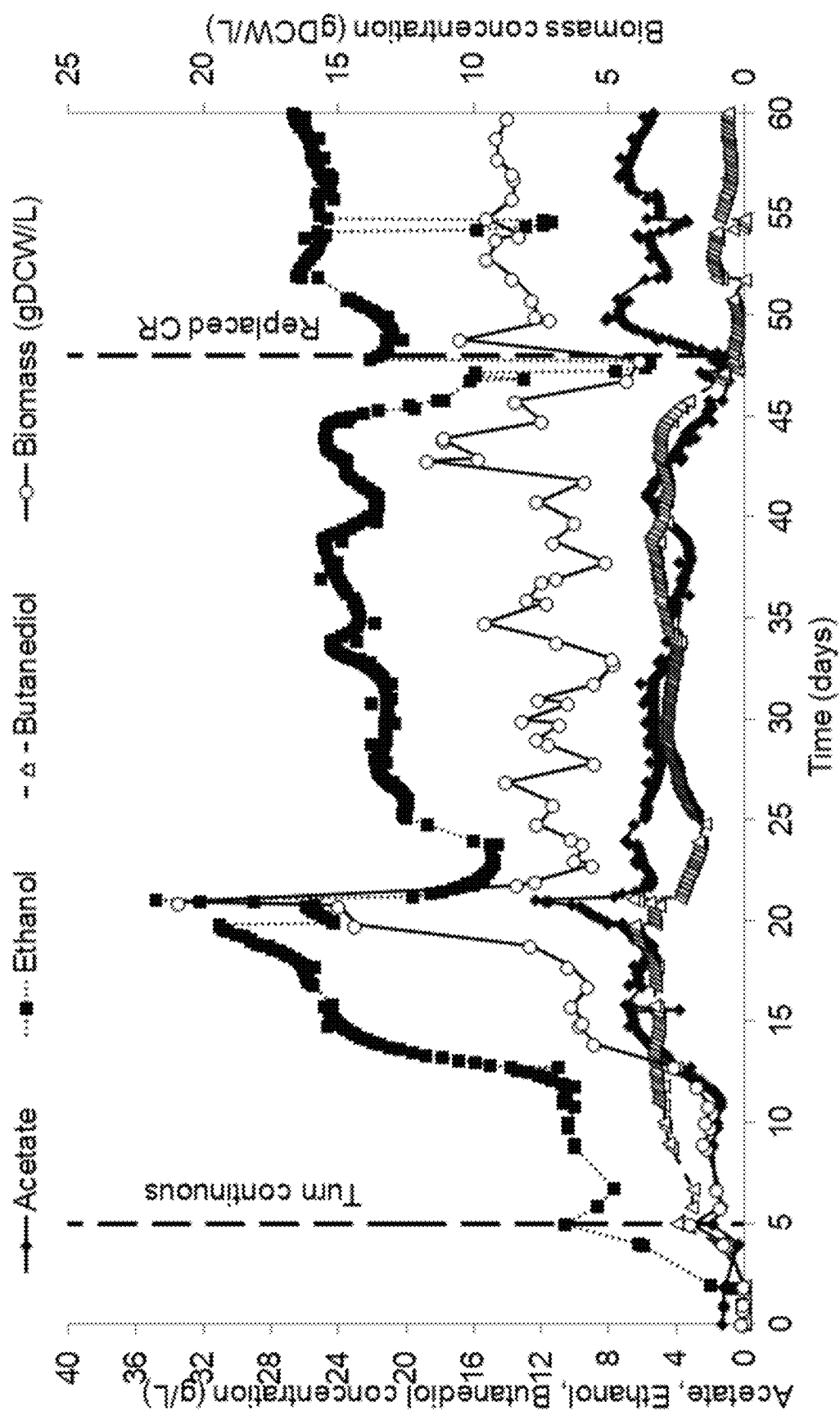
Figure 2C:
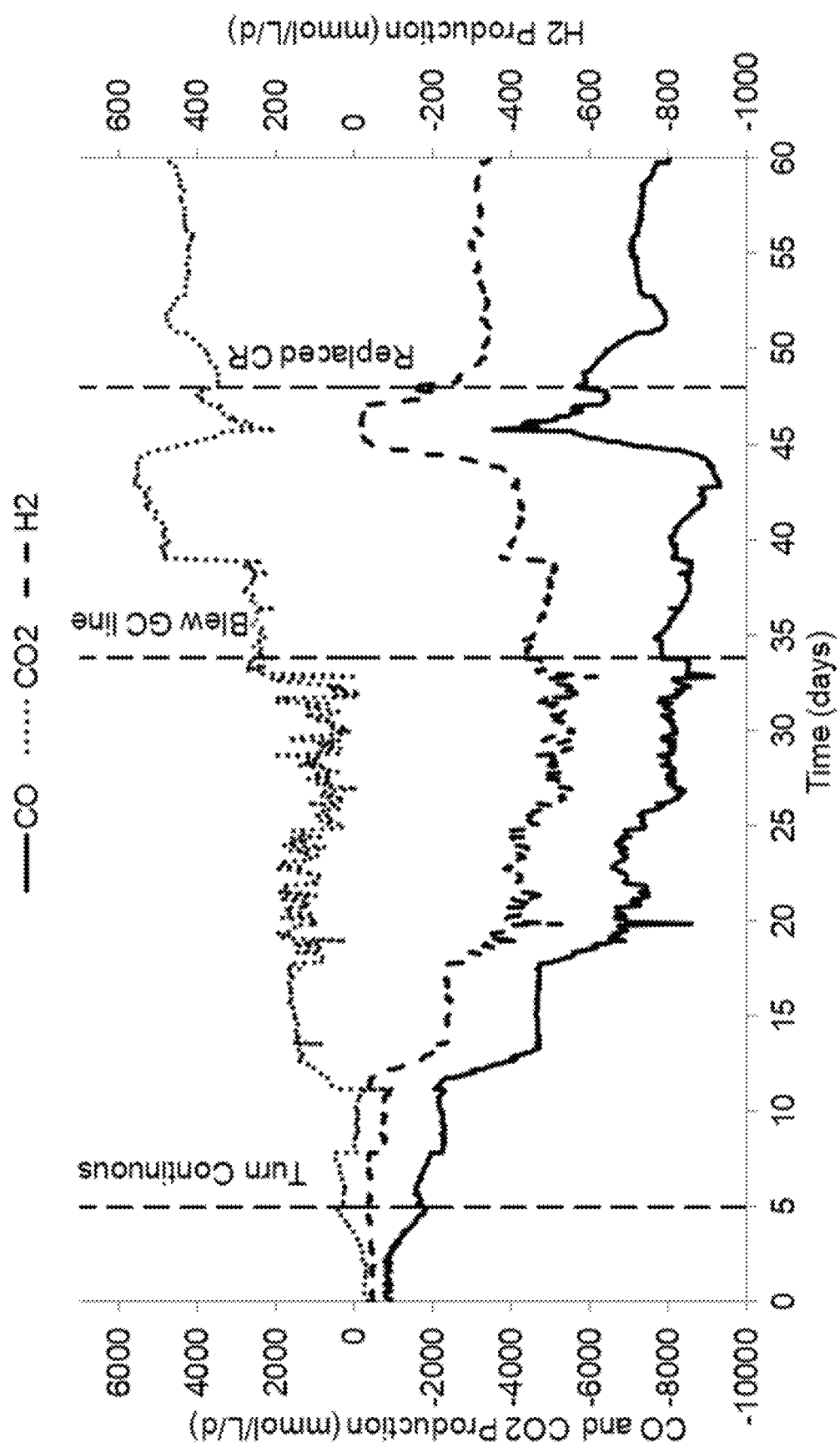

SRT008 protein was observed in all samples analyzed (FIG. 2A). Production of SRT008 was evaluated by Western blot analysis using anti-Strep tag antibodies. Samples were taken from the CSTR and frozen back for later analysis. After thawing samples, cells were lysed and the insoluble pellet was resuspended in 5 M urea. The samples were diluted with Laemmli sample buffer and run on tris-glycine SDS-PAGE protein gel. The samples were transferred to nitrocellulose membrane, stained with Ponceau S for total protein visualization and then probed with anti-Strep tag antibody conjugated to horseradish peroxidase for specific protein visualization. Specific protein content was measured and normalized to total protein content with densitometry analysis. Specific protein content normalized to total protein content is reported relative to day 5 (reactor turned continuous); highest relative protein content was at day 0 and another peak occurred between day 45 and day 55, around the same time a drop in ethanol production occurred and the cell recycle membrane was replaced.

Example 4: SRT008 and SRT012 Production from High Hydrogen Syngas Fermentation in Batch CSTR Tandem repeat protein-containing strains SRT008 and SRT012 (Table 2) were characterized in CSTR under batch mode to characterize protein production and chemical production. Actively growing (early exponential) culture from Schott bottles was used as inoculum for 2 L CSTRs with a synthetic gas blend (55% CO, 5% $H_2$, 30% $CO_2$, and 10% $N_2$) at atmospheric pressure. The culture was grown in the reactor using a High Hydrogen gas blend (10% CO, 50% $H_2$, 30% CO2, and 10% $N_2$).

Figure 5A:
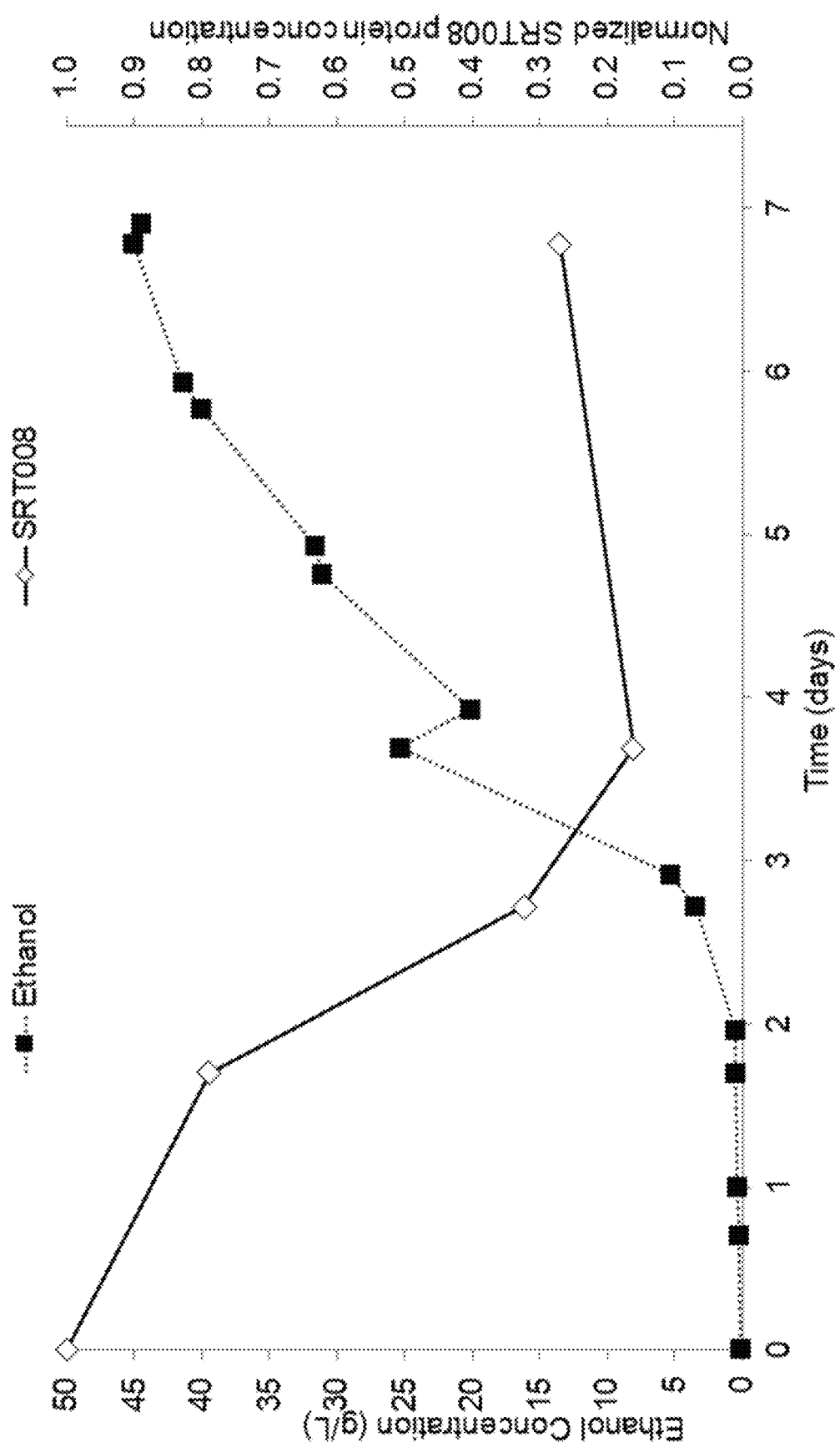
FIGS. 5A-5C show the performance of SRT008 in batch CSTR fermentation using a high hydrogen synthetic gas blend (10% CO, 50% $H_2$, 30% $CO_2$ and 10% $N_2$).
Figure 5B:
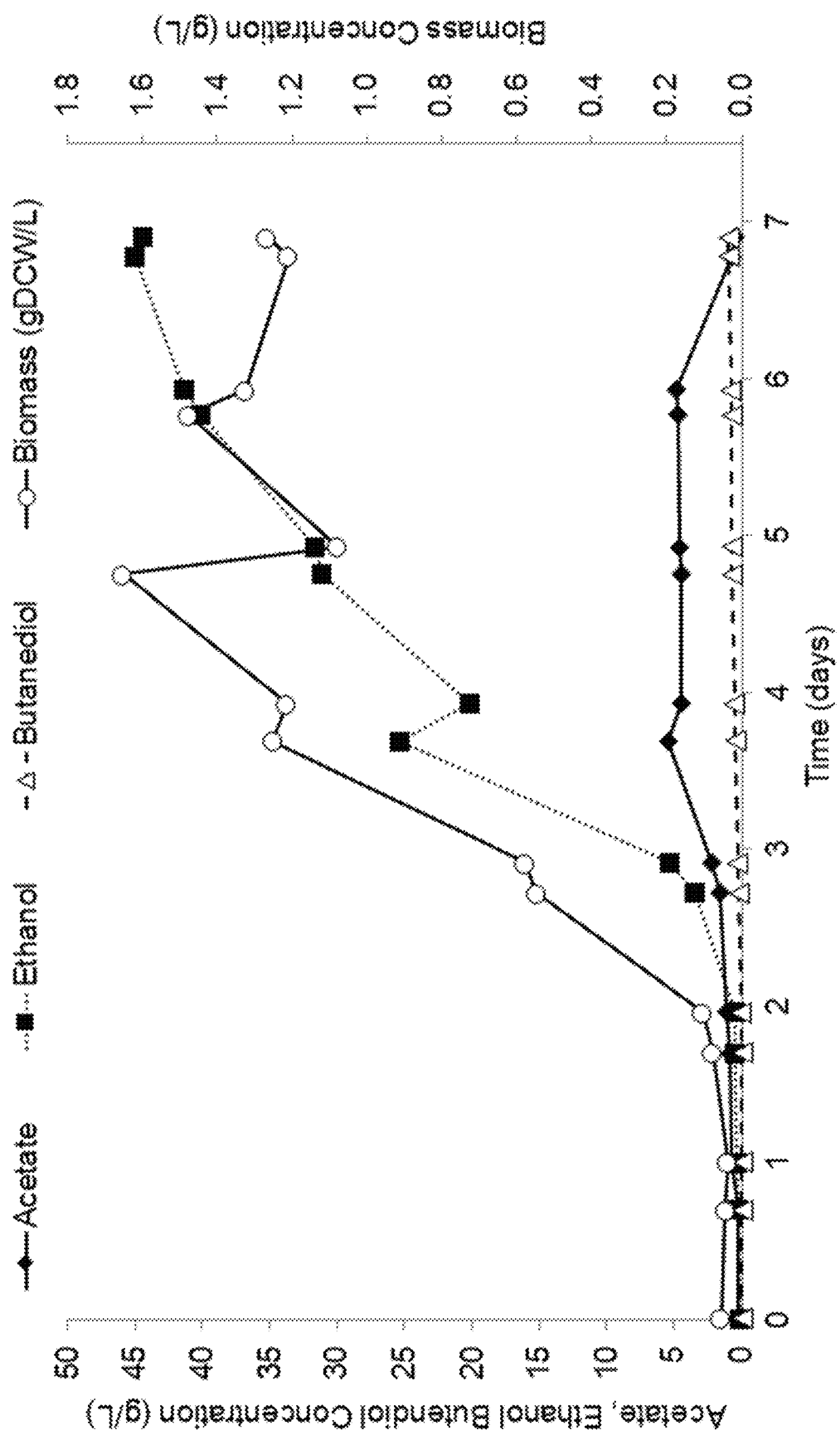
Figure 5C:
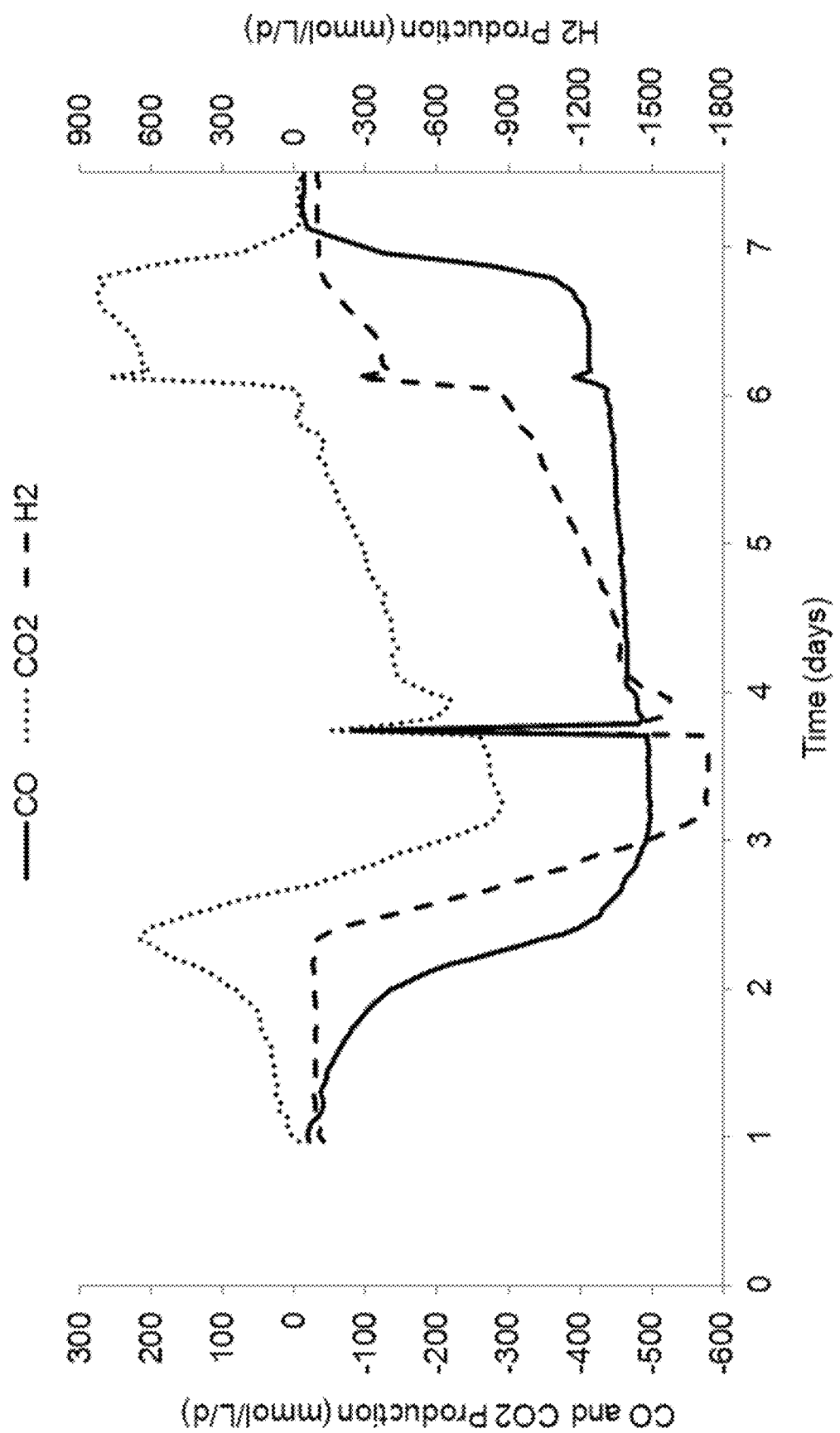

SRT008 achieved a peak biomass concentration of 1.32 gDCW/L (FIG. 5B) and reached a peak CO uptake of 590 mmol/L/d and a peak H2 uptake of 2060 mmol/L/d (FIG. 5C). In addition to a peak ethanol concentration of 45.06 g/L (FIG. 5B), this strain reached a peak acetate titer of 5.47 g/L (FIG. 5B). As indicated on all the figures, there was an upset just before day 4 with the agitator was left off for about 45 mins; the culture was affected but recovered soon after. SRT008 production was observed via Western blot on days 0, 1.7, 2.7, 3.7, and 6.8 with peak protein content at day 0 (FIG. 5A).

Figure 6A:
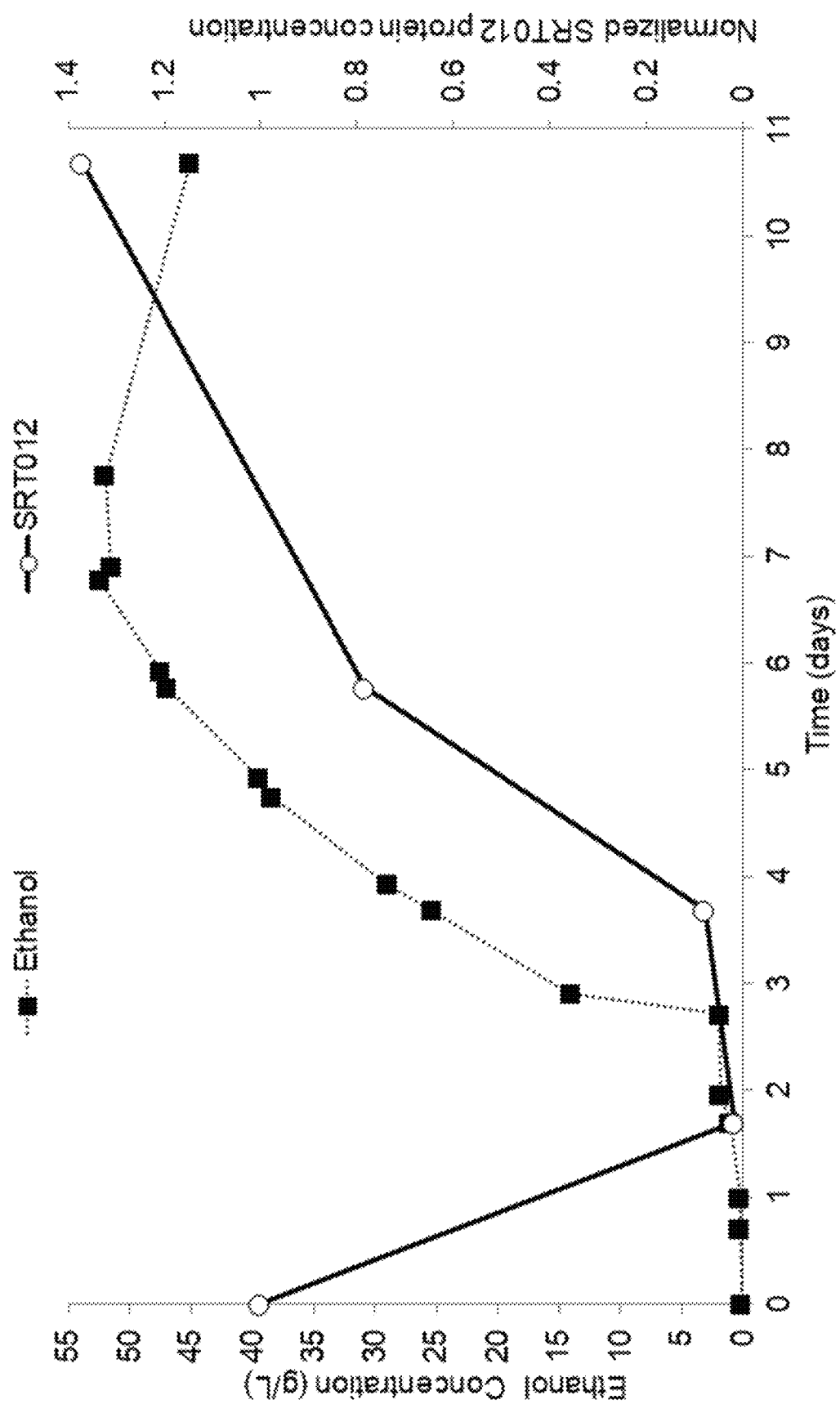
FIGS. 6A-6C show the performance of SRT012 in batch CSTR fermentation using a high hydrogen synthetic gas blend (10% CO, 50% $H_2$, 30% $CO_2$ and 10% $N_2$).
Figure 6B:
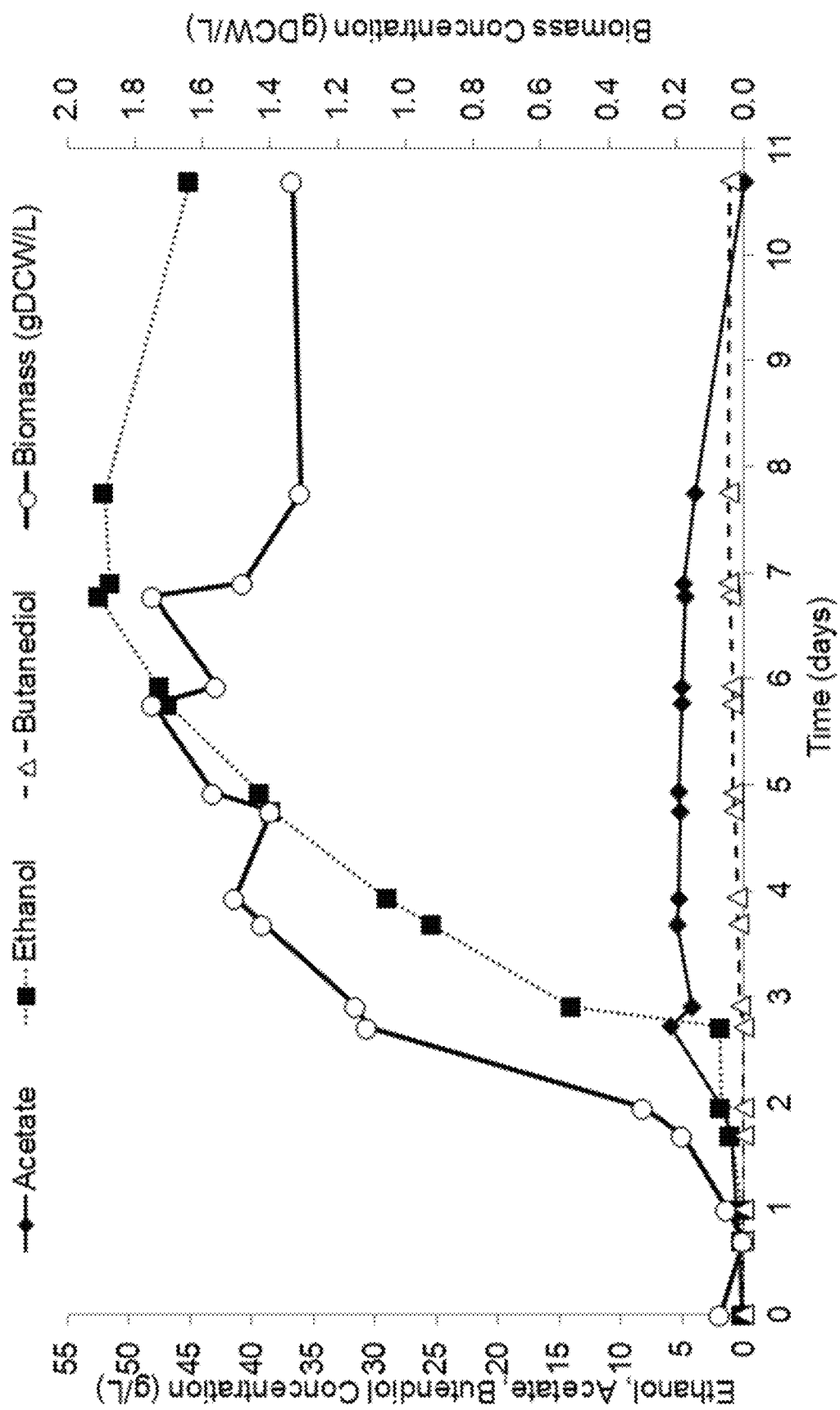
Figure 6C:
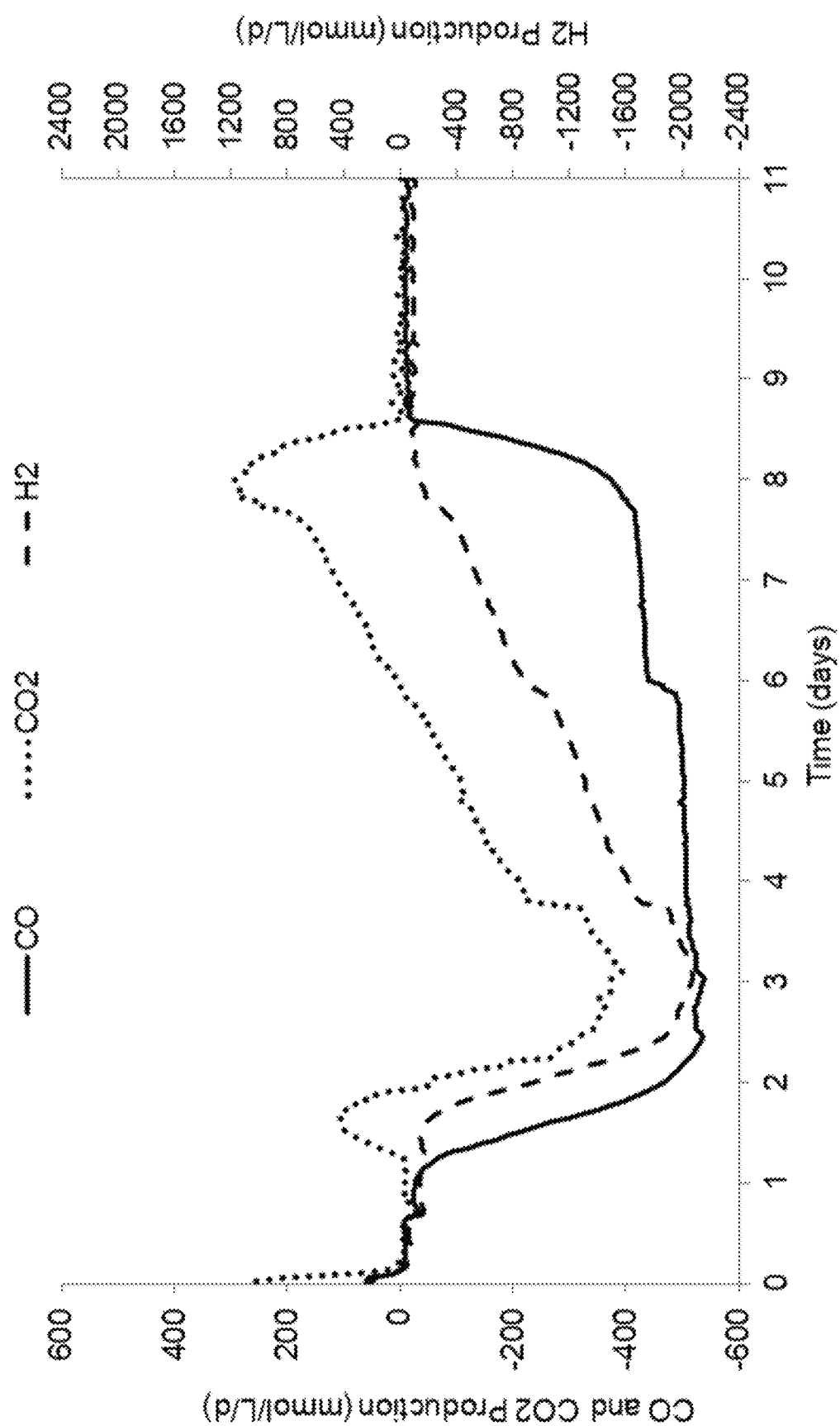

SRT012 achieved a peak biomass concentration of 1.75 gDCW/L (FIG. 6B) and reached a peak CO uptake of 535 mmol/L/d and a max H2 uptake of 2074 mmol/L/d (FIG. 6C). In addition to a peak ethanol concentration of 52.46 g/L (FIG. 6B), this strain reached a peak acetate titer of 5.47 g/L (FIG. 6B). SRT012 production was observed via Western blot on days 0, 1.7, 3.7, 5.8, and 10.7 with peak protein content measured at day 10.7 (FIG. 6A).

Example 5: Continuous Ethylene Production from $CO_2$ with $H_2$ as the Energy Source The gene coding for ethylene forming enzyme was codon-adapted and synthesized for expression in *Cupriavidus necator*. The adapted gene along with constitutive promoter P10 were cloned into the broad host range expression vector pBBR1MCS2. The resulting products were used to transform *E. coli* and positive clones identified by PCR were confirmed by DNA sequencing. The sequence confirmed plasmid was then transformed into *Cupriavidus necator* PHB-4 via electroporation and selected on tryptic soy broth (TSB) agar plates containing 50 mg/L chloramphenicol. Transformants containing the pBBR1-Efe plasmid were confirmed via sequencing and a single colony then grown overnight in TSB at 30° C. and used to make glycerol stocks for storage at −80° C. Strain revival was conducted via streaking onto a TSB plate containing 50 mg/L chloramphenicol with incubation at 30° C. for 72 hrs.

A single colony from a freshly streaked TSB plate was used to inoculate 3 mL TSB containing 50 mg/L chloramphenicol in a 14 mL Falcon round bottom polystyrene test tube with snap cap. Following overnight incubation at 30° C. and 200 rpm in a Thermo MAXQ shaker, 1 mL of culture was used to inoculate 100 mL LB in a 200 mL Schott bottle. Cells were grown at 30° C. and 200 rpm until an optical density of ~0.3-0.4 was reached.

100 mL of the above culture was used to inoculate a 1.4-L Infors HT Multifors 2 CSTR containing 600 mL of 2× startup media. The reactor was incubated at 30° C. and initiated with 250 rpm agitation and 150 nccm gas flow (3.14% $O_2$, 41% $H_2$, 3% $CO_2$, 52.86% $N_2$). Agitation and gas flow were ramped up to 1450 rpm and 750 nccm as the culture grew. When $OD_{600}$ exceeded 0.5, the culture was turned continuous using 4× media with 7 µL/hr Pluronic 31R1 antifoam. The feed oxygen percentage was gradually increased to promote biomass production, with the balance taken off nitrogen percentage, subject to the constraint that the outlet oxygen percentage remain below 4.5% as a safety measure.

Gas samples from the reactor were plumbed via 305 stainless steel to a stream selection valve controlled by a microGC (manufacturer: Qmicro). Samples were then analyzed on a Rt-U BOND XP PLOT column under isothermal conditions (70° C.) via a thermal conductivity detector (TCD).

Figure 7:
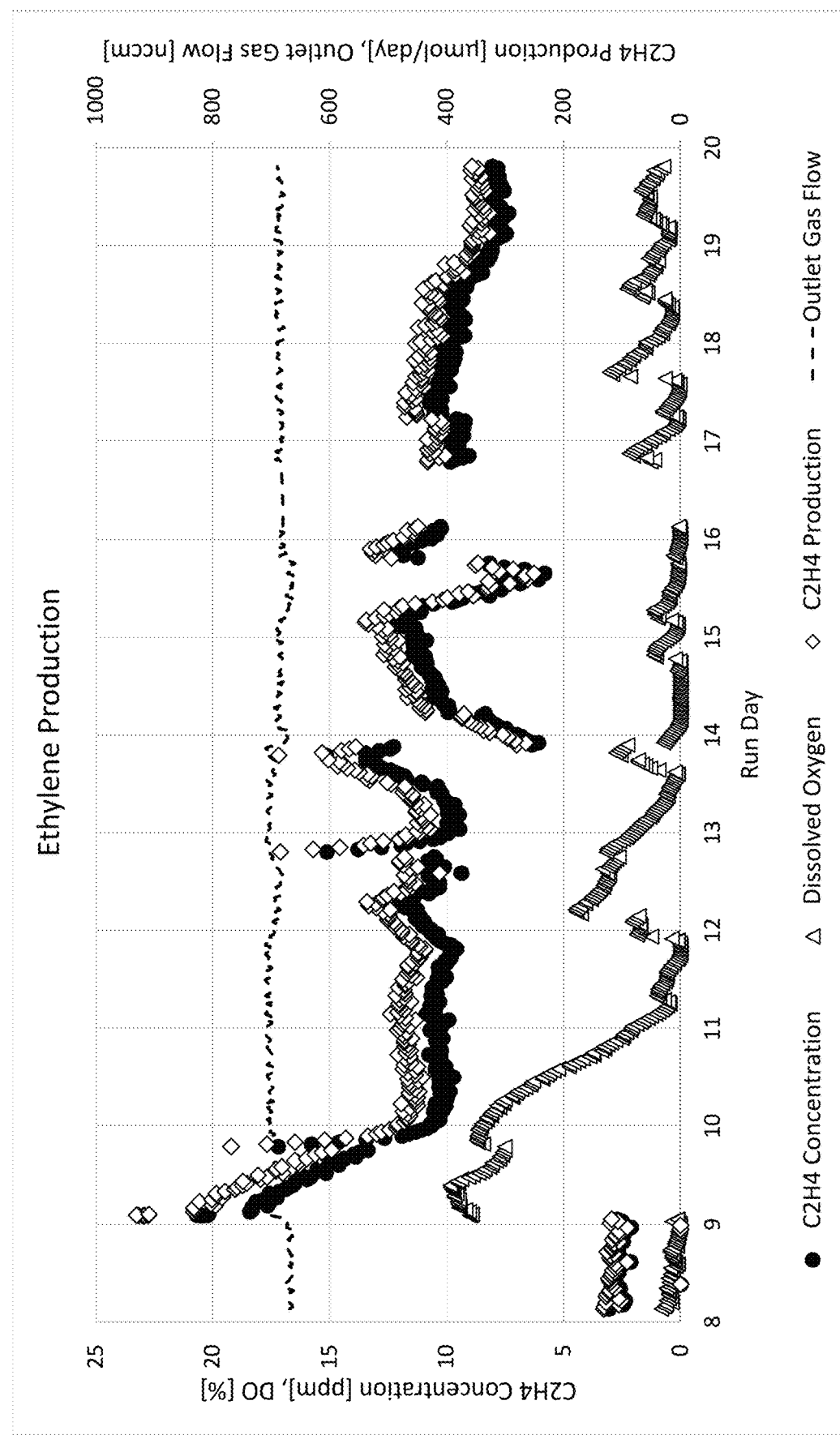
FIG. 7 shows continuous ethylene production from $CO_2$ as the sole carbon source in a CSTR over an 11-day period by a *Cupriavidus necator* strain with ethylene forming enzyme expression (pBBR1-Efe).

Once the culture was well-established, gas fractions were adjusted from $O_2$-limiting to $H_2$-limiting conditions such that a non-zero dissolved oxygen (DO) concentration was observed. Ethylene production varied as the system settled into steady-state and as gas fractions were adjusted, but production was maintained for over 11 days (FIG. 7). During this period, $H_2$ fraction ranged from 11-18% and $O_2$ fraction from 5.5-6.6%, with $CO_2$ held at 3% and $N_2$ as the balance. Upon switching back to $O_2$-limiting conditions, ethylene production ceased indicating the importance of oxygen availability for ethylene production.

Example 6: A System for Generating Bubbles within a Vessel

Figure 8:
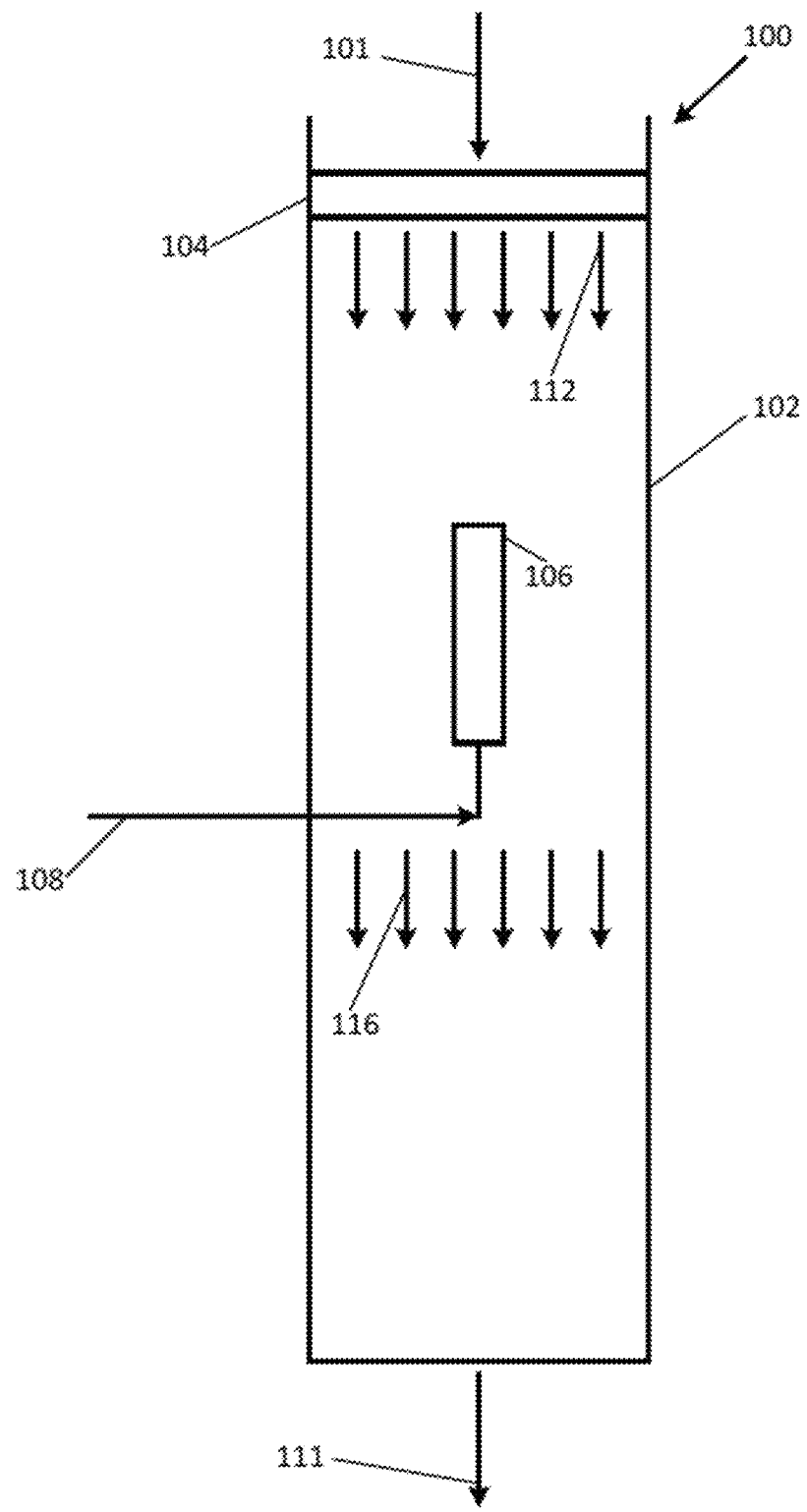
FIG. 8 schematically depicts a system for generating bubbles within a vessel, according to the systems and methods disclosed herein.

An example of a system of generating bubbles in a vessel 100 (FIG. 8). System 100 comprises cylindrical reactor 102. Liquid enters inlet or top portion 101 of reactor 102. The liquid may enter top portion 101 via an external pump in fluid communication with system 100. According to certain embodiments, the liquid entering top portion 101 is recirculated by an external pump in fluid communication with system 100. The liquid enters the top of perforated plate 104 and the liquid is accelerated by passing though the orifices in plate 104. According to certain examples, plate 104 may be configured to accelerate, for example, at least, greater than, less than, equal to, or any number from about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99 to about 100% of the liquid in reactor 102. Sparger 106 injects gas bubbles into the liquid from gas source 108. Sparger 106 is positioned within reactor 102 such that a first zone is created in which the injected bubbles rise within reactor 102 and encounter accelerated liquid 112 exiting the bottom of plate 104. Accelerated liquid 112 from plate 104 breaks the rising bubbles into fine bubbles thereby increasing the superficial surface area required for the desired chemical or biological reaction. The fine bubbles may have a diameter in the range of about 0.1 mm to about 5 mm, or from about 0.5 mm to about 2 mm. In some examples, the fine bubbles may include a diameter from about 0.2 mm to 1.5 mm. According to another embodiment, the diameter of the fine bubbles may be, for example, at least, greater than, less than, equal to, or any number in between about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to about 5.0 mm. Sparger 106 is further positioned within reactor 102 such that a second zone is created in which the fluid flow of liquid and fine bubbles may flow downward.

The fine bubbles may have a decreased rise velocity compared to the injected bubbles. Due to the overall flow of the accelerated liquid, fluid 116, containing the liquid and the fine bubbles, may have a net downward flow. The downward velocity of fluid 116 is greater than the overall rise velocity of the fine bubbles. Fluid 116 may exit reactor 102 at outlet 111. Plate 104 may have a thickness (and a depth of the orifices) from about 1 mm to 25 mm. According to another embodiment, the thickness of the plate may be, for example, at least, greater than, less than, equal to, or any number in between about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 mm.

The dimensions of the components of system 100, as illustrated in (FIG. 8), may vary depending upon the required use or process. According to certain embodiments, the diameter of the reactor 102 may be, for example, at least, greater than, less than, equal to, or any number in between about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5 to about 20.0 meters. According to other embodiments, the length of the reactor 102 may be, for example, at least, greater than, less than, equal to, or any number in between about 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.5, 21.5, 22.0, 22.5, 23.0, 23.5, 24.0, 24.5, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0 to about 50.0 meters.

The velocity of the liquid or a portion of the liquid accelerated from plate 104 can be determined by the following equation:

$$QL = N \times (\pi/4) \times d2 \times vj$$

where QL is the liquid volumetric flow rate (m3/s), vj is the jet velocity, N is the total number of orifices on the plate, d is the diameter of the orifices, and π is the mathematical symbol pi. According to one embodiment, the velocity of the accelerated liquid from plate 104 may be, for example, at least, greater than, less than, equal to, or any number in between about 5000, 5500, 6000, 6500, 7000, 7500, 8000, 8500, 9000, 9500, 10000, 10500, 11000, 11500, 12000, 12500, 13000, 13500, 14000, 14500, 15000, 15500, 16000, 16500, 17000, 17500, 18000, 18500, 19000, 19500 to about 20000 mm/s. As depicted in FIG. 8, the velocity of accelerated liquid 112 is critical to breaking bubbles injected into the liquid by sparger 106 into properly sized fine bubbles, and to ensuring that the fluid of liquid and fine bubbles has enough velocity to generate a net downward fluid flow. The superficial liquid velocity, VL, in the main reaction vessel may be calculated by the following equation: VL-QL/AC where QL is the volumetric flow rate of the liquid (m3/s) in the reaction vessel and AC is the cross-sectional area of the reaction vessel. Therefore, superficial liquid velocity represents velocity of the liquid phase if it occupied the entire cross-sectional area of the reaction vessel. According to embodiments, the superficial liquid velocity may also include zones or voids of stagnant liquid and fine bubbles, and/or net downward fluid flow. For the same liquid flow rate, the gas flow rate can vary depending on the actual application. Superficial velocity of the gas phase VG may be determined by the following equation: VG=QG/AC where QG is the volumetric flow rate of the gas (m3/s) injected into the liquid from the sparger(s) and AC is the cross-sectional area of the reaction vessel. According to another embodiment, the superficial velocity of the gas phase in the vessel may be, for example, at least, greater than, less than, equal to, or any number in between about 5, 10, 15, 20, 25, 30, 35, 40, 45, 50, 55, 60, 65, 70, 75, 80, 85, 90, 95 to about 100 mm/s. According to still another embodiment, the superficial velocity of the gas phase in the vessel may be, for example, approximately 50-60 mm/s.

Positioning of a sparger or multiple spargers 106 within reactor 102, and in an upper portion of reactor 102 has the additional advantage of decreasing hydrostatic pressure at the top of reactor 102 facilitating increased gas to liquid mass transfer rates with decreased energy requirements. Further, required reactor components are minimized, yet gas to liquid mass transfer rates are maximized with a smaller reactor footprint due to decreased reactor size. In some embodiments, for example, the systems and methods disclosed herein achieve gas to liquid mass transfer rates of at least 125 m$^3$/min. In other examples, the gas to liquid mass transfer rates may be, for example, at least, greater than, less than, equal to, or any number in between about 100, 105, 110, 115, 120, 125, 130, 135, 140, 145, 150, 155, 160, 165, 170, 175, 180, 185, 190, 195 to about 200 m$^3$/min. Additionally, the sparger configurations, superficial velocities of the gas and liquid phases achieved, and the increased gas to liquid mass transfer rates disclosed herein overcome known obstacles associated with the use of a gas and liquid phase system of the previous and conventional reactors. Particularly in bioreactors having a gas substrate and an aqueous culture.

Example 7: Production of Superoxide Dismutases in Autotroph *Clostridium autoethanogenum*

TABLE 3

Superoxide dismutase proteins expressed in *C. autoethanogenum*.

| SEQ ID NO: | Protein name | Protein Source | UniProt ID | Amino acid sequence (size) |
|---|---|---|---|---|
| SEQ ID No: 5 | SOD006 | *Rhodobacter capsulatus* SB 1003 | D5AL51 | MAFELPALPYAHDALAALGMSKETLEYHHDLHHKAYVDNG NKLIAGTEWEGKSVEEIVKGTYCAGAVAQSGIFNNASQHW NHAQFWEMMGPGEDKKMPGELEKALVEAFGSVAKFKEDF AAAGAAQFGSGWAWLVKDTDGALKITKTENGVNPLCFGQ TALLGCDVWEHSYYIDFRNKRPVYLTNFLDKLVNWENVASR L |
| SEQ ID No: 6 | SOD007 | *Cupriavidus necator* H16 | Q0KE13 | MEHKLPPLPYAHDALAPHISKETLEFHHDKHHQTYVTNLNN LIKGTEFENSTLEEIVKKSSGGIFNNAAQVWNHTFYWDSMK PNGGGQPTGALADAINAKWGSFDKFKEEFTKTAVGTFGSG WAWLVKKADGSLDLVSTSNAATPLTTDAKALLTCDVWEHA YYIDYRNARPKYVEAFWNVVNWDFAGKNFAG |
| SEQ ID No: 7 | SOD009 | *Klebsiella pneumoniae* KCTC 2242 | A0A0H3GYY6 | MSFELPALPYAKDALAPHISAETLEYHYGKHHQAYVTNLNNL IKGTAFEGKSLEEIVRTSEGGVFNNAAQVWNHTFYWNCLAP NAGGEPEGELAAAIAKSFGSFADFKAKFTDAAAKNFGAGWT WLVKNADGSLAIVSTSNAGTPLTTDAKPLLTVDVWEHAYYI DYRNARPSYLDHFWALVNWKFVAANLAA |
| SEQ ID No: 8 | SODD010 | *Klebsiella pneumoniae* KCTC 2242 | A0A0H3GLE8 | MSYTLPSLPYAYDALEPHFDKQTMEIHHTKHHQTYVNNAN AALESLPEFANLSAEELITKLDQLPADKKTVLRNNAGGHANH SLFWKGLKTGTTLQGDLKAAIERDFGSVENFKAEFEKAAATR FGSGWAWLVLKGDKLAVVSTANQDSPLMGEAISGASGFPII GLDVWEHAYYLKFQNRRPDYIKAFWDVVNWDEAAARFAA KK |

Genes encoding superoxide dismutases were codon adapted for *C. autoethanogenum*, synthesized by vendors, and assembled into *Clostridium-E. coli* shuttle vector pMTL8225 (Heap, J Microbiol Methods 78: 79-85, 2009). These vectors have a pre-cloned ermB antibiotic selectable marker and a clostridial promoter and terminator. The P$_{fer}$ promoter sequence was used and is described in Karim et al. Synthetic Biology 2020; 5(1): ysaa019. After transformation into *Clostridium*, the sequence-verified strains were subjected to autotrophic growth in 24-well plates.

Protein expression experiments were started in 24-well plates with 1 mL minimal media with supplemented yeast extract and antibiotic, fed 200 kPa of synthetic gas mix (55% CO, 5% $H_2$, 30% $CO_2$, and 10% $N_2$), and grown at 37° C. until a biomass of 0.1-0.3 gDCW/L was reached. The strains were then subcultured by adding 50 uL of culture to 1 mL minimal medium supplemented with yeast extract and antibiotic in 24-well plates in the presence of 200 kPa synthetic gas mix (55% CO, 5% $H_2$, 30% $CO_2$, and 10% $N_2$) at 37° C. Biomass concentration was monitored until it reached 0.12-0.26 gDCW/L and then the biomass was harvested and washed in PBS.

Figure 9:
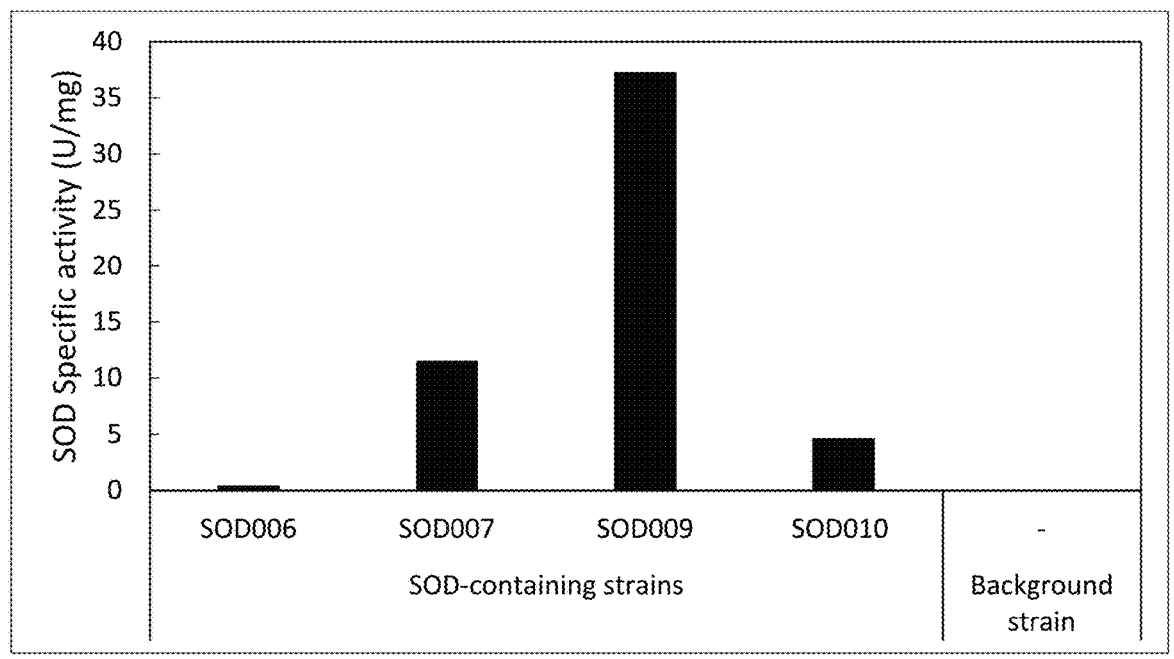
FIG. 9 shows heterologous superoxide dismutases actively expressed in *C. autoethanogenum*. SOD activity was measured in clarified lysates and normalized to total protein concentration.

The harvested biomass was lysed and clarified and the clarified lysate was assayed for superoxide dismutase activity using a kit from Invitrogen (catalog #EIASODC). The kit's standards report SOD activity in units/mL. One unit of SOD activity is defined as the amount of enzyme causing half the maximum inhibition of the reduction of 1.5 mM nitro blue tetrazolium in the presence of riboflavin at 25° C. and pH 7.8. In order to report SOD specific activity (FIG. 9), or SOD activity normalized to total protein, the clarified lysate was also assayed for total protein quantity with the Pierce™ BCA Protein Assay.

Figure 10:
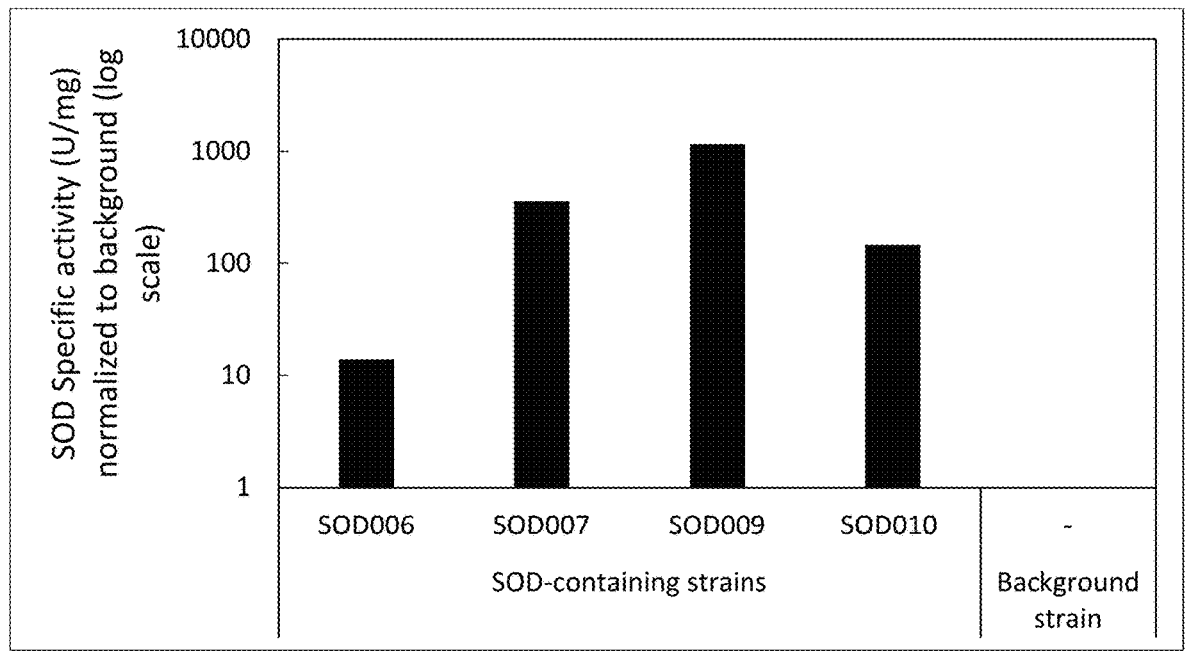
FIG. 10 shows heterologous superoxide dismutases active above background in *C. autoethanogenum*. SOD specific activity was measured in clarified lysates and normalized to a background strain. The y-axis is log scale.

Specific activity above background (*C. autoethanogenum* carrying same plasmid but not expressing a superoxide dismutase) was observed for strains expressing SOD006 (0.4 U/mg, 13× above background), SOD007 (12 U/mg, 360× above background), SOD009 (37 U/mg, 1160× above background), SOD010 (4.7 U/mg, 140× above background) (FIG. 10).

Superoxide dismutase enzymes (E.C. 1.15.1.1) are widespread in nature, found in all living cells. Sequences can be retrieved from public databases such as NCBI, KEGG, Uniprot, etc. NCBI lists over 10,000 superoxide dismutase sequences and over 2,000 microbial superoxide dismutase sequences. A range of exemplary microbial superoxide dismutases from which sequences have been selected are provided below. All reference sequences for the representative superoxide dismutase proteins in the table above and cited herein from the databases are incorporated by reference to the same extent as if each reference were individually and specifically indicated to be incorporated by reference and were set forth in its entirety herein.

Superoxide dismutases with reported structural data: For over 50 microbial superoxide dismutases, a structure is available. These can be retrieved from Uniprot, PDB or similar databases: examples pulled from UniProt provided below. Retrieved sequences have been reviewed and any sequences that were chaperones or associated with superoxide dismutases but were not annotated as having superoxide dismutase activity were removed.

TABLE 4

Exemplary superoxide dismutase proteins.

| UniProt Entry ID | Protein names | Organism |
| --- | --- | --- |
| P00448 | Superoxide dismutase [Mn] (EC 1.15.1.1) (MnSOD) | *Escherichia coli* (strain K12) |
| P0AGD1 | Superoxide dismutase [Cu—Zn] (EC 1.15.1.1) (Bacteriocuprein) | *Escherichia coli* (strain K12) |
| P0AGD3 | Superoxide dismutase [Fe] (EC 1.15.1.1) | *Escherichia coli* (strain K12) |
| P0CW86 | Superoxide dismutase [Cu—Zn] (EC 1.15.1.1) (sodCI) | *Salmonella typhimurium* (strain LT2/SGSC1412/ATCC 700720) |
| P54375 | Superoxide dismutase [Mn] (EC 1.15.1.1) (General stress protein 24) (GSP24) | *Bacillus subtilis* (strain 168) |
| P9WGE7 | Superoxide dismutase [Fe] (EC 1.15.1.1) | *Mycobacterium tuberculosis* (strain ATCC 25618/H37Rv) |
| P9WGE9 | Superoxide dismutase [Cu—Zn] (EC 1.15.1.1) | *Mycobacterium tuberculosis* (strain ATCC 25618/H37Rv) |
| E8XDJ8 | Superoxide dismutase [Cu—Zn] 1 (EC 1.15.1.1) (sodCI) | *Salmonella typhimurium* (strain 4/74) |
| O31851 | Superoxide dismutase-like protein YojM | *Bacillus subtilis* (strain 168) |
| P00446 | Superoxide dismutase [Cu—Zn] (EC 1.15.1.1) | *Photobacterium leiognathi* |
| P00449 | Superoxide dismutase [Mn] (EC 1.15.1.1) | *Geobacillus stearothermophilus* (*Bacillus stearothermophilus*) |
| P09223 | Superoxide dismutase [Fe] (EC 1.15.1.1) | *Pseudomonas putida* (*Arthrobacter siderocapsulatus*) |
| P15453 | Superoxide dismutase [Cu—Zn] (EC 1.15.1.1) | *Brucella abortus* biovar 1 (strain 9-941) |
| P19665 | Superoxide dismutase [Mn/Fe] (EC 1.15.1.1) | *Porphyromonas gingivalis* (strain ATCC BAA-308/W83) |
| P24702 | Superoxide dismutase [Cu—Zn] (EC 1.15.1.1) | *Actinobacillus pleuropneumoniae* (*Haemophilus pleuropneumoniae*) |
| P61503 | Superoxide dismutase [Mn] (EC 1.15.1.1) | *Thermus thermophilus* (strain ATCC 27634/DSM 579/HB8) |
| P80734 | Superoxide dismutase [Ni] (EC 1.15.1.1) (NiSOD) (Nickel-containing superoxide dismutase) | *Streptomyces seoulensis* |
| P80735 | Superoxide dismutase [Ni] (EC 1.15.1.1) (NiSOD) (Nickel-containing superoxide dismutase) | *Streptomyces coelicolor* (strain ATCC BAA-471/A3(2)/M145) |
| Q7SIC3 | Superoxide dismutase [Mn] (EC 1.15.1.1) | *Virgibacillus halodenitrificans* (*Bacillus halodenitrificans*) |

TABLE 4-continued

Exemplary superoxide dismutase proteins.

| UniProt Entry ID | Protein names | Organism |
|---|---|---|
| Q9X6W9 | Superoxide dismutase [Fe] (Fe-SOD) (EC 1.15.1.1) | *Aquifex pyrophilus* |
| O30970 | Superoxide dismutase [Fe] (EC 1.15.1.1) | *Rhodobacter capsulatus* (*Rhodopseudomonas capsulata*) |
| P09738 | Superoxide dismutase [Mn/Fe] (EC 1.15.1.1) | *Streptococcus mutans* serotype c (strain ATCC 700610/UA159) |
| P0A0J3 | Superoxide dismutase [Mn] 1 (EC 1.15.1.1) | *Staphylococcus aureus* (strain NCTC 8325/PS 47) |
| P19685 | Superoxide dismutase [Fe] (EC 1.15.1.1) | *Coxiella burnetii* (strain RSA 493 / Nine Mile phase I) |
| P43312 | Superoxide dismutase [Fe] (EC 1.15.1.1) | *Helicobacter pylori* (strain ATCC 700392/26695) (*Campylobacter pylori*) |
| P57005 | Superoxide dismutase [Cu—Zn] (EC 1.15.1.1) | *Neisseria meningitidis* serogroup A / serotype 4A (strain DSM 15465 / Z2491) |
| P80293 | Superoxide dismutase [Mn/Fe] (EC 1.15.1.1) | *Propionibacterium freudenreichii* subsp. *shermanii* |
| P84612 | Superoxide dismutase [Fe] (EC 1.15.1.1) | *Pseudoalteromonas translucida* (strain TAC 125) |
| Q2G261 | Superoxide dismutase [Mn/Fe] 2 (EC 1.15.1.1) | *Staphylococcus aureus* (strain NCTC 8325/PS 47) |
| Q59452 | Superoxide dismutase [Cu—Zn] (EC 1.15.1.1) | *Haemophilus ducreyi* (strain 35000HP/ATCC 700724) |
| Q59623 | Superoxide dismutase [Cu—Zn] (EC 1.15.1.1) | *Neisseria meningitidis* serogroup B (strain MC58) |
| Q81JK8 | Superoxide dismutase [Mn] 2 (EC 1.15.1.1) | *Bacillus anthracis* |
| Q81LW0 | Superoxide dismutase [Mn] 1 (EC 1.15.1.1) | *Bacillus anthracis* |
| Q9RUV2 | Superoxide dismutase [Mn] (EC 1.15.1.1) (MnSOD) | *Deinococcus radiodurans* (strain ATCC 13939/DSM 20539/JCM 16871/LMG 4051/NBRC 15346 / NCIMB 9279/R1/VKM B-1422) |
| A0A031LR83 | Superoxide dismutase (EC 1.15.1.1) | Acinetobacter sp. Ver3 |
| A0A0M3KL50 | Superoxide dismutase (EC 1.15.1.1) | *Sphingobacterium spiritivorum* (*Flavobacterium spiritivorum*) |
| A0A1E5TT85 | Superoxide dismutase (EC 1.15.1.1) | *Staphylococcus equorum* |
| A0A1F3DVA5 | Superoxide dismutase [Cu—Zn] (EC 1.15.1.1) | *Bacteroidetes bacterium* GWA2_30_7 |
| A0QQQ1 | Superoxide dismutase [Cu—Zn] (EC 1.15.1.1) | *Mycolicibacterium smegmatis* (strain ATCC 700084/mc(2)155) (*Mycobacterium smegmatis*) |
| B6ENP9 | Superoxide dismutase (EC 1.15.1.1) | *Aliivibrio salmonicida* (strain LFI1238) (*Vibrio salmonicida* (strain LFI1238)) |
| Q18616 | Superoxide dismutase (EC 1.15.1.1) | *Clostridioides difficile* (strain 630) (*Peptoclostridium difficile*) |
| Q2GKX4 | Superoxide dismutase (EC 1.15.1.1) | *Anaplasma phagocytophilum* (strain HZ) |
| Q5M4Z1 | Superoxide dismutase (EC 1.15.1.1) | *Streptococcus thermophilus* (strain ATCC BAA-250/LMG 18311) |
| Q5NIJ9 | Superoxide dismutase (EC 1.15.1.1) | *Francisella tularensis* subsp. *tularensis* (strain SCHU S4/Schu 4) |
| Q66ED7 | Superoxide dismutase [Cu—Zn] (EC 1.15.1.1) | *Yersinia pseudotuberculosis* serotype I (strain IP32953) |
| Q704S6 | Superoxide dismutase [Cu—Zn] (EC 1.15.1.1) | *Salmonella enterica* subsp. *enterica* serovar *Choleraesuis* |
| Q8DIR2 | Superoxide dismutase (EC 1.15.1.1) | *Thermosynechococcus vestitus* (strain NIES-2133/IAM M-273/BP-1) |

TABLE 4-continued

Exemplary superoxide dismutase proteins.

| UniProt Entry ID | Protein names | Organism |
|---|---|---|
| Q8PJZ1 | Superoxide dismutase (EC 1.15.1.1) | *Xanthomonas axonopodis* pv. *citri* (strain 306) |
| Q8Z0M1 | superoxide dismutase (EC 1.15.1.1) | *Nostoc* sp. (strain PCC 7120/SAG 25.82/UTEX 2576) |

Superoxide dismutases from anaerobic microbes: There are several anaerobic superoxide dismutase sequences. A set of superoxide dismutase genes from anaerobic bacteria can be pulled from multiple sources. For Firmicutes as a representative anaerobic phylum of bacteria over 400 sequences are available, pulled from NCBI in the table below. In addition, several Klebsiella superoxide dismutases have been described in literature (https://www.sciencedirect.com/science/article/pii/S0891584918316770?via%3Dihub).

TABLE 5

Exemplary superoxide dismutase proteins.

| NCBI taxonomic ID | Organism name | NCBI GeneID | Symbol | description |
|---|---|---|---|---|
| 999409 | [*Clostridium*] *clostridioforme* 90B1 | 63965715 | HMPREF1086_RS08840 | superoxide dismutase family protein |
| 1522 | [*Clostridium*] *innocuum* | 61924601 | G4D54_RS03650 | superoxide dismutase |
| 29347 | [*Clostridium*] *scindens* | 69694651 | CSCING10_RS11970 | superoxide dismutase family protein |
| 1512 | [*Clostridium*] *symbiosum* | 57970340 | F2P57_RS17120 | superoxide dismutase family protein |
| 411470 | [*Ruminococcus*] *gnavus* ATCC 29149 | 57434366 | RGna_RS12090 | superoxide dismutase family protein |
| 572545 | *Acetivibrio thermocellus* DSM 2360 | 57418012 | LQRI_RS02860 | superoxide dismutase |
| 119206 | *Aerococcus sanguinicola* | 69592604 | 14163_RS02455 | superoxide dismutase |
| 1376 | *Aerococcus urinae* | 35767902 | AWM73_RS04480 | superoxide dismutase family protein |
| 51665 | *Aerococcus urinaeequi* | 77094530 | APT62_RS03675 | superoxide dismutase |
| 79880 | *Alkalihalobacillus clausii* | 61574535 | CHH52_RS16580 | superoxide dismutase |
| 79880 | *Alkalihalobacillus clausii* | 61572520 | CHH52_RS06270 | superoxide dismutase |
| 79880 | *Alkalihalobacillus clausii* | 61572634 | sodA | superoxide dismutase SodA |
| 79880 | *Alkalihalobacillus clausii* | 61571414 | CHH52_RS00655 | superoxide dismutase family protein |
| 105841 | *Anaerostipes caccae* | 69468268 | LCQ53_RS02075 | superoxide dismutase |
| 169435 | *Anaerotruncus colihominis* | 72462569 | K5I23_RS01140 | superoxide dismutase |
| 491915 | *Anoxybacillus flavithermus* WK1 | 7037288 | AFLV_RS05545 | superoxide dismutase |
| 491915 | *Anoxybacillus flavithermus* WK1 | 7037134 | sodA | superoxide dismutase SodA |
| 491915 | *Anoxybacillus flavithermus* WK1 | 7038665 | AFLV_RS12470 | superoxide dismutase family protein |
| 2026189 | *Bacillus albus* | 58159160 | sodC | superoxide dismutase [Cu—Zn] |
| 2026189 | *Bacillus albus* | 58156753 | ETJ91_RS05815 | superoxide dismutase |
| 2026189 | *Bacillus albus* | 58158145 | sodA | superoxide dismutase [Mn] |
| 2026189 | *Bacillus albus* | 58159657 | sodA | superoxide dismutase [Mn] |
| 293387 | *Bacillus altitudinis* | 66363449 | ID12_RS14280 | superoxide dismutase |

TABLE 5-continued

Exemplary superoxide dismutase proteins.

| NCBI taxonomic ID | Organism name | NCBI GeneID | Symbol | description |
|---|---|---|---|---|
| 293387 | Bacillus altitudinis | 66363808 | sodA | superoxide dismutase SodA |
| 293387 | Bacillus altitudinis | 66363455 | ID12_RS14310 | superoxide dismutase family protein |
| 1390 | Bacillus amyloliquefaciens | 75095683 | J5X95_RS19180 | superoxide dismutase |
| 1390 | Bacillus amyloliquefaciens | 75092220 | sodA | superoxide dismutase SodA |
| 1390 | Bacillus amyloliquefaciens | 75095691 | J5X95_RS19220 | superoxide dismutase family protein |
| 261594 | Bacillus anthracis str. 'Ames Ancestor' | 45024767 | sodC | superoxide dismutase [Cu—Zn] |
| 261594 | Bacillus anthracis str. 'Ames Ancestor' | 45021465 | GBAA_RS07560 | superoxide dismutase |
| 261594 | Bacillus anthracis str. 'Ames Ancestor' | 45025271 | sodA | superoxide dismutase [Mn] |
| 261594 | Bacillus anthracis str. 'Ames Ancestor' | 45024154 | sodA | superoxide dismutase [Mn] |
| 1529886 | Bacillus atrophaeus subsp. globigii | 23410139 | DJ95_RS07545 | superoxide dismutase |
| 1529886 | Bacillus atrophaeus subsp. globigii | 23410614 | sodA | superoxide dismutase SodA |
| 1529886 | Bacillus atrophaeus subsp. globigii | 23410146 | DJ95_RS07580 | superoxide dismutase family protein |
| 1396 | Bacillus cereus | 72451578 | sodC | superoxide dismutase [Cu—Zn] |
| 1396 | Bacillus cereus | 72448231 | FORC47_RS07605 | superoxide dismutase |
| 1396 | Bacillus cereus | 72452094 | sodA | superoxide dismutase [Mn] |
| 1396 | Bacillus cereus | 72450959 | sodA | superoxide dismutase [Mn] |
| 580165 | Bacillus cytotoxicus | 56419077 | CG479_RS18795 | superoxide dismutase family protein |
| 580165 | Bacillus cytotoxicus | 56416776 | CG479_RS06645 | superoxide dismutase |
| 580165 | Bacillus cytotoxicus | 56419510 | sodA | superoxide dismutase [Mn] |
| 580165 | Bacillus cytotoxicus | 56418547 | sodA | superoxide dismutase [Mn] |
| 260554 | Bacillus halotolerans | 50137397 | DIC78_RS20920 | superoxide dismutase |
| 260554 | Bacillus halotolerans | 50136996 | sodA | superoxide dismutase SodA |
| 260554 | Bacillus halotolerans | 50137390 | DIC78_RS20885 | superoxide dismutase family protein |
| 1925021 | Bacillus haynesii | 76972956 | H2R00_RS04200 | superoxide dismutase |
| 1925021 | Bacillus haynesii | 76972519 | sodA | superoxide dismutase SodA |
| 1925021 | Bacillus haynesii | 76972948 | H2R00_RS04160 | superoxide dismutase family protein |
| 483913 | Bacillus inaquosorum | 76978507 | M1M80_RS10800 | superoxide dismutase |
| 483913 | Bacillus inaquosorum | 76978913 | sodA | superoxide dismutase SodA |
| 483913 | Bacillus inaquosorum | 76978514 | M1M80_RS10835 | superoxide dismutase family protein |
| 1402 | Bacillus licheniformis | 66215742 | B14_RS11005 | superoxide dismutase |
| 1402 | Bacillus licheniformis | 66215332 | sodA | superoxide dismutase SodA |
| 1402 | Bacillus licheniformis | 66215734 | B14_RS10965 | superoxide dismutase family protein |
| 2026190 | Bacillus mobilis | 68606488 | sodC | superoxide dismutase [Cu—Zn] |
| 2026190 | Bacillus mobilis | 68607292 | BACERE00185_RS11415 | superoxide dismutase |
| 2026190 | Bacillus mobilis | 68605940 | sodA | superoxide dismutase [Mn] |
| 2026190 | Bacillus mobilis | 68608243 | sodA | superoxide dismutase [Mn] |
| 72360 | Bacillus mojavensis | 76982721 | HC660_RS10445 | superoxide dismutase |
| 72360 | Bacillus mojavensis | 76983122 | sodA | superoxide dismutase SodA |
| 72360 | Bacillus mojavensis | 76982728 | HC660_RS10480 | superoxide dismutase family protein |
| 1405 | Bacillus mycoides | 66265525 | EXW63_RS16910 | superoxide dismutase family protein |
| 1405 | Bacillus mycoides | 66263481 | EXW63_RS06690 | superoxide dismutase |
| 1405 | Bacillus mycoides | 66265007 | sodA | superoxide dismutase |
| 1405 | Bacillus mycoides | 66266149 | sodA | superoxide dismutase [Mn] |
| 2026187 | Bacillus pacificus | 69529677 | sodC | superoxide dismutase [Cu—Zn] |
| 2026187 | Bacillus pacificus | 69533018 | LMD38_RS19010 | superoxide dismutase |
| 2026187 | Bacillus pacificus | 69530337 | sodA | superoxide dismutase [Mn] |
| 2026187 | Bacillus pacificus | 69534536 | sodA | superoxide dismutase [Mn] |
| 1648923 | Bacillus paralicheniformis | 56672376 | sodA | superoxide dismutase SodA |
| 1648923 | Bacillus paralicheniformis | 56671950 | CP943_RS11750 | superoxide dismutase family protein |

TABLE 5-continued

Exemplary superoxide dismutase proteins.

| NCBI taxonomic ID | Organism name | NCBI GeneID | Symbol | description |
|---|---|---|---|---|
| 1648923 | Bacillus paralicheniformis | 56671942 | CP943_RS11710 | superoxide dismutase |
| 2026186 | Bacillus paranthracis | 75088079 | sodC | superoxide dismutase [Cu—Zn] |
| 2026186 | Bacillus paranthracis | 75084779 | NLJ82_RS07610 | superoxide dismutase |
| 2026186 | Bacillus paranthracis | 75088628 | sodA | superoxide dismutase [Mn] |
| 2026186 | Bacillus paranthracis | 75087415 | sodA | superoxide dismutase [Mn] |
| 527000 | Bacillus pseudomycoides DSM 12442 | 34217815 | BPMYX0001_RS06750 | superoxide dismutase |
| 527000 | Bacillus pseudomycoides DSM 12442 | 34215261 | sodA | superoxide dismutase [Mn] |
| 527000 | Bacillus pseudomycoides DSM 12442 | 34217406 | BPMYX0001_RS21250 | superoxide dismutase family protein |
| 1408 | Bacillus pumilus | 69520340 | C5P19_RS04310 | superoxide dismutase |
| 1408 | Bacillus pumilus | 69519970 | sodA | superoxide dismutase SodA |
| 1408 | Bacillus pumilus | 69520334 | C5P19_RS04280 | superoxide dismutase family protein |
| 561879 | Bacillus safensis | 61770171 | FX981_RS17050 | superoxide dismutase |
| 561879 | Bacillus safensis | 61769803 | sodA | superoxide dismutase SodA |
| 561879 | Bacillus safensis | 61770165 | FX981_RS17020 | superoxide dismutase family protein |
| 1177185 | Bacillus siamensis KCTC 13613 | 76426234 | Y79_RS0104425 | superoxide dismutase |
| 1177185 | Bacillus siamensis KCTC 13613 | 76428732 | sodA | superoxide dismutase SodA |
| 1177185 | Bacillus siamensis KCTC 13613 | 76426242 | Y79_RS0104465 | superoxide dismutase family protein |
| 1274524 | Bacillus sonorensis L12 | 79844765 | BSONL12_RS05440 | superoxide dismutase |
| 1274524 | Bacillus sonorensis L12 | 79843951 | BSONL12_RS01110 | superoxide dismutase |
| 1274524 | Bacillus sonorensis L12 | 79845195 | sodA | superoxide dismutase SodA |
| 1274524 | Bacillus sonorensis L12 | 79843958 | BSONL12_RS01145 | superoxide dismutase family protein |
| 293386 | Bacillus stratosphericus | 69435804 | sodA | superoxide dismutase |
| 293386 | Bacillus stratosphericus | 69437748 | LC033_RS13100 | superoxide dismutase |
| 293386 | Bacillus stratosphericus | 69437487 | LC033_RS11795 | superoxide dismutase family protein |
| 703612 | Bacillus subtilis subsp. spizizenii ATCC 6633 = JCM 2499 | 64303889 | EO946_RS10585 | superoxide dismutase |
| 703612 | Bacillus subtilis subsp. spizizenii ATCC 6633 = JCM 2499 | 64304294 | sodA | superoxide dismutase SodA |
| 703612 | Bacillus subtilis subsp. spizizenii ATCC 6633 = JCM 2499 | 64303896 | EO946_RS10620 | superoxide dismutase family protein |
| 224308 | Bacillus subtilis subsp. subtilis str. 168 | 939503 | sodF | superoxide dismutase (Fe2+-dependent) |
| 224308 | Bacillus subtilis subsp. subtilis str. 168 | 939502 | sodC | superoxide dismutase (exported lipoprotein) |
| 224308 | Bacillus subtilis subsp. subtilis str. 168 | 938052 | sodA | superoxide dismutase (Mn[2+]-dependent) |
| 527031 | Bacillus thuringiensis serovar berliner ATCC 10792 | 67469207 | sodC | superoxide dismutase [Cu—Zn] |
| 527031 | Bacillus thuringiensis serovar berliner ATCC 10792 | 67465949 | BTHUR0008_RS06905 | superoxide dismutase |
| 527031 | Bacillus thuringiensis serovar berliner ATCC 10792 | 67469685 | sodA | superoxide dismutase [Mn] |
| 527031 | Bacillus thuringiensis serovar berliner ATCC 10792 | 67468576 | sodA | superoxide dismutase [Mn] |
| 155322 | Bacillus toyonensis | 64186210 | sodC | superoxide dismutase [Cu—Zn] |
| 155322 | Bacillus toyonensis | 64182866 | I0K03_RS07270 | superoxide dismutase |

TABLE 5-continued

Exemplary superoxide dismutase proteins.

| NCBI taxonomic ID | Organism name | NCBI GeneID | Symbol | description |
|---|---|---|---|---|
| 155322 | *Bacillus toyonensis* | 64186708 | sodA | superoxide dismutase [Mn] |
| 155322 | *Bacillus toyonensis* | 64185587 | sodA | superoxide dismutase [Mn] |
| 2026188 | *Bacillus tropicus* | 56654675 | sodC | superoxide dismutase [Cu— Zn] |
| 2026188 | *Bacillus tropicus* | 56651323 | GM610_RS04365 | superoxide dismutase |
| 2026188 | *Bacillus tropicus* | 56654028 | sodA | superoxide dismutase [Mn] |
| 2026188 | *Bacillus tropicus* | 56655167 | sodA | superoxide dismutase [Mn] |
| 72361 | *Bacillus vallismortis* | 76987028 | D9779_RS11185 | superoxide dismutase |
| 72361 | *Bacillus vallismortis* | 76987433 | sodA | superoxide dismutase SodA |
| 72361 | *Bacillus vallismortis* | 76987035 | D9779_RS11220 | superoxide dismutase family protein |
| 492670 | *Bacillus velezensis* | 66322213 | NG74_RS09635 | superoxide dismutase family protein |
| 492670 | *Bacillus velezensis* | 66322205 | NG74_RS09595 | superoxide dismutase |
| 492670 | *Bacillus velezensis* | 66322632 | sodA | superoxide dismutase SodA |
| 1890302 | *Bacillus wiedmannii* | 51136620 | sodC | superoxide dismutase [Cu— Zn] |
| 1890302 | *Bacillus wiedmannii* | 51133060 | D4A37_RS07430 | superoxide dismutase |
| 1890302 | *Bacillus wiedmannii* | 51137122 | sodA | superoxide dismutase [Mn] |
| 1890302 | *Bacillus wiedmannii* | 51135983 | sodA | superoxide dismutase [Mn] |
| 1890302 | *Bacillus wiedmannii* | 51134840 | D4A37_RS16595 | superoxide dismutase |
| 1532 | *Blautia coccoides* | 78138336 | DY261_RS07595 | superoxide dismutase family protein |
| 1121114 | *Blautia producta* ATCC 27340 = DSM 2950 | 75055673 | GXM18_RS27160 | superoxide dismutase family protein |
| 1300222 | *Brevibacillus borstelensis* AK1 | 72737442 | I532_RS22295 | superoxide dismutase |
| 1300222 | *Brevibacillus borstelensis* AK1 | 72734893 | I532_RS08770 | superoxide dismutase |
| 1300222 | *Brevibacillus borstelensis* AK1 | 72736419 | I532_RS16830 | superoxide dismutase family protein |
| 1393 | *Brevibacillus brevis* | 61035084 | EL268_RS24975 | superoxide dismutase |
| 1393 | *Brevibacillus brevis* | 61034276 | EL268_RS20810 | superoxide dismutase |
| 1393 | *Brevibacillus brevis* | 61033010 | EL268_RS14365 | superoxide dismutase |
| 1393 | *Brevibacillus brevis* | 61035143 | EL268_RS25275 | superoxide dismutase family protein |
| 1121121 | *Brevibacillus laterosporus* DSM 25 | 70358748 | BrL25_RS25745 | superoxide dismutase |
| 1121121 | *Brevibacillus laterosporus* DSM 25 | 61080877 | BrL25_RS21670 | superoxide dismutase |
| 1121121 | *Brevibacillus laterosporus* DSM 25 | 61079368 | BrL25_RS13900 | superoxide dismutase |
| 2756 | *Brochothrix thermosphacta* | 66536742 | BFC19_RS03825 | superoxide dismutase |
| 2748 | *Carnobacterium divergens* | 56819036 | BFC22_RS09250 | superoxide dismutase |
| 2751 | *Carnobacterium maltaromaticum* | 56849594 | CKN98_RS10140 | superoxide dismutase |
| 1496 | *Clostridioides difficile* | 66354041 | KNZ77_RS08015 | superoxide dismutase |
| 1496 | *Clostridioides difficile* | 2828089 | NEWENTRY | Record to support submission of GeneRIFs for a gene not in Gene (*Bacillus difficilis*; *Clostridium difficile*; *Peptoclostridium difficile*. Use when strain, subtype, isolate, etc. is unspecified, or when different from all specified ones in Gene.). |
| 991791 | *Clostridium acetobutylicum* DSM 1731 | 44999036 | SMB_RS13085 | Fe—Mn family superoxide dismutase |
| 991791 | *Clostridium acetobutylicum* DSM 1731 | 44997868 | SMB_RS07075 | superoxide dismutase family protein |

TABLE 5-continued

Exemplary superoxide dismutase proteins.

| NCBI taxonomic ID | Organism name | NCBI GeneID | Symbol | description |
|---|---|---|---|---|
| 37659 | *Clostridium algidicarnis* | 75090956 | BV55_RS0110735 | superoxide dismutase |
| 37659 | *Clostridium algidicarnis* | 75091026 | BV55_RS0111130 | superoxide dismutase family protein |
| 1561 | *Clostridium baratii* | 60852023 | NPD11_RS02620 | superoxide dismutase |
| 1520 | *Clostridium beijerinckii* | 66344751 | KEC93_RS09470 | superoxide dismutase |
| 1520 | *Clostridium beijerinckii* | 66344469 | KEC93_RS08060 | superoxide dismutase |
| 413999 | *Clostridium botulinum* A str. ATCC 3502 | 5187439 | CBO_RS11140 | superoxide dismutase |
| 413999 | *Clostridium botulinum* A str. ATCC 3502 | 5184776 | CBO_RS02790 | superoxide dismutase |
| 1492 | *Clostridium butyricum* | 66379395 | NPD4_RS02680 | superoxide dismutase |
| 46867 | *Clostridium chauvoei* | 66301618 | BTM20_RS07030 | superoxide dismutase |
| 1494 | *Clostridium cochlearium* | 70576438 | CKV72_RS02330 | superoxide dismutase family protein |
| 1552 | *Clostridium estertheticum* subsp. *estertheticum* | 65307424 | A7L45_RS21050 | superoxide dismutase |
| 94869 | *Clostridium gasigenes* | 65311447 | J1C67_RS17775 | superoxide dismutase |
| 137838 | *Clostridium neonatale* | 68877560 | CNEONATNEC86_RS11330 | superoxide dismutase |
| 1542 | *Clostridium novyi* | 66319246 | DFH04_RS06705 | superoxide dismutase |
| 1542 | *Clostridium novyi* | 66320008 | DFH04_RS10555 | superoxide dismutase family protein |
| 1542 | *Clostridium novyi* | 66320199 | DFH04_RS11560 | Fe—Mn family superoxide dismutase |
| 1280689 | *Clostridium paraputrificum* AGR2156 | 42776507 | G594_RS0111240 | superoxide dismutase family protein |
| 1501 | *Clostridium pasteurianum* | 76626005 | AQ984_RS07650 | superoxide dismutase family protein |
| 1502 | *Clostridium perfringens* | 69449138 | KLF48_RS07155 | superoxide dismutase |
| 1345695 | *Clostridium saccharobutylicum* DSM 13864 | 55474666 | CLSA_RS10765 | superoxide dismutase |
| 1509 | *Clostridium sporogenes* | 69425562 | LA357_RS08045 | superoxide dismutase |
| 1509 | *Clostridium sporogenes* | 69424297 | LA357_RS01720 | superoxide dismutase family protein |
| 1509 | *Clostridium sporogenes* | 69427356 | LA357_RS17015 | Fe—Mn family superoxide dismutase |
| 360422 | *Clostridium tagluense* | 77242043 | LL095_RS13470 | superoxide dismutase |
| 360422 | *Clostridium tagluense* | 77241226 | LL095_RS09385 | superoxide dismutase |
| 1559 | *Clostridium tertium* | 65398045 | FXX58_RS03370 | superoxide dismutase |
| 1559 | *Clostridium tertium* | 65397629 | FXX58_RS01280 | superoxide dismutase |
| 212717 | *Clostridium tetani* E88 | 24255090 | CTC_RS00650 | superoxide dismutase |
| 212717 | *Clostridium tetani* E88 | 24255084 | CTC_RS02955 | superoxide dismutase family protein |
| 1519 | *Clostridium tyrobutyricum* | 29420514 | CTK_RS12445 | superoxide dismutase |
| 100884 | *Coprobacillus cateniformis* | 78229800 | HMPREF0273_RS0109935 | family protein superoxide dismutase |
| 1399 | *Cytobacillus firmus* | 67525780 | DY227_RS20930 | superoxide dismutase family protein |
| 1399 | *Cytobacillus firmus* | 67525219 | DY227_RS18030 | superoxide dismutase |
| 1399 | *Cytobacillus firmus* | 67525060 | DY227_RS17215 | superoxide dismutase |
| 665099 | *Cytobacillus oceanisediminis* | 65402547 | IQ19_RS06400 | superoxide dismutase family protein |
| 665099 | *Cytobacillus oceanisediminis* | 65405565 | IQ19_RS21665 | superoxide dismutase |
| 665099 | *Cytobacillus oceanisediminis* | 65402714 | IQ19_RS07240 | superoxide dismutase |
| 592028 | *Dialister invisus* DSM 15470 | 78277519 | GCWU000321_RS03850 | superoxide dismutase |
| 29394 | *Dolosigranulum pigrum* | 56765375 | B5772_RS06375 | superoxide dismutase |
| 1432052 | *Eisenbergiella tayi* | 56724017 | BEH84_RS20155 | superoxide dismutase family protein |
| 208479 | *Enterocloster bolteae* | 61858331 | CGC65_RS08415 | superoxide dismutase family protein |
| 358743 | *Enterocloster citroniae* | 77446576 | BM366_RS05980 | superoxide dismutase |

TABLE 5-continued

Exemplary superoxide dismutase proteins.

| NCBI taxonomic ID | Organism name | NCBI GeneID | Symbol | description |
|---|---|---|---|---|
| 358743 | Enterocloster citroniae | 77447280 | BM366_RS09560 | superoxide dismutase family protein |
| 1158606 | Enterococcus asini ATCC 700915 | 78365451 | I579_RS08845 | superoxide dismutase |
| 33945 | Enterococcus avium | 69567451 | AUF14_RS02710 | superoxide dismutase |
| 565655 | Enterococcus casseliflavus EC20 | 15142654 | ECBG_RS10265 | superoxide dismutase |
| 44008 | Enterococcus cecorum | 60871412 | DQL78_RS04645 | superoxide dismutase |
| 53345 | Enterococcus durans | 56743515 | CJZ72_RS09220 | superoxide dismutase |
| 1169293 | Enterococcus faecalis EnGen0336 | 60892904 | WMS_RS06055 | superoxide dismutase |
| 1352 | Enterococcus faecium | 66453837 | E6A31_RS04150 | superoxide dismutase |
| 1352 | Enterococcus faecium | 3293180 | NEWENTRY | Record to support submission of GeneRIFs for a gene not in Gene (Streptococcus faecium. Use when strain, subtype, isolate, etc. is unspecified, or when different from all specified ones in Gene.). |
| 1353 | Enterococcus gallinarum | 66474432 | EB54_RS11590 | superoxide dismutase |
| 1354 | Enterococcus hirae | 56788040 | A6J73_RS11950 | superoxide dismutase |
| 357441 | Enterococcus lactis | 66498016 | KU781_RS08785 | superoxide dismutase |
| 71451 | Enterococcus malodoratus | 79787296 | PGP85_RS13950 | superoxide dismutase |
| 53346 | Enterococcus mundtii | 60998774 | EM4838_RS03785 | superoxide dismutase |
| 71452 | Enterococcus raffinosus | 67040491 | J9537_RS09965 | superoxide dismutase |
| 417368 | Enterococcus thailandicus | 77487654 | CK496_RS08370 | superoxide dismutase |
| 1648 | Erysipelothrix rhusiopathiae | 60952536 | EL194_RS03710 | superoxide dismutase |
| 1235802 | Eubacterium plexicaudatum ASF492 | 78432353 | C823_RS06795 | superoxide dismutase |
| 39482 | Faecalicatena contorta | 70043705 | FY488_RS06420 | superoxide dismutase family protein |
| 1912855 | Faecalimonas umbilicata | 77478526 | FAEUMB_RS00975 | superoxide dismutase family protein |
| 292800 | Flavonifractor plautii | 63973604 | GXM20_RS12120 | superoxide dismutase |
| 292800 | Flavonifractor plautii | 63973553 | GXM20_RS11865 | superoxide dismutase family protein |
| 1379 | Gemella haemolysans | 78011071 | EL214_RS08270 | superoxide dismutase |
| 937593 | Geobacillus stearothermophilus ATCC 7953 | 69835380 | Z980_RS0113175 | superoxide dismutase |
| 937593 | Geobacillus stearothermophilus ATCC 7953 | 69833740 | sodA | superoxide dismutase SodA |
| 937593 | Geobacillus stearothermophilus ATCC 7953 | 69834618 | Z980_RS0109160 | superoxide dismutase family protein |
| 46124 | Granulicatella adiacens | 78412837 | K8O88_RS07515 | superoxide dismutase |
| 45668 | Halobacillus litoralis | 78006327 | GLW00_RS04945 | superoxide dismutase family protein |
| 45668 | Halobacillus litoralis | 78008076 | GLW00_RS13775 | superoxide dismutase |
| 45668 | Halobacillus litoralis | 78007262 | GLW00_RS09650 | superoxide dismutase family protein |
| 38875 | Heyndrickxia oleronia | 79870514 | KI370_RS24070 | superoxide dismutase |
| 38875 | Heyndrickxia oleronia | 79869222 | KI370_RS17535 | superoxide dismutase |
| 38875 | Heyndrickxia oleronia | 79867177 | sodA | superoxide dismutase SodA |
| 38875 | Heyndrickxia oleronia | 79870723 | KI370_RS25120 | superoxide dismutase family protein |
| 46224 | Heyndrickxia sporothermodurans | 62497427 | sodA | superoxide dismutase SodA |
| 46224 | Heyndrickxia sporothermodurans | 62498687 | B5V89_RS09755 | superoxide dismutase family protein |
| 154046 | Hungatella hathewayi | 61910901 | GNE07_RS09325 | superoxide dismutase |
| 261299 | Intestinibacter bartlettii | 68213444 | FXW45_RS01165 | superoxide dismutase family protein |

TABLE 5-continued

Exemplary superoxide dismutase proteins.

| NCBI taxonomic ID | Organism name | NCBI GeneID | Symbol | description |
|---|---|---|---|---|
| 261299 | *Intestinibacter bartlettii* | 68214032 | FXW45_RS04125 | Fe—Mn family superoxide dismutase |
| 1297617 | *Intestinimonas butyriciproducens* | 60290807 | BIV19_RS02040 | superoxide dismutase |
| 537973 | *Lacticaseibacillus paracasei* subsp. *paracasei* 8700:2 | 57090545 | LBPG_RS09280 | superoxide dismutase |
| 2749961 | *Lactococcus carnosus* | 71636613 | BHS00_RS08120 | superoxide dismutase |
| 1295826 | *Lactococcus cremoris* subsp. *cremoris* KW2 | 61108730 | KW2_RS02035 | superoxide dismutase |
| 1363 | *Lactococcus garvieae* | 61074949 | 16G86_RS10400 | superoxide dismutase |
| 1358 | *Lactococcus lactis* | 69712452 | H0A38_RS01885 | superoxide dismutase |
| 1940789 | *Lactococcus petauri* | 75143064 | Igb_RS01475 | superoxide dismutase |
| 1366 | *Lactococcus raffinolactis* | 47267490 | CMV25_RS02570 | superoxide dismutase |
| 1293592 | *Latilactobacillus curvatus* JCM 1096 = DSM 20019 | 49610411 | LCU_RS03060 | superoxide dismutase |
| 1599 | *Latilactobacillus sakei* | 57133753 | GJ664_RS08450 | superoxide dismutase |
| 1122150 | *Liquorilactobacillus nagelii* DSM 13675 | 78522855 | G6073_RS10790 | superoxide dismutase |
| 1552123 | *Listeria booriae* | 58717044 | EP57_RS06400 | superoxide dismutase |
| 2838249 | *Listeria cossartiae* | 69674735 | LAX71_RS03775 | superoxide dismutase |
| 1642 | *Listeria innocua* | 57122066 | GH761_RS01260 | superoxide dismutase |
| 1642 | *Listeria innocua* | 57123181 | GH761_RS06865 | superoxide dismutase |
| 202751 | *Listeria ivanovii* subsp. *ivanovii* | 57076380 | JL52_RS07350 | superoxide dismutase |
| 529731 | *Listeria marthii* | 72458209 | LAX73_RS05935 | superoxide dismutase |
| 169963 | *Listeria monocytogenes* EGD-e | 986791 | sod | superoxide dismutase |
| 683837 | *Listeria seeligeri* serovar 1/2b str. SLCC3954 | 32489765 | LSE_RS06750 | superoxide dismutase |
| 1643 | *Listeria welshimeri* | 61189332 | CKV90_RS07415 | superoxide dismutase |
| 2115968 | *Lysinibacillus capsici* | 74906096 | LCP48_RS15320 | superoxide dismutase |
| 2115968 | *Lysinibacillus capsici* | 74903471 | LCP48_RS02195 | superoxide dismutase family protein |
| 28031 | *Lysinibacillus fusiformis* | 29439767 | HR49_RS08290 | superoxide dismutase |
| 28031 | *Lysinibacillus fusiformis* | 29440514 | HR49_RS21910 | superoxide dismutase family protein |
| 1421 | *Lysinibacillus sphaericus* | 69661880 | EYB33_RS15330 | superoxide dismutase |
| 1421 | *Lysinibacillus sphaericus* | 69659309 | EYB33_RS02475 | superoxide dismutase family protein |
| 1421 | *Lysinibacillus sphaericus* | 69659308 | EYB33_RS02470 | superoxide dismutase family protein |
| 1855823 | *Macrococcus canis* | 75266884 | L2Z53_RS07065 | superoxide dismutase |
| 69966 | *Macrococcus caseolyticus* | 61128910 | I6G25_RS01905 | superoxide dismutase |
| 42858 | *Mammaliicoccus lentus* | 79849027 | JT690_RS02380 | superoxide dismutase |
| 1296 | *Mammaliicoccus sciuri* | 33959503 | CEP64_RS19570 | superoxide dismutase |
| 71237 | *Mammaliicoccus vitulinus* | 64116511 | 16J10_RS05245 | superoxide dismutase |
| 706434 | *Megasphaera micronuciformis* F0359 | 78568989 | HMPREF9429_RS05265 | superoxide dismutase |
| 33970 | *Melissococcus plutonius* | 57043927 | DAT869_RS06820 | superoxide dismutase |
| 1525 | *Moorella thermoacetica* | 45617959 | MOTHA_RS09895 | superoxide dismutase |
| 1397 | *Niallia circulans* | 56350965 | FOC77_RS19785 | superoxide dismutase family protein |
| 1397 | *Niallia circulans* | 56350425 | FOC77_RS17085 | superoxide dismutase |
| 1397 | *Niallia circulans* | 56350225 | FOC77_RS16085 | superoxide dismutase |
| 1397 | *Niallia circulans* | 56348828 | FOC77_RS09100 | superoxide dismutase |
| 44250 | *Paenibacillus alvei* | 79812132 | M5X17_RS04805 | superoxide dismutase |
| 44250 | *Paenibacillus alvei* | 79814510 | M5X17_RS16695 | superoxide dismutase family protein |
| 44250 | *Paenibacillus alvei* | 79812145 | M5X17_RS04870 | Fe—Mn family superoxide dismutase |

TABLE 5-continued

Exemplary superoxide dismutase proteins.

| NCBI taxonomic ID | Organism name | NCBI GeneID | Symbol | description |
|---|---|---|---|---|
| 1451 | Paenibacillus amylolyticus | 72507819 | BK129_RS28795 | superoxide dismutase |
| 1451 | Paenibacillus amylolyticus | 72504297 | BK129_RS10725 | superoxide dismutase |
| 1451 | Paenibacillus amylolyticus | 72507810 | BK129_RS28750 | Fe—Mn family superoxide dismutase |
| 130049 | Paenibacillus dendritiformis | 73385461 | L6439_RS14625 | superoxide dismutase |
| 130049 | Paenibacillus dendritiformis | 73382951 | L6439_RS02075 | superoxide dismutase |
| 130049 | Paenibacillus dendritiformis | 73385345 | L6439_RS14045 | superoxide dismutase family protein |
| 130049 | Paenibacillus dendritiformis | 73382963 | L6439_RS02135 | Fe—Mn family superoxide dismutase |
| 1870820 | Paenibacillus ihbetae | 48308695 | BBD41_RS10725 | superoxide dismutase |
| 1870820 | Paenibacillus ihbetae | 48308531 | BBD41_RS09890 | superoxide dismutase family protein |
| 1870820 | Paenibacillus ihbetae | 48308681 | BBD41_RS10655 | Fe—Mn family superoxide dismutase |
| 147375 | Paenibacillus larvae subsp. larvae | 64220502 | ERICIV_RS19060 | superoxide dismutase |
| 147375 | Paenibacillus larvae subsp. larvae | 64218138 | ERICIV_RS06610 | superoxide dismutase |
| 147375 | Paenibacillus larvae subsp. larvae | 64220488 | ERICIV_RS18985 | Fe—Mn family superoxide dismutase |
| 1349780 | Paenibacillus lautus NBRC 15380 | 72768694 | PLA01S_RS27810 | superoxide dismutase |
| 1349780 | Paenibacillus lautus NBRC 15380 | 72768707 | PLA01S_RS27875 | Fe—Mn family superoxide dismutase |
| 1349780 | Paenibacillus lautus NBRC 15380 | 72763763 | PLA01S_RS02640 | superoxide dismutase family protein |
| 1349780 | Paenibacillus lautus NBRC 15380 | 72763737 | PLA01S_RS02480 | superoxide dismutase family protein |
| 44252 | Paenibacillus macerans | 77009568 | DYE26_RS18555 | superoxide dismutase |
| 44252 | Paenibacillus macerans | 77006234 | DYE26_RS01075 | superoxide dismutase |
| 44252 | Paenibacillus macerans | 77009561 | DYE26_RS18520 | Fe—Mn family superoxide dismutase |
| 189426 | Paenibacillus odorifer | 31569237 | PODO_RS02945 | superoxide dismutase |
| 189426 | Paenibacillus odorifer | 31569243 | PODO_RS02975 | Fe—Mn family superoxide dismutase |
| 1087481 | Paenibacillus peoriae KCTC 3763 | 71025681 | KQI_RS0118905 | superoxide dismutase |
| 1087481 | Paenibacillus peoriae KCTC 3763 | 71025689 | KQI_RS0118945 | Fe—Mn family superoxide dismutase |
| 1406 | Paenibacillus polymyxa | 66574192 | FGY93_RS04285 | superoxide dismutase |
| 1406 | Paenibacillus polymyxa | 66574184 | FGY93_RS04245 | Fe—Mn family superoxide dismutase |
| 49283 | Paenibacillus thiaminolyticus | 76994919 | FLT43_RS02850 | superoxide dismutase family protein |
| 49283 | Paenibacillus thiaminolyticus | 76998194 | FLT43_RS19725 | superoxide dismutase |
| 49283 | Paenibacillus thiaminolyticus | 76995040 | FLT43_RS03480 | superoxide dismutase |
| 49283 | Paenibacillus thiaminolyticus | 76998203 | FLT43_RS19775 | Fe—Mn family superoxide dismutase |
| 528191 | Paenibacillus xylanexedens | 32215159 | BS614_RS06910 | superoxide dismutase |
| 528191 | Paenibacillus xylanexedens | 32215168 | BS614_RS06955 | Fe—Mn family superoxide dismutase |
| 1505 | Paeniclostridium sordellii | 57936353 | RSJ16_RS11840 | superoxide dismutase |
| 1505 | Paeniclostridium sordellii | 57936322 | RSJ16_RS11685 | superoxide dismutase family protein |
| 1490 | Paraclostridium bifermentans | 67474159 | KXZ80_RS15610 | superoxide dismutase |
| 1490 | Paraclostridium bifermentans | 67473031 | KXZ80_RS09970 | superoxide dismutase |
| 1490 | Paraclostridium bifermentans | 67471480 | KXZ80_RS02215 | superoxide dismutase family protein |
| 1426 | Parageobacillus thermoglucosidasius | 56926936 | BCV53_RS16030 | superoxide dismutase |

TABLE 5-continued

Exemplary superoxide dismutase proteins.

| NCBI taxonomic ID | Organism name | NCBI GeneID | Symbol | description |
|---|---|---|---|---|
| 1426 | *Parageobacillus thermoglucosidasius* | 56927088 | sodA | superoxide dismutase SodA |
| 1426 | *Parageobacillus thermoglucosidasius* | 56923888 | BCV53_RS00100 | superoxide dismutase family protein |
| 33033 | *Parvimonas micra* | 71955359 | DYJ31_RS04860 | superoxide dismutase |
| 450367 | *Peribacillus frigoritolerans* | 72367349 | L8956_RS05605 | superoxide dismutase family protein |
| 450367 | *Peribacillus frigoritolerans* | 72369504 | L8956_RS16380 | superoxide dismutase |
| 450367 | *Peribacillus frigoritolerans* | 72369659 | sodA | superoxide dismutase SodA |
| 1349754 | *Peribacillus simplex* NBRC 15720 = DSM 1321 | 56475443 | BS1321_RS22295 | superoxide dismutase |
| 1349754 | *Peribacillus simplex* NBRC 15720 = DSM 1321 | 56475295 | sodA | superoxide dismutase SodA |
| 1349754 | *Peribacillus simplex* NBRC 15720 = DSM 1321 | 56472464 | BS1321_RS07045 | superoxide dismutase family protein |
| 33025 | *Phascolarctobacterium faecium* | 49406307 | PFJ30894_RS03090 | superoxide dismutase |
| 412384 | *Priestia aryabhattai* | 48015425 | CR091_RS24255 | superoxide dismutase family protein |
| 412384 | *Priestia aryabhattai* | 48013327 | CR091_RS13620 | superoxide dismutase |
| 412384 | *Priestia aryabhattai* | 48014989 | sodA | superoxide dismutase SodA |
| 412384 | *Priestia aryabhattai* | 48012678 | CR091_RS10315 | superoxide dismutase family protein |
| 135735 | *Priestia endophytica* | 72762384 | A4R27_RS22825 | superoxide dismutase |
| 135735 | *Priestia endophytica* | 72759379 | sodA | superoxide dismutase SodA |
| 135735 | *Priestia endophytica* | 72758128 | A4R27_RS01150 | superoxide dismutase family protein |
| 86664 | *Priestia flexa* | 72445662 | sodA | superoxide dismutase SodA |
| 86664 | *Priestia flexa* | 72446092 | H1W68_RS19010 | superoxide dismutase family protein |
| 86664 | *Priestia flexa* | 72443997 | H1W68_RS08535 | superoxide dismutase family protein |
| 1404 | *Priestia megaterium* | 64144592 | CE057_RS01705 | superoxide dismutase family protein |
| 1404 | *Priestia megaterium* | 64147515 | CE057_RS16355 | superoxide dismutase |
| 1404 | *Priestia megaterium* | 64145779 | sodA | superoxide dismutase SodA |
| 1404 | *Priestia megaterium* | 64149086 | CE057_RS24280 | superoxide dismutase family protein |
| 1123011 | *Pseudobutyrivibrio ruminis* DSM 9787 | 78377300 | CRN97_RS06605 | superoxide dismutase |
| 301301 | *Roseburia hominis* | 77459290 | FYB86_RS08395 | superoxide dismutase family protein |
| 1073842 | *Rossellomorea aquimaris* TF-12 | 67738896 | IQI_RS04480 | superoxide dismutase |
| 1073842 | *Rossellomorea aquimaris* TF-12 | 67741871 | IQI_RS19605 | superoxide dismutase family protein |
| 1073842 | *Rossellomorea aquimaris* TF-12 | 67740318 | IQI_RS11690 | superoxide dismutase family protein |
| 189381 | *Rossellomorea marisflavi* | 42290732 | sodA | superoxide dismutase SodA |
| 189381 | *Rossellomorea marisflavi* | 42293745 | AF331_RS17515 | superoxide dismutase family protein |
| 189381 | *Rossellomorea marisflavi* | 42293233 | AF331_RS14915 | superoxide dismutase family protein |
| 218284 | *Rossellomorea vietnamensis* | 77238104 | BN987_RS17475 | superoxide dismutase family protein |
| 218284 | *Rossellomorea vietnamensis* | 77235539 | BN987_RS04115 | superoxide dismutase |
| 218284 | *Rossellomorea vietnamensis* | 77236782 | BN987_RS10620 | superoxide dismutase family protein |
| 45670 | *Salinicoccus roseus* | 77844005 | SN16_RS00430 | superoxide dismutase |
| 1653434 | *Sellimonas intestinalis* | 56803973 | DW871_RS14800 | superoxide dismutase |
| 254758 | *Siminovitchia fortis* | 56392146 | FS666_RS11835 | superoxide dismutase family protein |

TABLE 5-continued

Exemplary superoxide dismutase proteins.

| NCBI taxonomic ID | Organism name | NCBI GeneID | Symbol | description |
|---|---|---|---|---|
| 254758 | Siminovitchia fortis | 56390872 | FS666_RS05465 | superoxide dismutase |
| 254758 | Siminovitchia fortis | 56389924 | sodA | superoxide dismutase SodA |
| 254758 | Siminovitchia fortis | 56393146 | FS666_RS16835 | superoxide dismutase family protein |
| 985762 | Staphylococcus agnetis | 57691661 | GJE18_RS05835 | superoxide dismutase |
| 985002 | Staphylococcus argenteus | 66839743 | SAMSHR1132_RS07300 | superoxide dismutase |
| 985002 | Staphylococcus argenteus | 66838442 | SAMSHR1132_RS00560 | superoxide dismutase |
| 29378 | Staphylococcus arlettae | 61680709 | DX957_RS06685 | superoxide dismutase |
| 93061 | Staphylococcus aureus subsp. aureus NCTC 8325 | 3919804 | SAOUHSC_00093 | superoxide dismutase |
| 93061 | Staphylococcus aureus subsp. aureus NCTC 8325 | 3920105 | SAOUHSC_01653 | superoxide dismutase |
| 93061 | Staphylococcus aureus subsp. aureus NCTC 8325 | 3925961 | NEWENTRY | Record to support submission of GeneRIFs for a gene not in Gene (Staphylococcus aureus NCTC 8325; Staphylococcus aureus subsp. aureus str. NCTC 8325; Staphylococcus aureus subsp. aureus strain NCTC 8325). |
| 29379 | Staphylococcus auricularis | 64982149 | I6G39_RS05795 | superoxide dismutase |
| 2742203 | Staphylococcus borealis | 74185931 | AK212_RS04865 | superoxide dismutase |
| 72758 | Staphylococcus capitis subsp. capitis | 77313602 | NF392_RS06120 | superoxide dismutase |
| 29380 | Staphylococcus caprae | 58051100 | JMUB898_RS06630 | superoxide dismutase |
| 1281 | Staphylococcus carnosus | 60545135 | DYE31_RS06610 | superoxide dismutase |
| 46126 | Staphylococcus chromogenes | 66914569 | C7N56_RS04825 | superoxide dismutase |
| 74706 | Staphylococcus coagulans | 72414310 | KM149_RS06165 | superoxide dismutase |
| 29382 | Staphylococcus cohnii | 58097449 | DYB52_RS06495 | superoxide dismutase |
| 70255 | Staphylococcus condimenti | 62692988 | BTZ13_RS06835 | superoxide dismutase |
| 53344 | Staphylococcus delphini | 77324946 | MUA44_RS06540 | superoxide dismutase |
| 586733 | Staphylococcus devriesei | 48887892 | DYD94_RS06055 | superoxide dismutase |
| 1282 | Staphylococcus epidermidis | 50018644 | EQW00_RS06480 | superoxide dismutase |
| 246432 | Staphylococcus equorum | 69845810 | I6I25_RS05040 | superoxide dismutase |
| 46127 | Staphylococcus felis | 48058429 | *C7J90_RS09340* | *superoxide dismutase* |
| 1293 | Staphylococcus gallinarum | 69851527 | *K3U27_RS05230* | *superoxide dismutase* |
| 1283 | Staphylococcus haemolyticus | 58062446 | AV904_RS05900 | superoxide dismutase |
| 1290 | Staphylococcus hominis | 58107233 | EGX58_RS10225 | superoxide dismutase |
| 1284 | Staphylococcus hyicus | 41073147 | SHYC_RS06585 | superoxide dismutase |
| 29384 | Staphylococcus kloosii | 69905304 | C7J89_RS08115 | superoxide dismutase |
| 28035 | Staphylococcus lugdunensis | 58089653 | AL499_RS01165 | superoxide dismutase |
| 214473 | Staphylococcus nepalensis | 66776762 | BJG89_RS07020 | superoxide dismutase |
| 45972 | Staphylococcus pasteuri | 72470310 | I6I26_RS06225 | superoxide dismutase |
| 170573 | Staphylococcus pettenkoferi | 42042632 | CEP67_RS02240 | superoxide dismutase |

TABLE 5-continued

Exemplary superoxide dismutase proteins.

| NCBI taxonomic ID | Organism name | NCBI GeneID | Symbol | description |
|---|---|---|---|---|
| 283734 | Staphylococcus pseudintermedius | 66876554 | JC286_RS06260 | superoxide dismutase |
| 33028 | Staphylococcus saccharolyticus | 66813937 | DMB76_RS06005 | superoxide dismutase |
| 29385 | Staphylococcus saprophyticus | 66867432 | DV527_RS06540 | superoxide dismutase |
| 1295 | Staphylococcus schleiferi | 64047432 | FY370_RS04705 | superoxide dismutase |
| 2912228 | Staphylococcus shinii | 79050275 | J5E45_RS01420 | superoxide dismutase |
| 1286 | Staphylococcus simulans | 77331540 | MUA87_RS06425 | superoxide dismutase |
| 61015 | Staphylococcus succinus | 43012574 | BK815_RS02585 | superoxide dismutase |
| 94138 | Staphylococcus ureilyticus | 78332398 | MUA21_RS06525 | superoxide dismutase |
| 1292 | Staphylococcus warneri | 58060017 | D3P10_RS06280 | superoxide dismutase |
| 1288 | Staphylococcus xylosus | 45496908 | SXYLSMQ121_RS06370 | superoxide dismutase |
| 1311 | Streptococcus agalactiae | 66885740 | sodA | superoxide dismutase SodA |
| 29389 | Streptococcus alactolyticus | 79926497 | sodA | superoxide dismutase SodA |
| 1328 | Streptococcus anginosus | 58054995 | SanJ4211_RS02880 | superoxide dismutase |
| 113107 | Streptococcus australis | 61451786 | sodA | superoxide dismutase SodA |
| 1329 | Streptococcus canis | 66916442 | sodA | superoxide dismutase SodA |
| 76860 | Streptococcus constellatus | 58099363 | DYD51_RS02755 | superoxide dismutase |
| 889201 | Streptococcus cristatus ATCC 51100 | 48423028 | sodA | superoxide dismutase SodA |
| 1334 | Streptococcus dysgalactiae | 79939998 | sodA | superoxide dismutase SodA |
| 119602 | Streptococcus dysgalactiae subsp. equisimilis | 66901191 | sodA | superoxide dismutase SodA |
| 40041 | Streptococcus equi subsp. zooepidemicus | 64011441 | sodA | superoxide dismutase SodA |
| 1335 | Streptococcus equinus | 63970474 | sodA | superoxide dismutase SodA |
| 315405 | Streptococcus gallolyticus | 57921731 | sodA | superoxide dismutase SodA |
| 1302 | Streptococcus gordonii | 61440974 | sodA | superoxide dismutase SodA |
| 254785 | Streptococcus halichoeri | 67413521 | sodA | superoxide dismutase SodA |
| 1337 | Streptococcus hyointestinalis | 78356502 | DYA54_RS05230 | superoxide dismutase |
| 102684 | Streptococcus infantarius | 69902220 | sodA | superoxide dismutase SodA |
| 68892 | Streptococcus infantis | 69898803 | sodA | superoxide dismutase SodA |
| 386894 | Streptococcus iniae 9117 | 66799658 | sodA | superoxide dismutase SodA |
| 1338 | Streptococcus intermedius | 57844370 | DQN42_RS02845 | superoxide dismutase |
| 150055 | Streptococcus lutetiensis | 58527905 | DQN23_RS02910 | superoxide dismutase |
| 59310 | Streptococcus macedonicus | 76467515 | sodA | superoxide dismutase SodA |
| 28037 | Streptococcus mitis | 61380281 | sodA | superoxide dismutase SodA |
| 1309 | Streptococcus mutans | 66817909 | sodA | superoxide dismutase SodA |
| 210007 | Streptococcus mutans UA159 | 2830791 | NEWENTRY | Record to support submission of GeneRIFs for a gene not in Gene (Streptococcus mutans str. UA159). |

TABLE 5-continued

Exemplary superoxide dismutase proteins.

| NCBI taxonomic ID | Organism name | NCBI GeneID | Symbol | description |
|---|---|---|---|---|
| 655813 | Streptococcus oralis ATCC 35037 | 49599987 | sodA | superoxide dismutase SodA |
| 1282664 | Streptococcus oralis subsp. tigurinus AZ_3a | 31538202 | H354_RS21245 | superoxide dismutase [Mn] |
| 1318 | Streptococcus parasanguinis | 75175086 | sodA | superoxide dismutase SodA |
| 1501662 | Streptococcus parasuis | 78826743 | sodA | superoxide dismutase SodA |
| 1348 | Streptococcus parauberis | 66816732 | sodA | superoxide dismutase SodA |
| 197614 | Streptococcus pasteurianus | 64018381 | sodA | superoxide dismutase SodA |
| 1313 | Streptococcus pneumoniae | 66805911 | sodA | superoxide dismutase SodA |
| 1054460 | Streptococcus pseudopneumoniae IS7493 | 45218084 | sodA | superoxide dismutase SodA |
| 361101 | Streptococcus pseudoporcinus | 58554979 | sodA | superoxide dismutase SodA |
| 1314 | Streptococcus pyogenes | 69900637 | sodA | superoxide dismutase SodA |
| 1917441 | Streptococcus ruminantium | 52229880 | sodA | superoxide dismutase SodA |
| 1304 | Streptococcus salivarius | 58024602 | sodA | superoxide dismutase SodA |
| 888817 | Streptococcus sanguinis SK405 | 61536031 | sodA | superoxide dismutase SodA |
| 1310 | Streptococcus sobrinus | 57973088 | sodA | superoxide dismutase SodA |
| 568814 | Streptococcus suis BM407 | 8155249 | sodA | superoxide dismutase SodA |
| 1308 | Streptococcus thermophilus | 66898620 | sodA | superoxide dismutase SodA |
| 1349 | Streptococcus uberis | 58023708 | sodA | superoxide dismutase SodA |
| 1343 | Streptococcus vestibularis | 77297251 | sodA | superoxide dismutase SodA |
| 361277 | Terribacillus saccharophilus | 72754744 | CHH56_RS03595 | superoxide dismutase |
| 361277 | Terribacillus saccharophilus | 72754615 | CHH56_RS02945 | superoxide dismutase |
| 51669 | Tetragenococcus halophilus | 64054189 | AC806_RS06175 | superoxide dismutase |
| 290335 | Tetragenococcus koreensis | 69985149 | C7K43_RS04240 | superoxide dismutase |
| 69824 | Thomasclavelia cocleata | 78287354 | BMW96_RS01555 | superoxide dismutase family protein |
| 1547 | Thomasclavelia ramosa | 64197927 | I6I62_RS16040 | superoxide dismutase family protein |
| 29348 | Thomasclavelia spiroformis | 67386278 | FY306_RS04480 | superoxide dismutase family protein |
| 154288 | Turicibacter sanguinis | 60059338 | HLK68_RS10515 | superoxide dismutase |
| 2738 | Vagococcus fluvialis | 69881322 | K5K99_RS08260 | superoxide dismutase |
| 81947 | Vagococcus lutrae | 72384625 | M2919_RS02640 | superoxide dismutase |
| 39777 | Veillonella atypica | 57774683 | FY355_RS06915 | superoxide dismutase |
| 29466 | Veillonella parvula | 69654300 | CKV63_RS08870 | superoxide dismutase |
| 1482 | Virgibacillus halodenitrificans | 71514475 | BME96_RS08815 | superoxide dismutase |
| 1482 | Virgibacillus halodenitrificans | 71515169 | BME96_RS12350 | superoxide dismutase family protein |
| 1482 | Virgibacillus halodenitrificans | 71516185 | BME96_RS17550 | superoxide dismutase family protein |
| 1473 | Virgibacillus pantothenticus | 66872821 | KBP50_RS20400 | superoxide dismutase family protein |
| 1473 | Virgibacillus pantothenticus | 66869870 | KBP50_RS05645 | superoxide dismutase family protein |
| 1473 | Virgibacillus pantothenticus | 66870428 | KBP50_RS08435 | superoxide dismutase |
| 1473 | Virgibacillus pantothenticus | 66870320 | KBP50_RS07895 | superoxide dismutase |
| 1121088 | Weizmannia coagulans DSM 1 = ATCC 7050 | 29812583 | sodA | superoxide dismutase SodA |

Superoxide Dismutases from Gas Fermentation Hosts:

Additional superoxide dismutase gene sequences were pulled from microbial sources that perform gas fermentation, including *C. autoethanogenum, C. necator*, and related.

TABLE 6

Exemplary superoxide dismutase proteins.

| GenBank accession no. | Gene description |
|---|---|
| AGY75202.1 | superoxide dismutase copper/zinc binding protein [*Clostridium autoethanogenum* DSM 10061] |
| CAJ95901.1 | Copper-Zinc superoxide dismutase [*Cupriavidus necator* H16] |
| ADK16026.1 | Cu—Zn superoxide dismutase [*Clostridium ljungdahlii* DSM 13528] |
| ADE86041.1 | superoxide dismutase (Fe) [*Rhodobacter capsulatus* SB 1003] |
| CAJ91758.1 | superoxide dismutase (Fe) [*Cupriavidus necator* H16] |

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

EMBODIMENTS OF THE DISCLOSURE

Embodiment 1. A process for continuous co-production of at least one chemical product and at least one heterologous protein product comprising:
 a) providing a continuous bioreactor;
 b) introducing to the bioreactor a recombinant C1-fixing microorganism capable of co-producing at least one chemical product and at least one heterologous protein, a gaseous substrate comprising one or more of CO, $CO_2$, and $H_2$, and a liquid growth medium;
 c) continuously culturing the recombinant C1-fixing microorganism thereby generating a gas fermentation broth comprising 1) the at least one chemical product, 2) the at least one heterologous protein product, and 3) microbial biomass;
 d) continuously removing a portion of the gas fermentation broth in a first stream;
 e) continuously removing the at least one chemical product in a second stream; and
 f) continuously recovering the at least one heterologous protein from the microbial biomass from the first stream.

A method for continuous co-production of at least one targeted chemical product and at least one heterologous protein product, the method comprising:
 a) culturing in a bioreactor, a recombinant C1-fixing microorganism capable of co-production of at least one targeted chemical product and at least one heterologous protein having a unit value in the presence of a gaseous substrate comprising one or more of CO, $CO_2$, and $H_2$, and a liquid growth medium; and
 b) recovering the at least one targeted chemical product and the at least one heterologous protein wherein the at least one heterologous protein is recovered in an amount from about 0.1% to about 1% grams/dry cell weight/day of the at least one heterologous protein produced.

The method of claim 2, wherein the heterologous protein has a high market value.

The method of claim 2, wherein the heterologous protein is a high-value, specialized protein.

The method of claim 4, wherein the heterologous protein is an antioxidant or an antioxidant enzyme.

The method of claim 5, wherein the antioxidant is selected from catalase, glutathione peroxidase, vitamin C, vitamin E, beta-carotene, carotenoids, flavonoids, superoxide dismutase, or any combination thereof.

The method of claim 6, wherein the antioxidant enzyme is a superoxide dismutase selected from SOD006, SOD007, SOD009, and SOD010.

The method of claim 1, wherein the at least one heterologous protein is squid ring teeth (SRT) protein and the at least one chemical product is ethylene.

The method of claim 1, wherein the at least one chemical product is ethylene.

The method of claim 1, further comprising separating the microbial biomass from the first stream before recovering the heterologous protein.

A method for continuous co-production of at least one targeted chemical product and at least one exogenous protein product, the method comprising:
  a) culturing, in a bioreactor, a recombinant C1-fixing microorganism capable of co-production of at least one targeted chemical product and at least one heterologous protein in the presence of a gaseous substrate comprising one or more of CO, $CO_2$, and $H_2$, and a liquid growth medium;
  b) generating microbial biomass having a unit value, at least one targeted chemical product, and at least one heterologous protein have a unit value, wherein the unit value of the heterologous protein is greater than the unit value of the microbial biomass; and
  c) recovering the at least one heterologous protein in an amount of at least 15% of a sum value of the unit value of the heterologous protein and the unit value of the microbial biomass.

The method of claim 11, wherein recovering of step c) of the at least one heterologous protein is in an amount of at least 1% of the sum value.

The method of claim 4, wherein the high-value, specialized protein is selected from ubiquinone, coenzyme Q10, copper/zinc and manganese-dependent superoxide dismutase, iron-dependent catalase, selenium-dependent glutathione peroxidase, albumin, ceruloplasmin, metallothionein, ferritin, myoglobin, transferrin, haptoglobins, ceruloplasmin, heat shock proteins, or any combination thereof.

The method of claim 1, wherein the at least one chemical product is selected from 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, keto-adipic acid, 1,3-hexanediol, 3-methyl-2-butanol, 2-buten-1-ol, isovalerate, isoamyl alcohol, monoethylene glycol, or any combination thereof.

The method of claim 1, further comprising the recombinant microorganism comprising a disruptive mutation in one or more genes.

The method of claim 1, wherein the recombinant microorganism comprises a parental microorganism selected from the group consisting of *Acetobacterium woodii*, *Alkalibaculum bacchii*, *Blautia producta*, *Butyribacterium methylotrophicum*, *Clostridium aceticum*, *Clostridium autoethanogenum*, *Clostridium carboxidivorans*, *Clostridium coskatii*, *Clostridium drakei*, *Clostridium formicoaceticum*, *Clostridium ljungdahlii*, *Clostridium magnum*, *Clostridium ragsdalei*, *Clostridium scatologenes*, *Eubacterium limosum*, *Moorella thermautotrophica*, *Moorella thermoacetica*, *Oxobacter pfennigii*, *Sporomusa ovata*, *Sporomusa silvacetica*, *Sporomusa sphaeroides*, *Cupriavidus necator* and *Thermoanaerobacter kivui*.

The method of claim 11, wherein the chemical product is one or more of ethylene, ethanol, acetone, isopropanol, or any combination thereof.

The method of claim 1, further comprising the microbial biomass and at least one excipient.

The method of claim 1, wherein the microbial biomass is suitable as animal feed.

The method of claim 1, wherein the at least one heterologous protein is superoxide dismutase and the at least one chemical product is ethylene.

The invention claimed is:

1. A process for continuous co-production of at least one chemical product and at least one exogenous gene product comprising:
   a) providing a continuous bioreactor;
   b) introducing to the bioreactor a recombinant C1-fixing microorganism selected from *Clostridium autoethanogenum* and *Cupriavidus necator* capable of co-producing at least one chemical product and at least one exogenous gene product, a gaseous substrate comprising one or more of CO, $CO_2$, and $H_2$, and a liquid growth medium;
   c) continuously culturing the recombinant C1-fixing microorganism thereby generating a gas fermentation broth comprising 1) the at least one chemical product, 2) the at least one exogenous gene product, and 3) microbial biomass;
   d) continuously removing a portion of the gas fermentation broth in a first stream;
   e) continuously removing the at least one chemical product in a second stream; and
   f) continuously recovering the at least one exogenous gene product from the microbial biomass from the first stream; wherein the at least one exogenous gene product is squid ring teeth (SRT) protein and wherein the at least one chemical product is selected from acetone, ethanol, ethylene, isoprene, and isopropanol.

2. The method of claim 1, wherein the at least one chemical product is ethylene.

3. The method of claim 1, further comprising separating the microbial biomass from the first stream before recovering the exogenous gene product.

4. The method of claim 1, further comprising the recombinant microorganism comprising a disruptive mutation in one or more genes.

5. The method of claim 1, further comprising the microbial biomass and at least one excipient.

6. The method of claim 1, wherein the microbial biomass is suitable as animal feed.

7. The method of claim 1, wherein the at least one heterologous protein is superoxide dismutase and the at least one chemical product is ethylene.

* * * * *

SEQUENCE LISTING

```
Sequence total quantity: 8
SEQ ID NO: 1          moltype = AA   length = 218
FEATURE               Location/Qualifiers
source                1..218
                      mol_type = protein
                      organism = Dosidicus gigas
SEQUENCE: 1
MWSHPQFEKG GGSGGGSGGS SAWSHPQFEK GGSGGGSGTA TLLFLMSMIA ALGCQSEAAI   60
SHGSHVKTVV HHGNGVRTVT HTIHHPVVHH GLHRTSIVPG TTTITHTTHD NRHPYGGVTT  120
VTHSNQGAHH PYSFGYGFGG PYGGGGLYG APYHMGTTVV NHPGHGMPYP YMYGSQGFGL   180
GGLSGLDYPV GSTVTHSNYG FHHPLGFGEP FNGPYGFQ                          218

SEQ ID NO: 2          moltype = AA   length = 199
FEATURE               Location/Qualifiers
source                1..199
                      mol_type = protein
                      organism = Dosidicus gigas
SEQUENCE: 2
MWSHPQFEKG GGSGGGSGGS SAWSHPQFEK GGSGGGSGAA ISHGSHVKTV VHHGNGVRTV   60
THTIHHPVVH HGLHRTSIVP GTTTITHTTH DNRHPYGGVT TVTHSNQGAH HPYSFGYGFG  120
GPYGGGGLY GAPYHMGTTV VNHPGHGMPY PYMYGSQGFG LGGLSGLDYP VGSTVTHSNY   180
GFHHPLGFGE PFNGPYGFQ                                               199

SEQ ID NO: 3          moltype = AA   length = 199
FEATURE               Location/Qualifiers
source                1..199
                      mol_type = protein
                      organism = Dosidicus gigas
SEQUENCE: 3
MWSHPQFEKG GGSGGGSGGS SAWSHPQFEK GGSGGGSGAF PGFMGGYGGA YPIGSSYSQV   60
THHGPYGMSG IGGFGGLGYG ASLPVSSVSH VSHGAHYGWG GMYGGGVQVS QSPVMYQGYS  120
VGAPHVQSMG VHYPTTTSVS HSHGGYLGGL GGIGAVGGYG GYGGYGLAGG LGHSVSTVSH  180
```

```
                          GIGHVGMGMG YGYGGFGHY                                  199

SEQ ID NO: 4              moltype = AA   length = 394
FEATURE                   Location/Qualifiers
source                    1..394
                          mol_type = protein
                          note = Vespa simillima xanthoptera
                          organism = Vespa sp.
SEQUENCE: 4
MWSHPQFEKG GGSGGGSGGS SAWSHPQFEK GGSGGGSGAS SSSSAESSAS ATASSDASWS       60
ASSRSSATGR APNVILNRAP QLGASAAAIA SARASTSANA ASDEKSARET RATALARSRA      120
AVTAAARAAA RTQEAVAAAK AASRAQALAA AKSSAAISAL AAGEAAAQKA DAAALAALAA      180
NQRSVKAAEN GLAVQNRANG EAEQASRAAA ANLAAAIRTR DNALETRREA ARLKALATAA      240
ANANNKATSL AEASANQAAE ASSAAEDTSS AQSAAVAQAE AAETLNVNLA ILESTQSSRQ      300
DSNVAKAEAS AAAKASPGTA TRDGVNLGLA SDAGAAAQLK AQAAALARAS SRISSGPALS      360
AWKWRNEDSS ESSTSAIASS SASSSSSSRS ASGN                                  394

SEQ ID NO: 5              moltype = AA   length = 200
FEATURE                   Location/Qualifiers
source                    1..200
                          mol_type = protein
                          note = SB 1003
                          organism = Rhodobacter capsulatus
SEQUENCE: 5
MAFELPALPY AHDALAALGM SKETLEYHHD LHHKAYVDNG NKLIAGTEWE GKSVEEIVKG        60
TYCAGAVAQS GIFNNASQHW NHAQFWEMMG PGEDKKMPGE LEKALVEAFG SVAKFKEDFA      120
AAGAAQFGSG WAWLVKDTDG ALKITKTENG VNPLCFGQTA LLGCDVWEHS YYIDFRNKRP      180
VYLTNFLDKL VNWENVASRL                                                  200

SEQ ID NO: 6              moltype = AA   length = 193
FEATURE                   Location/Qualifiers
source                    1..193
                          mol_type = protein
                          note = H16
                          organism = Cupriavidus necator
SEQUENCE: 6
MEHKLPPLPY AHDALAPHIS KETLEFHHDK HHQTYVTNLN NLIKGTEFEN STLEEIVKKS       60
SGGIFNNAAQ VWNHTFYWDS MKPNGGGQPT GALADAINAK WGSFDKFKEE FTKTAVGTFG      120
SGWAWLVKKA DGSLDLVSTS NAATPLTTDA KALLTCDVWE HAYYIDYRNA RPKYVEAFWN      180
VVNWDFAGKN FAG                                                         193

SEQ ID NO: 7              moltype = AA   length = 193
FEATURE                   Location/Qualifiers
source                    1..193
                          mol_type = protein
                          note = KCTC 2242
                          organism = Klebsiella pneumoniae
SEQUENCE: 7
MSFELPALPY AKDALAPHIS AETLEYHYGK HHQAYVTNLN NLIKGTAFEG KSLEEIVRTS       60
EGGVFNNAAQ VWNHTFYWNC LAPNAGGEPE GELAAAIAKS FGSFADFKAK FTDAAAKNFG      120
AGWTWLVKNA DGSLAIVSTS NAGTPLTTDA KPLLTVDVWE HAYYIDYRNA RPSYLDHFWA      180
LVNWKFVAAN LAA                                                         193

SEQ ID NO: 8              moltype = AA   length = 206
FEATURE                   Location/Qualifiers
source                    1..206
                          mol_type = protein
                          note = KCTC 2242
                          organism = Klebsiella pneumoniae
SEQUENCE: 8
MSYTLPSLPY AYDALEPHFD KQTMEIHHTK HHQTYVNNAN AALESLPEFA NLSAEELITK       60
LDQLPADKKT VLRNNAGGHA NHSLFWKGLK TGTTLQGDLK AAIERDFGSV ENFKAEFEKA      120
AATRFGSGWA WLVLKGDKLA VVSTANQDSP LMGEAISGAS GFPIIGLDVW EHAYYLKFQN      180
RRPDYIKAFW DVVNWDEAAA RFAAKK                                           206
```